(12) United States Patent
Greenberg et al.

(10) Patent No.: US 11,832,818 B2
(45) Date of Patent: Dec. 5, 2023

(54) TISSUE ALIGNMENT FOR SURGICAL CLOSURE

(71) Applicant: Seger Surgical Solutions Ltd., Misgav (IL)

(72) Inventors: Yaakov Greenberg, Even-Yehuda (IL); Shahar Harari, Tel Aviv (IL); Barry Salky, Snowmass Village, CO (US); Yaron Fuerst, Kfar-Vradim (IL)

(73) Assignee: Seger Surgical Solutions Ltd., Misgav (IL)

( * ) Notice: Subject to any disclaimer, the term of this patent is extended or adjusted under 35 U.S.C. 154(b) by 519 days.

(21) Appl. No.: 16/959,714

(22) PCT Filed: Jan. 3, 2019

(86) PCT No.: PCT/IL2019/050022
§ 371 (c)(1),
(2) Date: Jul. 2, 2020

(87) PCT Pub. No.: WO2019/135236
PCT Pub. Date: Jul. 11, 2019

(65) Prior Publication Data
US 2020/0345367 A1    Nov. 5, 2020

Related U.S. Application Data

(60) Provisional application No. 62/613,444, filed on Jan. 4, 2018.

(51) Int. Cl.
*A61B 17/08* (2006.01)
*A61B 17/072* (2006.01)
(Continued)

(52) U.S. Cl.
CPC ........ *A61B 17/08* (2013.01); *A61B 17/07207* (2013.01); *A61B 17/1114* (2013.01);
(Continued)

(58) Field of Classification Search
CPC .......... A61B 17/083; A61B 2017/1103; A61B 2017/081
See application file for complete search history.

(56) References Cited

U.S. PATENT DOCUMENTS 4,506,669 A * 3/1985 Blake, III ............ A61B 17/083
294/99.2
5,007,921 A * 4/1991 Brown ................. A61B 17/083
606/221
(Continued)

FOREIGN PATENT DOCUMENTS

DE   202013004861   7/2013
WO   2015195568     12/2015

OTHER PUBLICATIONS

PCT Search Report and Written Opinion PCT/IL2019/050022, dated Apr. 15, 2019.

*Primary Examiner* — Shaun L David
(74) *Attorney, Agent, or Firm* — Dekel Patent Ltd.; David Klein

(57) ABSTRACT

A device for laparoscopically approximating edges of a tissue opening toward each other for surgical attachment, the device including a first tissue engaging component, and a second tissue engaging component, a spreader component for moving the first tissue engaging component away from the second tissue engaging component, and a control for moving the first tissue engaging component away from the second tissue engaging component. Related apparatus and methods are also described.

9 Claims, 31 Drawing Sheets

(51) Int. Cl.
*A61B 17/11* (2006.01)
*A61B 17/29* (2006.01)

(52) U.S. Cl.
CPC .... *A61B 17/29* (2013.01); *A61B 2017/07285* (2013.01); *A61B 2017/081* (2013.01); *A61B 2017/2906* (2013.01); *A61B 2017/2927* (2013.01)

(56) References Cited

U.S. PATENT DOCUMENTS

| | | | | |
|---|---|---|---|---|
| 5,026,390 | A * | 6/1991 | Brown | A61B 17/8019 606/221 |
| 5,030,224 | A * | 7/1991 | Wright | A61B 17/083 600/209 |
| 5,972,021 | A * | 10/1999 | Huttner | A61B 17/08 606/205 |
| 5,997,567 | A * | 12/1999 | Cangelosi | A61B 17/30 294/99.2 |
| 6,042,599 | A * | 3/2000 | Huttner | A61B 17/08 606/208 |
| 6,283,984 | B1 * | 9/2001 | Ray | A61B 17/30 606/205 |
| 6,863,679 | B1 * | 3/2005 | Aaron | A61B 17/30 606/210 |
| 2003/0065385 | A1 * | 4/2003 | Weadock | A61F 2/07 623/1.36 |
| 2004/0059377 | A1 * | 3/2004 | Peterson | A61B 17/064 606/216 |
| 2005/0049618 | A1 * | 3/2005 | Masuda | A61B 17/1285 606/151 |
| 2005/0251155 | A1 * | 11/2005 | Orban, III | A61B 17/115 606/153 |
| 2006/0025788 | A1 * | 2/2006 | Loshakove | A61B 17/11 606/153 |
| 2006/0293698 | A1 * | 12/2006 | Douk | A61B 17/128 623/900 |
| 2008/0125796 | A1 * | 5/2008 | Graham | A61B 17/0057 600/153 |
| 2008/0177300 | A1 * | 7/2008 | Mas | A61B 17/0057 606/151 |
| 2008/0249566 | A1 * | 10/2008 | Harris | A61F 5/0086 606/220 |
| 2008/0319455 | A1 * | 12/2008 | Harris | A61B 17/0684 606/139 |
| 2009/0039138 | A1 | 2/2009 | Bender | |
| 2009/0275957 | A1 * | 11/2009 | Harris | A61B 17/064 227/176.1 |
| 2012/0046590 | A1 * | 2/2012 | Yock | A61B 17/085 602/53 |
| 2015/0182365 | A1 | 7/2015 | Harris et al. | |
| 2017/0296161 | A1 | 10/2017 | Marshall | |
| 2019/0105046 | A1 * | 4/2019 | Jagelski | A61B 17/0057 |
| 2019/0159783 | A1 * | 5/2019 | Lehtinen | A61B 17/122 |

* cited by examiner

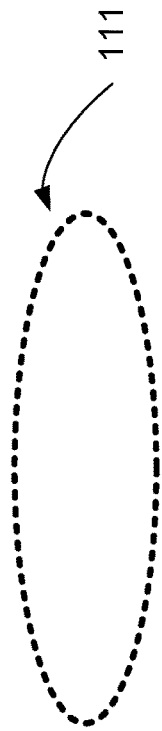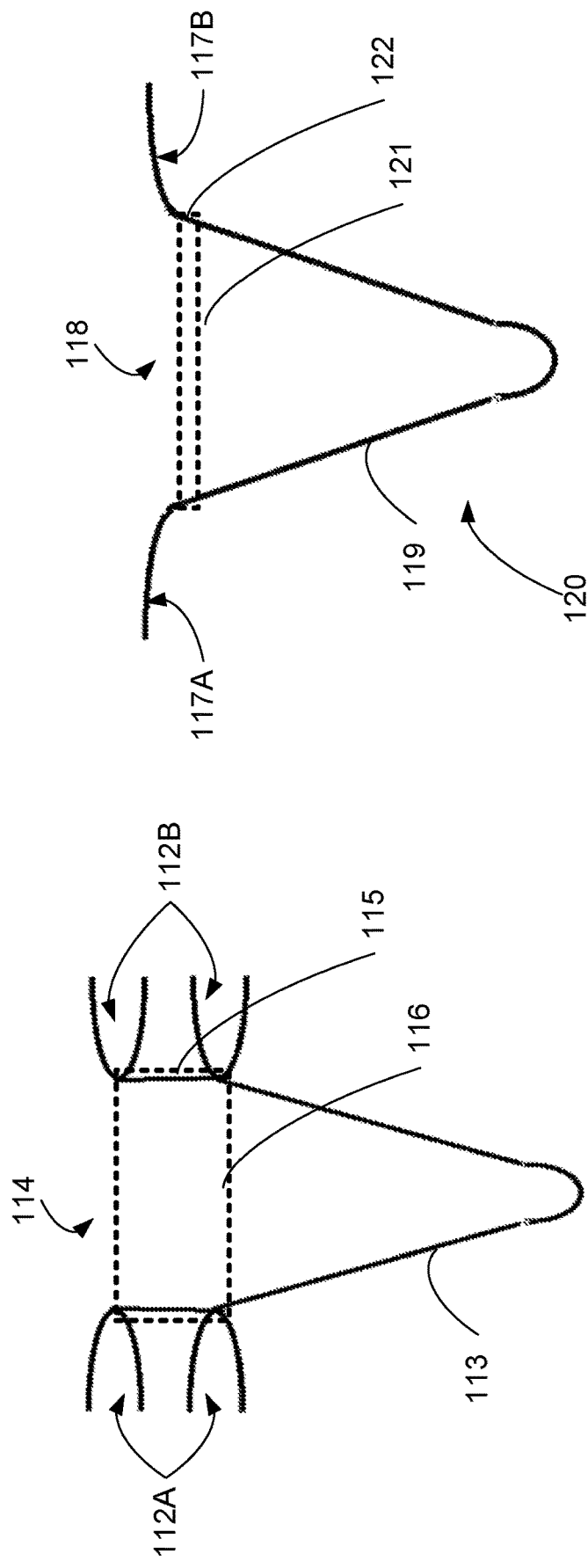
FIG. 1B
FIG. 1C
PRIOR ART
FIG. 1D

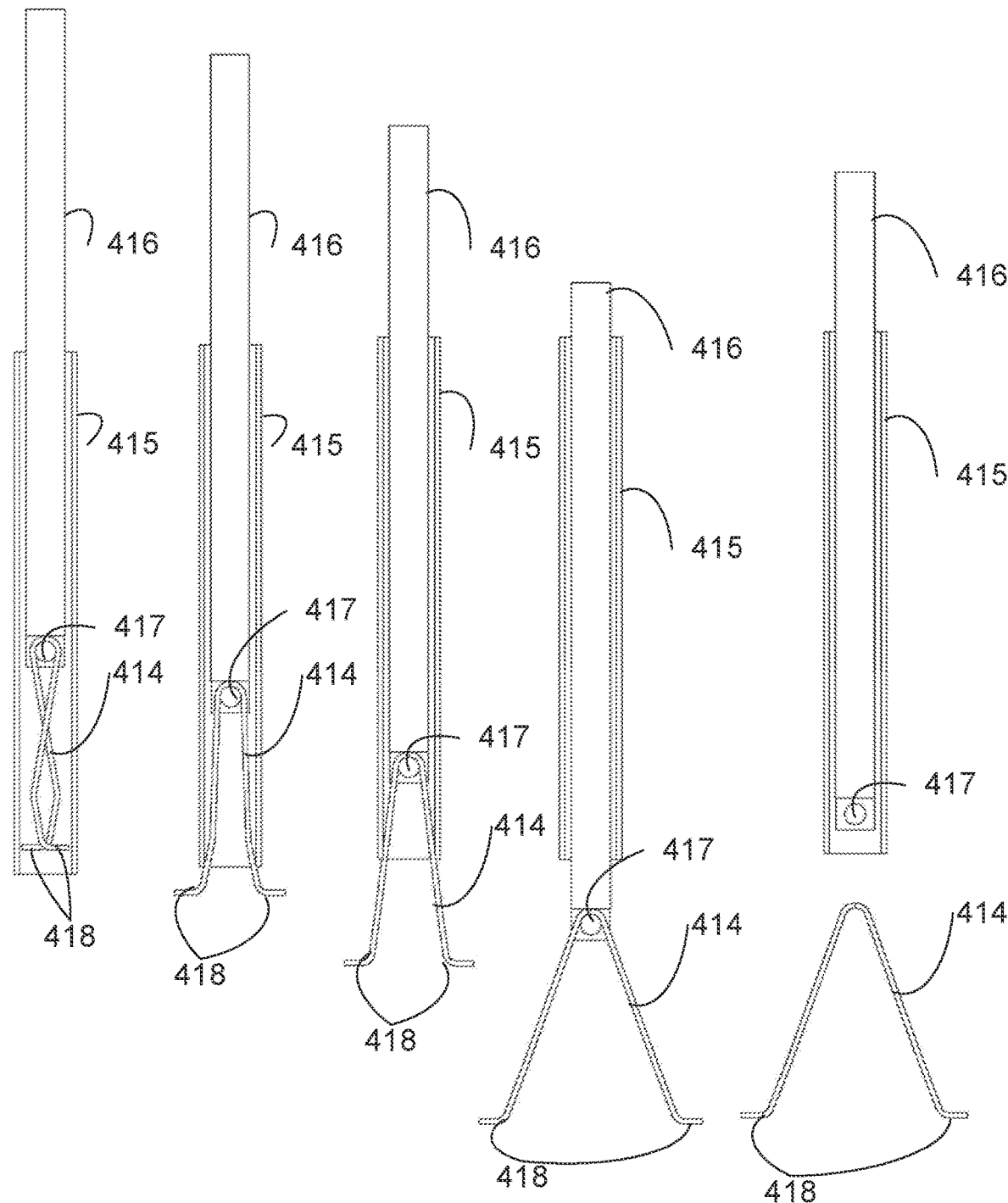

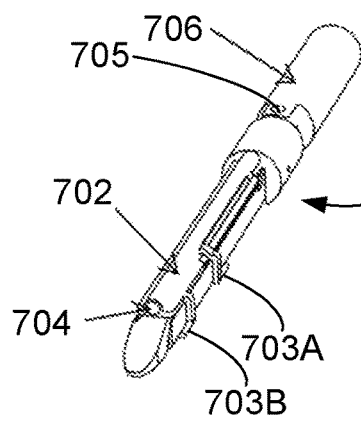
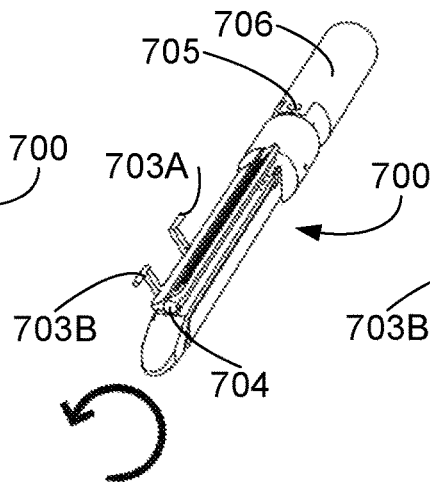
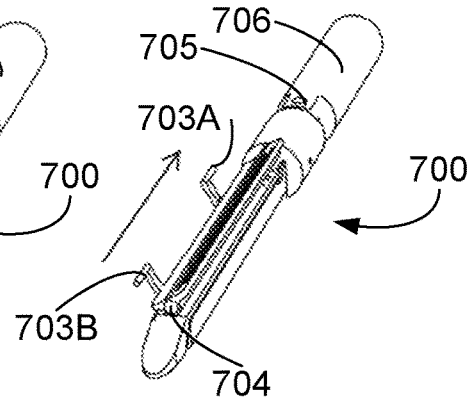
FIG. 7A      FIG. 7B      FIG. 7C
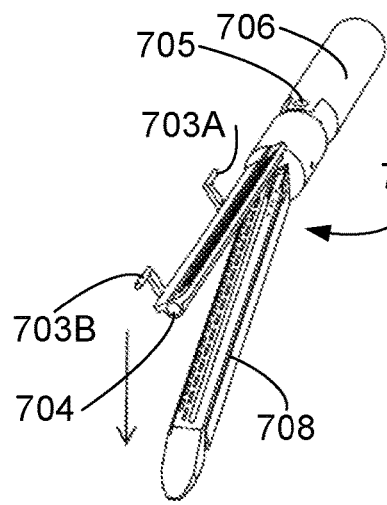
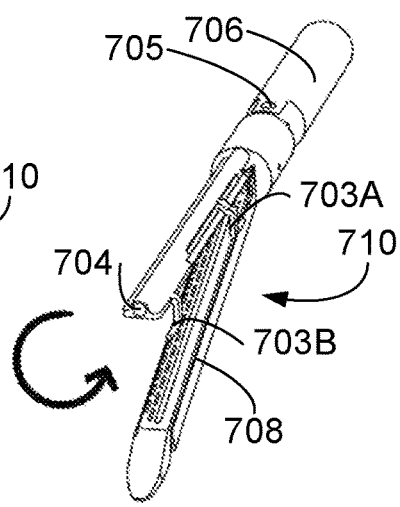
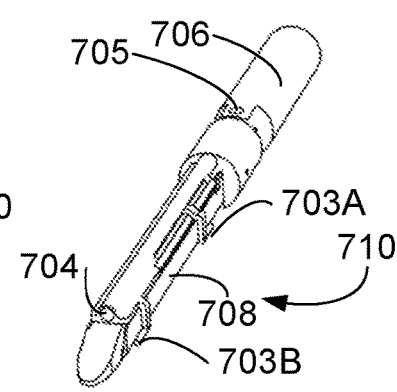
FIG. 7D      FIG. 7E      FIG. 7F

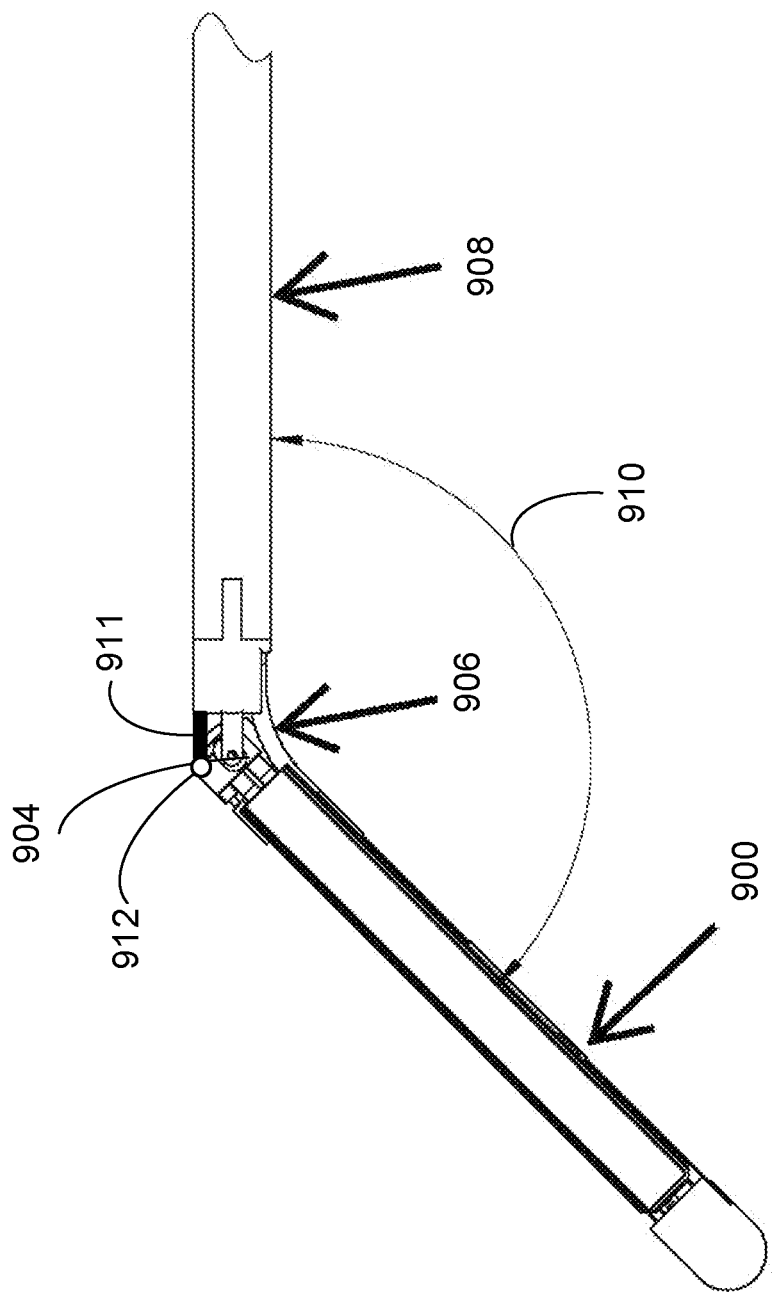

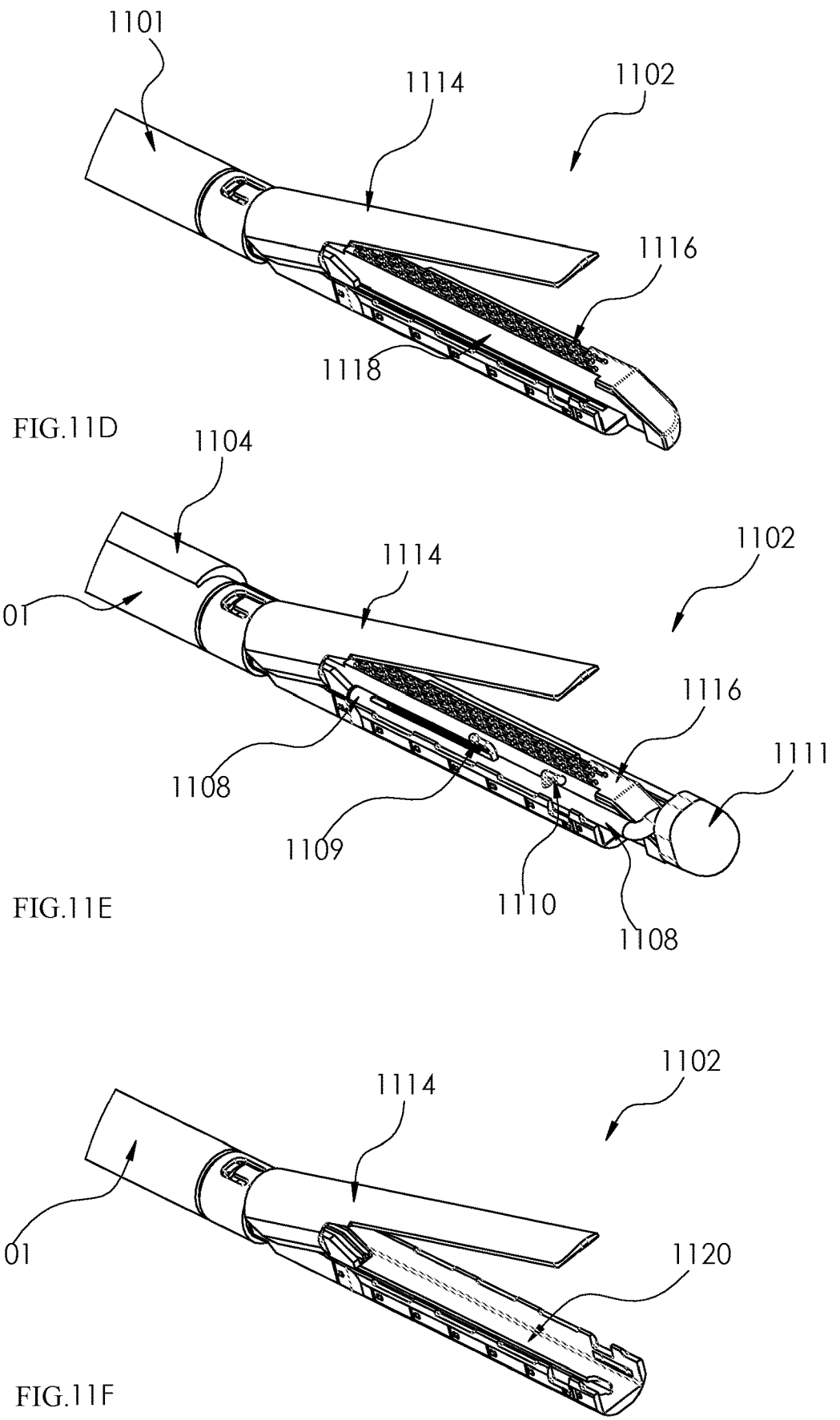

TISSUE ALIGNMENT FOR SURGICAL CLOSURE

RELATED APPLICATION/S

This application is a PCT application claiming the benefit of priority of U. S. Provisional Patent Application No. 62/613,444 filed Jan. 4, 2018, the contents of which are incorporated herein by reference in their entirety.

FIELD AND BACKGROUND OF THE INVENTION

The present invention, in some embodiments thereof, relates to devices and methods for aligning tissue for surgical attachment and optionally surgically attaching the tissue and, more particularly, but not exclusively, to laparoscopic devices and methods for the above.

The disclosures of all references mentioned throughout the present specification, as well as the disclosures of all references mentioned in those references, are hereby incorporated herein by reference.

SUMMARY OF THE INVENTION

The present invention, in some embodiments thereof, relates to a method of pulling edges of a tissue opening so the edges draw toward each other, making the edges easy to suture or staple closed.

The present invention, in some embodiments thereof, relates to a method of laparoscopic operation which includes pulling edges of a tissue opening so the edges draw toward each other, making the edges easy to suture or staple closed. In some embodiments the method includes subsequent stapling of the edges closed. In some embodiments the method includes cutting extra tissue off close to a line of stapling.

The present invention, in some embodiments thereof, relates to a device for pulling edges of a tissue opening so the edges draw toward each other, making the edges easy to suture or staple closed. In some embodiments the device includes stapler rests or an alignment structure, so a stapler can be positioned, based on the stapler rests/alignment structure, at a correct position for stapling the tissue edges closed.

The present invention, in some embodiments thereof, relates to a device for laparoscopic operation which includes pulling edges of a tissue opening so the edges draw toward each other, making the edges easy to suture or staple closed. In some embodiments the device includes stapler rests or an alignment structure, so a laparoscopic stapler can be positioned, based on the stapler rests/alignment structure, at a correct position for stapling the tissue edges closed. In some embodiments the device includes a mechanism for pulling the tissue edges to between a stapler and an anvil, or pulling a stapler and/or anvil toward the tissue edges, so that the stapler can staple the edges closed.

According to an aspect of some embodiments of the present invention there is provided a device for drawing edges of a tissue opening toward each other for surgical attachment, the device including a first tissue engaging component configured to engage a slit in tissue near a first end of the slit, and a second tissue engaging component configured to engage the slit near a second end of the slit, wherein the device includes rests for aligning a tissue attachment mechanism parallel to a line between the first tissue engaging component and the second tissue engaging component.

According to some embodiments of the invention, the rests for aligning the tissue attachment mechanism are configured to locate the tissue attachment mechanism parallel to the line between the first tissue engaging component and the second tissue engaging component and a specific distance away from the line, the specific distance in a range between 2 millimeters and 10 millimeters.

According to some embodiments of the invention, further including a mechanism for pulling the first tissue engaging component and the second tissue engaging component by rotating the first tissue engaging component and the second tissue engaging component.

According to some embodiments of the invention, further including a mechanism for pulling the first tissue engaging component and the second tissue engaging component sideways by using a parallelogram-shaped linkage.

According to some embodiments of the invention, further including a tissue attachment mechanism. According to some embodiments of the invention, the tissue attachment mechanism includes a tissue stapler.

According to some embodiments of the invention, the first tissue engaging component and the second tissue engaging component are located between the tissue stapler and a stapler anvil.

According to some embodiments of the invention, at least one of the first tissue engaging component and the second tissue engaging component includes a tissue grasper.

According to some embodiments of the invention, at least one of the first tissue engaging component and the second tissue engaging component includes a prong. According to some embodiments of the invention, the first tissue engaging component includes a first prong and the second tissue engaging component includes a second prong.

According to some embodiments of the invention, the first prong is configured to enter the slit in the tissue, a tip of the first prong pointing in a first direction, and the second prong is configured to enter the slit in the tissue, a tip of the second prong pointing in a second direction, at least 90 degrees away from the first direction.

According to some embodiments of the invention, each one of the first prong and the second prong is configured to contact an edge of the slit in the tissue along a contact location as wide as a diameter of the prong. According to some embodiments of the invention, a length of the contact location is less than 5 millimeters.

According to some embodiments of the invention, one of the first prong and the second prong is configured to slide along tissue. According to some embodiments of the invention, both the first prong and the second prong are configured to slide along tissue.

According to some embodiments of the invention, one of the first tissue engaging component and the second tissue engaging component is configured to grab tissue. According to some embodiments of the invention, both of the first tissue engaging component and the second tissue engaging component are configured to grab tissue.

According to some embodiments of the invention, further including a spring for pushing the first tissue engaging component and the second tissue engaging component apart.

According to some embodiments of the invention, the spring is configured to push the first tissue engaging component and the second tissue engaging component apart with a specific force.

According to some embodiments of the invention, the specific force is in a range between 50 grams force and 200 grams force. According to some embodiments of the invention, the specific force is provided by a spring. According to some embodiments of the invention, the specific force is adjustable. According to some embodiments of the invention, the specific force is adjustable dynamically, from a control outside a patient's body.

According to some embodiments of the invention, the specific force is adjustable by adjusting a spring in a component inserted into the patient's body.

According to some embodiments of the invention, further including a limiting component configured to limit movement of the first tissue engaging component and the second tissue engaging component apart to no more than a specific distance. According to some embodiments of the invention, the specific distance is in a range between 10 millimeters and 100 millimeters.

According to some embodiments of the invention, further including a maintainer component for preventing the spring from pushing the first tissue engaging component and the second tissue engaging component apart before the maintainer is actuated.

According to some embodiments of the invention, the device is configured to be operated laparoscopically.

According to some embodiments of the invention, shaped and sized to pass through a trocar. According to some embodiments of the invention, the device has a maximum diameter in a range between 5 millimeters and 15 millimeters.

According to some embodiments of the invention, the device further includes a tissue cutter.

According to some embodiments of the invention, the tissue attachment mechanism is aligned to staple tissue along a second line parallel to a first line between the first tissue engaging component and the second tissue engaging component, and the tissue cutter is configured to cut tissue along a third line parallel to the second line and on an opposing side of the second line relative to the first line.

According to an aspect of some embodiments of the present invention there is provided a device for laparoscopically drawing edges of a tissue opening toward each other for surgical attachment, the device including a first tissue engaging component configured to engage a slit in tissue near a first end of the slit, and a second tissue engaging component configured to engage the slit near a second end of the slit, a spreader component configured to move the first tissue engaging component away from the second tissue engaging component, and a control for moving the first tissue engaging component away from the second tissue engaging component, the control configured to be external to a patient's body.

According to some embodiments of the invention, further including tissue attachment mechanism rests for aligning a tissue attachment mechanism parallel to a line between the first tissue engaging component and the second tissue engaging component.

According to some embodiments of the invention, the tissue attachment mechanism rests for aligning the tissue attachment mechanism are configured to locate the tissue attachment mechanism parallel to the line between the first tissue engaging component and the second tissue engaging component and a specific distance away from the line, the specific distance in a range between 2 millimeters and 10 millimeters.

According to some embodiments of the invention, further including a mechanism for pulling the first tissue engaging component and the second tissue engaging component by rotating the first tissue engaging component and the second tissue engaging component.

According to some embodiments of the invention, further including a mechanism for pulling the first tissue engaging component and the second tissue engaging component sideways by using a parallelogram-shaped linkage.

According to some embodiments of the invention, further including a wire attached to at least one of the first tissue engaging component and the second tissue engaging component, the wire extending to the control for moving the first tissue engaging component away from the second tissue engaging component.

According to some embodiments of the invention, further including a spring for pushing the first tissue engaging component and the second tissue engaging component apart, the spring located in the device at a location configured to be external to the patient's body.

According to some embodiments of the invention, further including a spring for pushing the first tissue engaging component and the second tissue engaging component apart, the spring located in the device at a location configured to be internal to the patient's body.

According to some embodiments of the invention, further including a maintainer component for preventing the spring from pushing the first tissue engaging component and the second tissue engaging component apart before the maintainer is actuated, and a first control for actuating the maintainer, the control located in the device at a location configured to be external to the patient's body.

According to some embodiments of the invention, at least one of the first tissue engaging component and the second tissue engaging component includes a tissue grasper.

According to some embodiments of the invention, at least one of the first tissue engaging component and the second tissue engaging component includes a prong.

According to some embodiments of the invention, the first tissue engaging component includes a first prong and the second tissue engaging component includes a second prong.

According to some embodiments of the invention, the first prong is configured to enter the slit in the tissue, a tip of the first prong pointing in a first direction, and the second prong is configured to enter the slit in the tissue, a tip of the second prong pointing in a second direction, at least 90 degrees away from the first direction.

According to some embodiments of the invention, further including a tissue attachment mechanism for surgically attaching edges of the opening in the tissue to each other, and a second control for actuating the tissue attachment mechanism, the control located in the device at a location configured to be external to the patient's body.

According to some embodiments of the invention, further including a tissue stapler, and a second control for actuating the tissue stapler, the control located in the device at a location configured to be external to the patient's body.

According to some embodiments of the invention, the first tissue engaging component and the second tissue engaging component are located between the tissue stapler and a stapler anvil.

According to some embodiments of the invention, the first tissue engaging component and the second tissue engaging component are configured to maneuver the edges of the tissue opening between jaws of the tissue stapler.

According to some embodiments of the invention, the device is shaped and sized to pass through a trocar.

According to some embodiments of the invention, a first portion of the device, configured to operate within a patient's body, has a maximum diameter in a range between 5 millimeters and 15 millimeters.

According to some embodiments of the invention, the tissue stapler is a narrow tissue stapler, including no more than 3 rows of staples.

According to some embodiments of the invention, the tissue stapler is aligned to staple tissue along a second line parallel to a first line between the first tissue engaging component and the second tissue engaging component.

According to some embodiments of the invention, the device further includes a tissue cutter.

According to some embodiments of the invention, the tissue stapler is aligned to staple tissue along a second line parallel to a first line between the first tissue engaging component and the second tissue engaging component, and the tissue cutter is configured to cut tissue along a third line parallel to the second line and on an opposing side of the second line relative to the first line.

According to some embodiments of the invention, further including a laparoscope for viewing inside a patient's body.

According to an aspect of some embodiments of the present invention there is provided a method for drawing edges of a tissue opening toward each other for surgical closure of the tissue opening, the method including engaging a first tissue engaging component with tissue near a first end of a slit in tissue, engaging a second tissue engaging component with tissue near a second end of the slit, and moving the first tissue engaging component away from the second tissue engaging component, thereby drawing edges of the slit in the tissue together.

According to some embodiments of the invention, further including additionally pulling the first tissue engaging component and the second tissue engaging component in a directional perpendicular to a direction of the slit, thereby pulling edges of the slit in the tissue to form parallel surfaces of tissue, for surgical closure of the tissue.

According to some embodiments of the invention, further including additionally pulling the first tissue engaging component and the second tissue engaging component by rotating the first tissue engaging component and the second tissue engaging component.

According to some embodiments of the invention, further including additionally pulling the first tissue engaging component and the second tissue engaging component by using a parallelogram-shaped linkage.

According to some embodiments of the invention, moving the first tissue engaging component away from the second tissue engaging component includes releasing a spring which pushes the first tissue engaging component away from the second tissue engaging component.

According to some embodiments of the invention, the engaging the first tissue engaging component with tissue near the first end of the slit in tissue includes inserting a first prong into the slit in the tissue, and the engaging the second tissue engaging component with tissue near the second end of the slit includes inserting a second prong into the slit in the tissue.

According to some embodiments of the invention, further including suturing the tissue opening. According to some embodiments of the invention, further including cutting excess tissue away from a suturing line.

According to some embodiments of the invention, further including placing a stapler in contact with the first tissue engaging component and the second tissue engaging component.

According to some embodiments of the invention, further including placing a stapler in contact with stapler support locations on the first tissue engaging component and the second tissue engaging component.

According to some embodiments of the invention, the pulling the first tissue engaging component and the second tissue engaging component causes the edges of the slit in the tissue to be pulled toward the tissue stapler.

According to some embodiments of the invention, the pulling the first tissue engaging component and the second tissue engaging component causes the tissue stapler to be pulled toward the edges of the slit in the tissue.

According to some embodiments of the invention, the edges of the slit in the tissue are located between the tissue stapler and an anvil.

According to some embodiments of the invention, further including stapling the tissue. According to some embodiments of the invention, further including cutting excess tissue away from a stapling line.

According to an aspect of some embodiments of the present invention there is provided a method for drawing edges of a tissue opening toward each other for laparoscopic surgical closure of an opening in tissue, the method including inserting a device for drawing edges of a tissue opening toward each other for surgical attachment through a keyhole incision in a patient's body, the device including a first tissue engaging component configured to engage a slit in tissue near a first end of the slit, a second tissue engaging component configured to engage the slit near a second end of the slit, and a spreader component configured to move the first tissue engaging component away from the second tissue engaging component, engaging a first tissue engaging component with tissue near a first end of a slit in tissue, engaging a second tissue engaging component with tissue near a second end of the slit, and moving the first tissue engaging component away from the second tissue engaging component, thereby causing edges of the tissue to move toward each other.

According to some embodiments of the invention, further including additionally pulling the first tissue engaging component and the second tissue engaging component in a directional perpendicular to a longitudinal direction of the slit, thereby pulling edges of the slit in the tissue to form parallel surfaces of tissue, for surgical closure of the tissue.

According to some embodiments of the invention, further including additionally pulling the first tissue engaging component and the second tissue engaging component by rotating the first tissue engaging component and the second tissue engaging component.

According to some embodiments of the invention, further including additionally pulling the first tissue engaging component and the second tissue engaging component by using a parallelogram-shaped linkage.

According to some embodiments of the invention, moving the first tissue engaging component away from the second tissue engaging component includes releasing a spring which pushes the first tissue engaging component away from the second tissue engaging component by operating a spring release control outside a patient's body.

According to some embodiments of the invention, the engaging the first tissue engaging component with tissue near the first end of the slit in tissue includes inserting a first prong into the slit in the tissue, and the engaging the second tissue engaging component with tissue near the second end of the slit includes inserting a second prong into the slit in the tissue.

According to some embodiments of the invention, further including suturing the tissue.

According to some embodiments of the invention, further including placing a stapler in contact with the first tissue engaging component and the second tissue engaging component.

According to some embodiments of the invention, further including placing a stapler in contact with stapler support locations on the first tissue engaging component and the second tissue engaging component.

According to some embodiments of the invention, the device further includes a tissue stapler, and further including maneuvering the stapler to a location parallel to tissue edges.

According to some embodiments of the invention, the device is shaped to locate the tissue stapler parallel to the tissue edges and a specific distance away from the tissue edges, the specific distance in a range of 2 millimeters to 10 millimeters.

According to some embodiments of the invention, the pulling the first tissue engaging component and the second tissue engaging component causes the edges of the slit in the tissue to be pulled toward the tissue stapler.

According to some embodiments of the invention, the pulling the first tissue engaging component and the second tissue engaging component causes the tissue stapler to be pulled toward the edges of the slit in the tissue.

According to some embodiments of the invention, the edges of the slit in the tissue are located between the tissue stapler and an anvil.

According to some embodiments of the invention, further including stapling the tissue opening. According to some embodiments of the invention, the stapling is along a second line parallel to a first line between the first tissue engaging component and the second tissue engaging component. According to some embodiments of the invention, further including cutting tissue.

According to some embodiments of the invention, the stapling is along a second line parallel to a first line between the first tissue engaging component and the second tissue engaging component, and the cutting is along a third line parallel to the second line and on an opposing side of the second line relative to the first line.

According to some embodiments of the invention, further including using a laparoscope for viewing inside a patient's body.

According to an aspect of some embodiments of the present invention there is provided a device for laparoscopically approximating edges of a tissue opening toward each other for surgical attachment, the device including a first tissue engaging component, and a second tissue engaging component, a spreader component for moving the first tissue engaging component away from the second tissue engaging component, and a control for moving the first tissue engaging component away from the second tissue engaging component.

According to some embodiments of the invention, the device is shaped as an elongate device, including a first end of the elongate device which includes the first tissue engaging component, the second tissue engaging component and the spreader component, and a second end of the elongate device which includes the control.

According to some embodiments of the invention, further including rests for aligning a tissue attachment mechanism parallel to a line between the first tissue engaging component and the second tissue engaging component.

According to some embodiments of the invention, further including a mechanism for rotating the first tissue engaging component and the second tissue engaging component relative to an axis of the elongate device.

According to some embodiments of the invention, further including a wire attached to at least one of the first tissue engaging component and the second tissue engaging component, the wire extending to the control for moving the first tissue engaging component away from the second tissue engaging component.

According to some embodiments of the invention, further including a spring for pushing the first tissue engaging component and the second tissue engaging component apart, the spring located in the first end of the elongate device.

According to some embodiments of the invention, further including a spring for pushing the first tissue engaging component and the second tissue engaging component apart, the spring located in the second end of the elongate device.

According to some embodiments of the invention, the first tissue engaging component includes a first prong and the second tissue engaging component includes a second prong.

According to some embodiments of the invention, the first tissue engaging component and the second tissue engaging component include shape memory material.

According to some embodiments of the invention, the first prong is configured to enter the opening in the tissue, a tip of the first prong pointing in a first direction, and the second prong is configured to enter the opening in the tissue, a tip of the second prong pointing in a second direction, at least 90 degrees away from the first direction.

According to some embodiments of the invention, further including a tissue attachment mechanism for surgically attaching edges of the opening in the tissue to each other located in the first end of the elongate device, and a second control for actuating the tissue attachment mechanism, the control located in the second end of the elongate device.

According to some embodiments of the invention, further including a tissue stapler located in the first end of the elongate device, and a second control for actuating the tissue stapler, the control located in the second end of the elongate device.

According to some embodiments of the invention, the tissue stapler includes a stapler side and a stapler anvil side, and the first tissue engaging component and the second tissue engaging component are attached to the stapler side.

According to some embodiments of the invention, the tissue stapler includes a stapler side and a stapler anvil side, and the first tissue engaging component and the second tissue engaging component are attached to the stapler anvil side.

According to some embodiments of the invention, the first tissue engaging component and the second tissue engaging component are arranged to pull the edges of the tissue opening between jaws of the tissue stapler.

According to some embodiments of the invention, the device is shaped and sized to pass through a trocar wherein a first portion of the device, configured to operate within a patient's body, has a maximum diameter in a range between 5 millimeters and 15 millimeters.

According to some embodiments of the invention, the tissue stapler is a narrow tissue stapler, including no more than 3 rows of staples.

According to some embodiments of the invention, the first end of the elongate device is attached to a distal end of a shaft of the device configured to be detachable from the second end of the elongate device.

According to an aspect of some embodiments of the present invention there is provided a system for laparoscopic stapling of tissue including a tissue aligning device for laparoscopically approximating edges of a tissue opening toward each other for surgical attachment, for adding onto a laparoscopic tissue stapler, the tissue aligning device including a first tissue engaging component configured to engage an opening in tissue at a first location in the opening, and a second tissue engaging component configured to engage the opening at a second location in the opening, a spreader component configured to move the first tissue engaging component away from the second tissue engaging component, and a control for moving the first tissue engaging component away from the second tissue engaging component, and a tissue stapler.

According to an aspect of some embodiments of the present invention there is provided a device for laparoscopically approximating edges of a tissue opening toward each other for surgical attachment including a first tissue engaging component configured to engage an opening in tissue at a first location in the opening, and a second tissue engaging component configured to engage the opening at a second location in the opening, a spreader component configured to move the first tissue engaging component away from the second tissue engaging component, and a control for moving the first tissue engaging component away from the second tissue engaging component wherein the first tissue engaging component the second tissue engaging component and the spreader component are attached to a distal end of a shaft of the device configured to be detachable from a proximal end of the device.

According to an aspect of some embodiments of the present invention there is provided a device for approximating edges of a tissue opening toward each other for surgical attachment, the device including a first tissue engaging component configured to engage an opening in tissue at a first location in the opening, and a second tissue engaging component configured to engage the opening at a second location in the opening, wherein the device includes rests for aligning a tissue attachment mechanism parallel to a line between the first tissue engaging component and the second tissue engaging component.

According to some embodiments of the invention, the rests for aligning the tissue attachment mechanism are configured to locate the tissue attachment mechanism parallel to the line between the first tissue engaging component and the second tissue engaging component and a specific distance away from the line, the specific distance in a range between 2 millimeters and 10 millimeters.

According to some embodiments of the invention, further including a tissue attachment mechanism.

According to some embodiments of the invention, the tissue attachment mechanism includes a tissue stapler.

According to some embodiments of the invention, the first tissue engaging component and the second tissue engaging component are located between the tissue stapler and a stapler anvil.

According to some embodiments of the invention, further including a spring for pushing the first tissue engaging component and the second tissue engaging component apart.

According to some embodiments of the invention, the spring is configured to push the first tissue engaging component and the second tissue engaging component apart with a specific force in a range between 50 grams force and 200 grams force.

According to some embodiments of the invention, the specific force is adjustable dynamically, from a control outside a patient's body.

According to some embodiments of the invention, the device is shaped and sized to pass through a trocar wherein the device has a maximum diameter in a range between 5 millimeters and 15 millimeters.

According to an aspect of some embodiments of the present invention there is provided a method for approximating edges of a tissue opening toward each other for laparoscopic surgical closure of an opening in tissue, the method including inserting a device for approximating edges of a tissue opening toward each other for surgical attachment through a keyhole incision in a patient's body, the device including a first tissue engaging component, a second tissue engaging component, and a spreader component configured to move the first tissue engaging component away from the second tissue engaging component, engaging the first tissue engaging component with tissue at a first location in the opening in tissue, engaging the second tissue engaging component with tissue at a second location in the opening, and moving the first tissue engaging component away from the second tissue engaging component, thereby causing edges of the tissue to move toward each other.

According to some embodiments of the invention, further including additionally pulling the first tissue engaging component and the second tissue engaging component in a directional perpendicular to a direction of the opening, thereby pulling edges of the opening in the tissue to form parallel surfaces of tissue, for surgical closure of the tissue.

According to some embodiments of the invention, further including additionally pulling the first tissue engaging component and the second tissue engaging component by rotating the first tissue engaging component and the second tissue engaging component.

According to some embodiments of the invention, moving the first tissue engaging component away from the second tissue engaging component includes releasing a spring which pushes the first tissue engaging component away from the second tissue engaging component by operating a spring release control outside a patient's body.

According to some embodiments of the invention, the engaging the first tissue engaging component with tissue at the first location in the opening in tissue includes inserting a first prong into the opening in the tissue, and the engaging the second tissue engaging component with tissue at the second location in the opening includes inserting a second prong into the opening in the tissue.

According to some embodiments of the invention, further including placing a stapler in contact with the first tissue engaging component and the second tissue engaging component.

According to some embodiments of the invention, further including placing a stapler in contact with stapler support locations on the first tissue engaging component and the second tissue engaging component.

According to some embodiments of the invention, the device further includes a tissue stapler, and further including maneuvering the stapler to a location parallel to tissue edges, wherein the device is shaped to locate the tissue stapler parallel to the tissue edges and a specific distance away from the tissue edges, the specific distance in a range of 2 millimeters to 10 millimeters.

According to some embodiments of the invention, the pulling the first tissue engaging component and the second tissue engaging component causes the edges of the opening in the tissue to be pulled toward the tissue stapler.

According to some embodiments of the invention, the edges of the opening in the tissue are located between the tissue stapler and an anvil.

According to some embodiments of the invention, further including stapling the tissue opening.

According to some embodiments of the invention, further including cutting tissue.

According to an aspect of some embodiments of the present invention there is provided a method for constructing a device for laparoscopic surgical closure of an opening in tissue, the method including providing an add-on device for laparoscopically approximating edges of a tissue opening toward each other for surgical attachment, for adding onto a laparoscopic tissue stapler, the add-on device including a first tissue engaging component, and a second tissue engaging component, and a spreader component configured to move the first tissue engaging component away from the second tissue engaging component, providing a tissue stapler, and mounting the add-on device onto the tissue stapler.

According to an aspect of some embodiments of the present invention there is provided a method for approximating edges of a tissue opening toward each other for surgical closure of the tissue opening, the method including engaging a first tissue engaging component with tissue at a first location in an opening in tissue, engaging a second tissue engaging component with tissue at a second location in the opening, and moving the first tissue engaging component away from the second tissue engaging component, approximating edges of the opening in the tissue together, in an amount sufficient to shape the opening in the tissue as an elongate slit.

According to some embodiments of the invention, further including additionally pulling the first tissue engaging component and the second tissue engaging component in a direction perpendicular to a direction of the opening, thereby pulling edges of the opening in the tissue to form parallel surfaces of tissue, for surgical closure of the tissue.

According to some embodiments of the invention, further including additionally pulling the first tissue engaging component and the second tissue engaging component by rotating the first tissue engaging component and the second tissue engaging component.

According to some embodiments of the invention, moving the first tissue engaging component away from the second tissue engaging component includes releasing a spring which pushes the first tissue engaging component away from the second tissue engaging component.

According to some embodiments of the invention, the engaging the first tissue engaging component with tissue near the first location in the opening in tissue includes inserting a first prong into the opening in the tissue, and the engaging the second tissue engaging component with tissue near the second location in the opening includes inserting a second prong into the opening in the tissue.

According to some embodiments of the invention, further including stapling the tissue opening.

According to some embodiments of the invention, further including cutting excess tissue away from a suturing line.

According to some embodiments of the invention, the pulling the first tissue engaging component and the second tissue engaging component causes the edges of the opening in the tissue to be pulled toward the tissue stapler.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1B is a simplified illustration of an opening in tissue;

FIG. 1C is a simplified illustration of a prior art tissue retractor acting on an opening in tissue;

FIG. 1D is a simplified illustration of a device for drawing edges of a tissue opening toward each other for surgical attachment according to an example embodiment of the invention;

FIGS. 4B-4F are simplified illustrations of a device according to an example embodiment of the invention passing through a trocar;

Figure 10A:
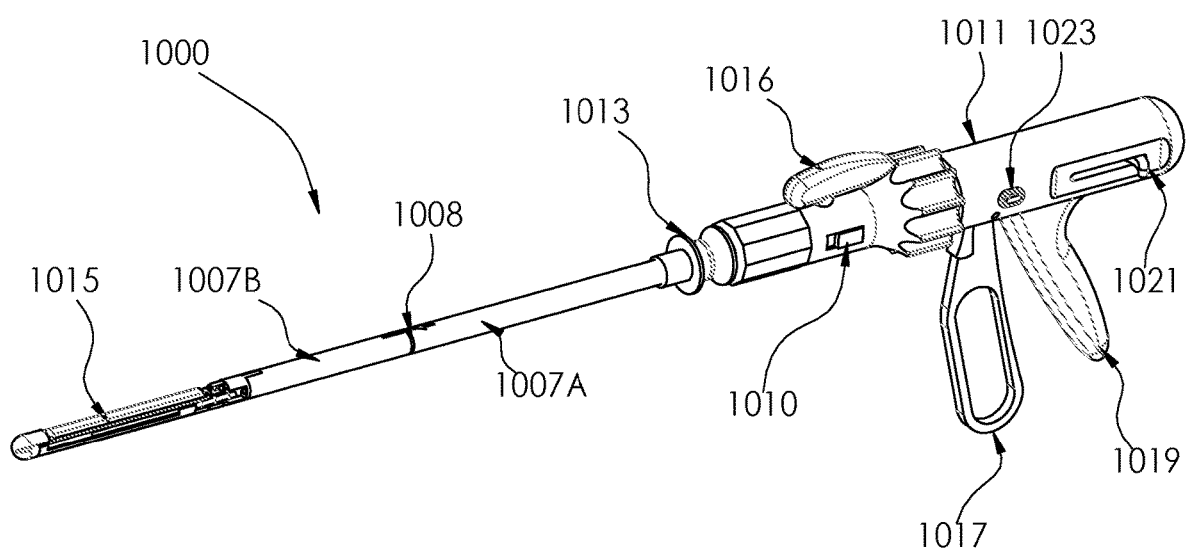
Figure 10B:
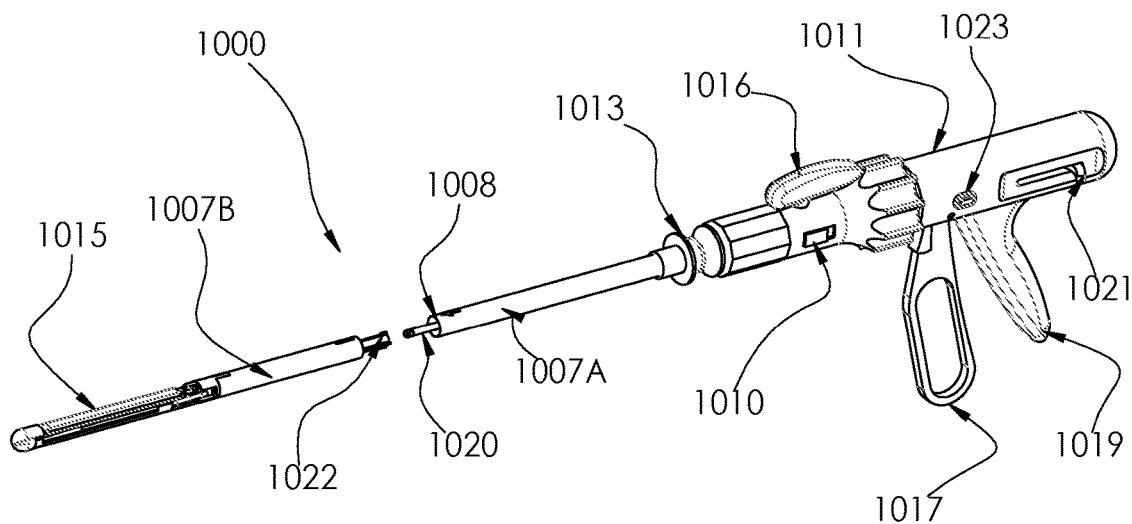
Figure 11A:
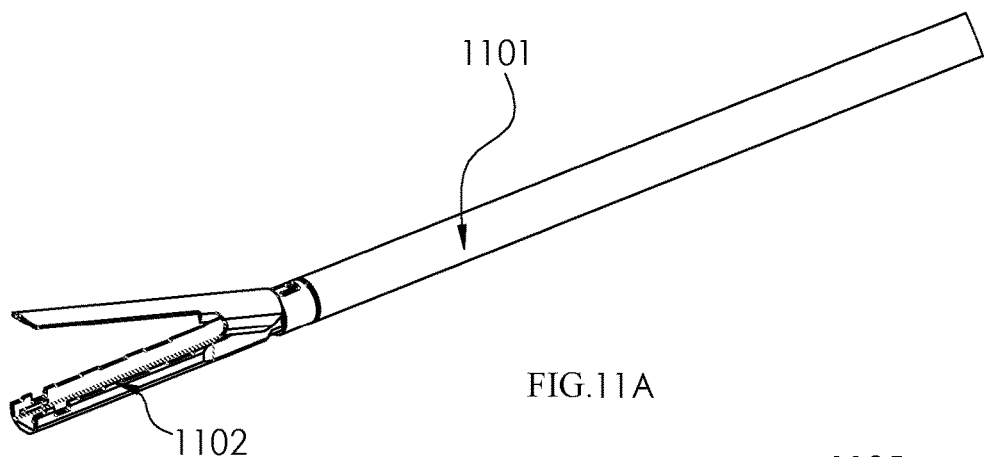
Figure 11B:
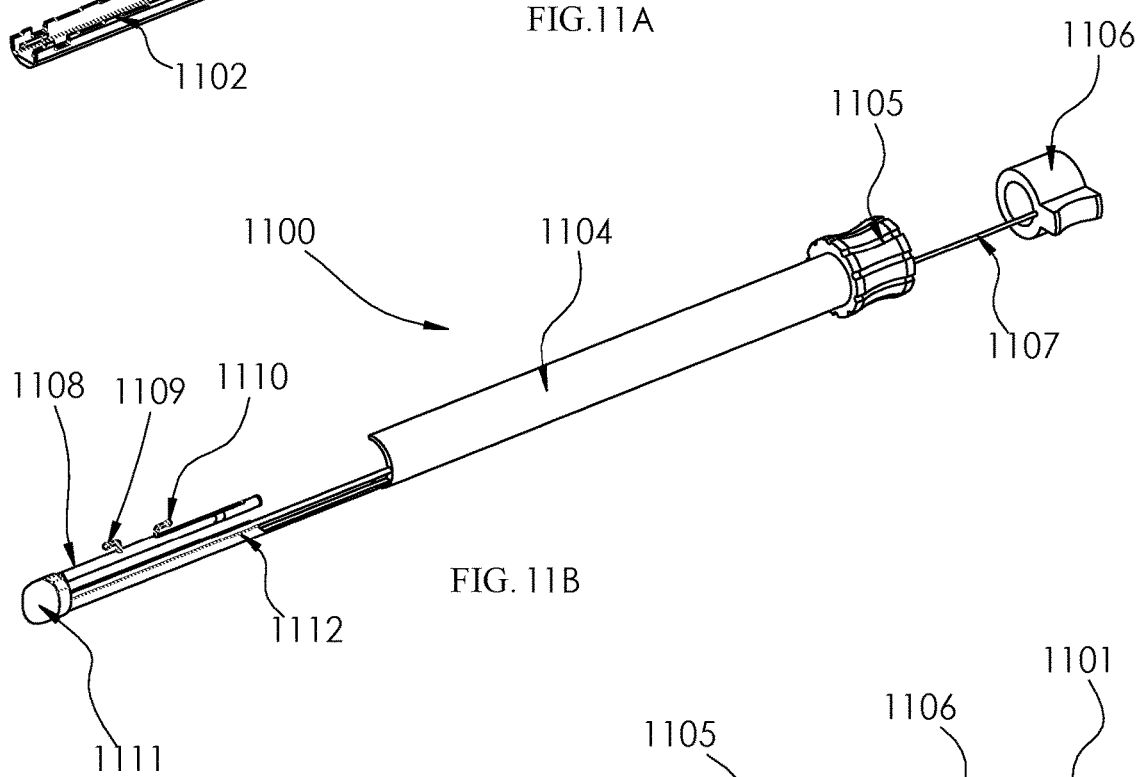
Figure 11C:
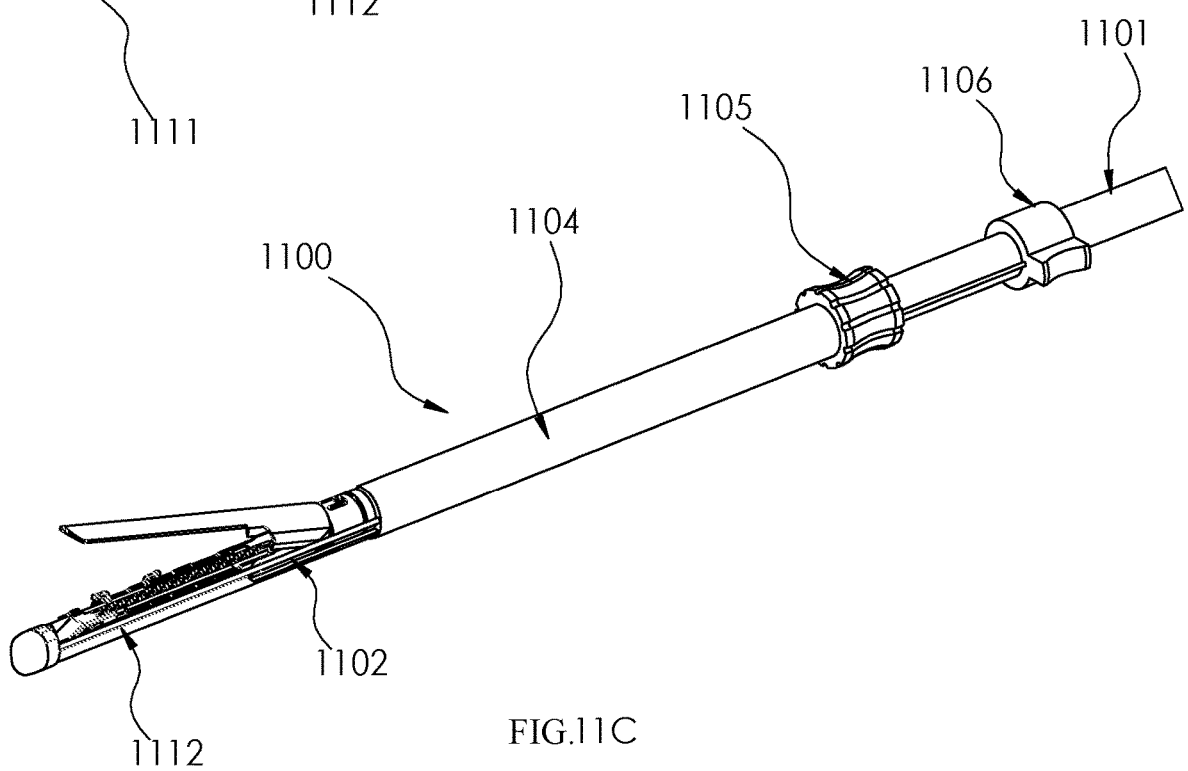
Figure 11G:
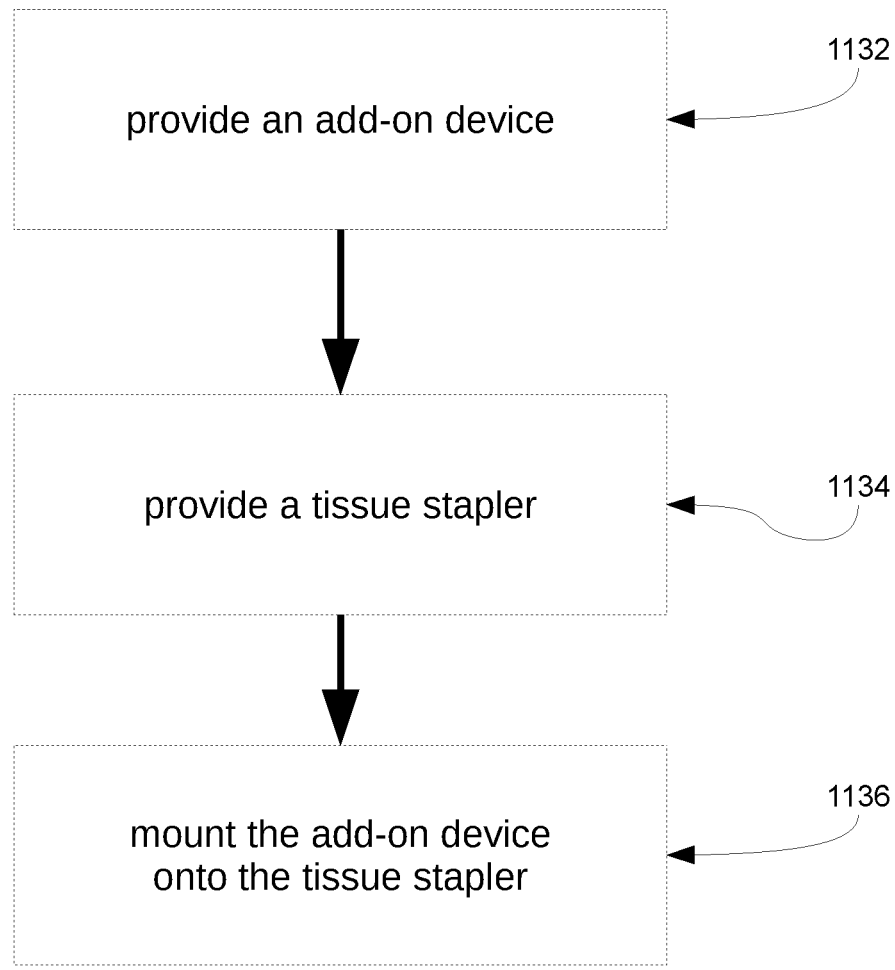
Figure 12A:
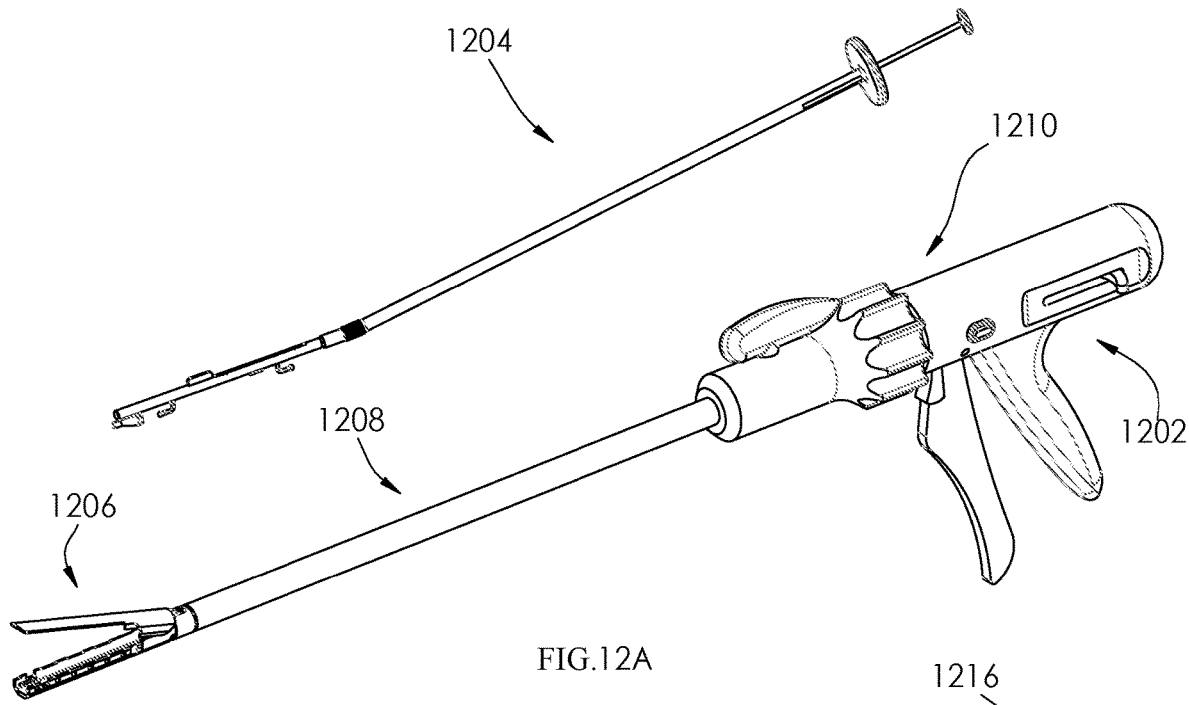
Figure 12B:
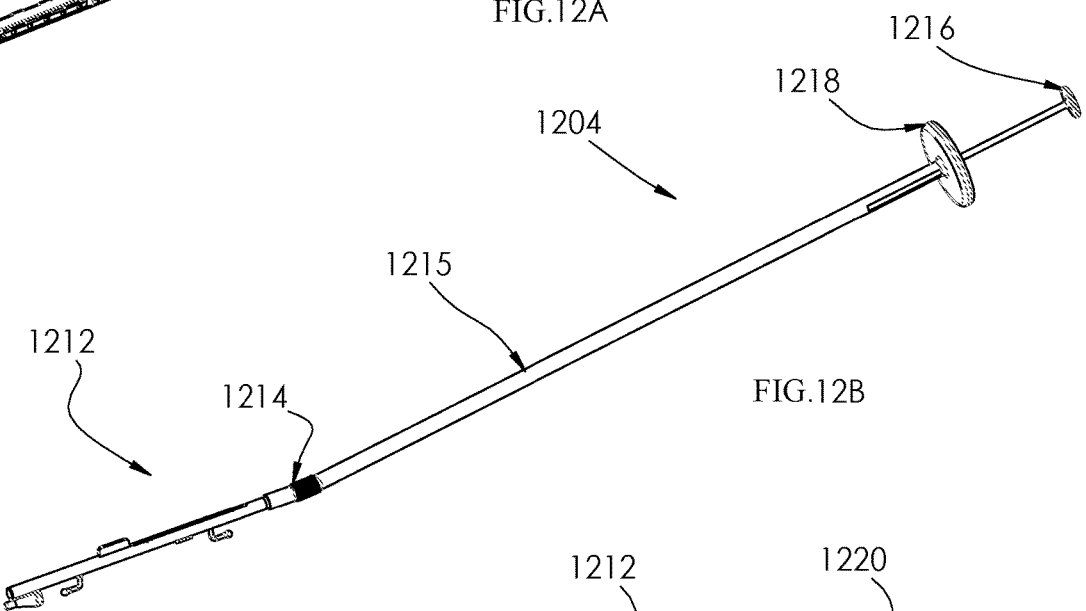
Figure 12C:
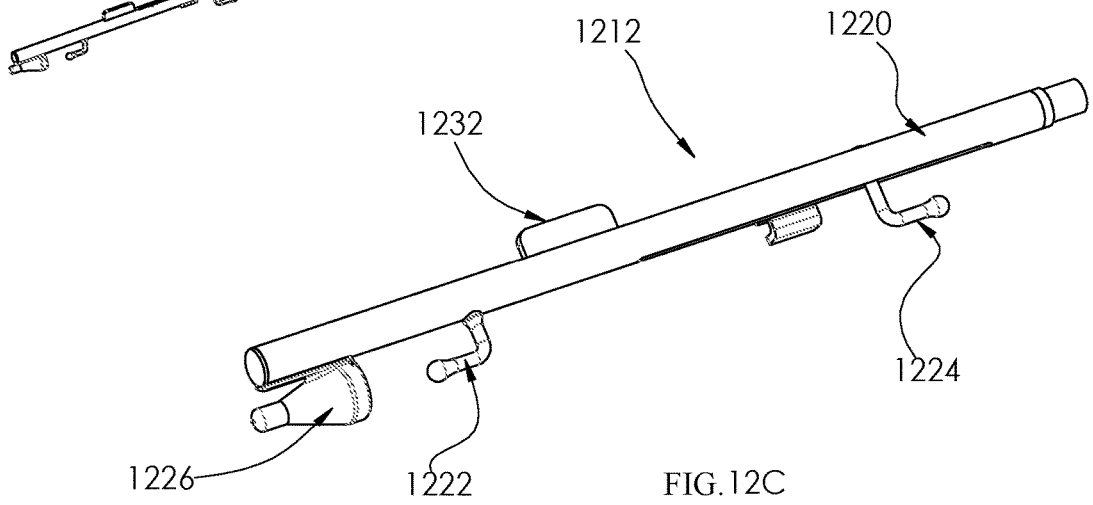
Figure 12D:
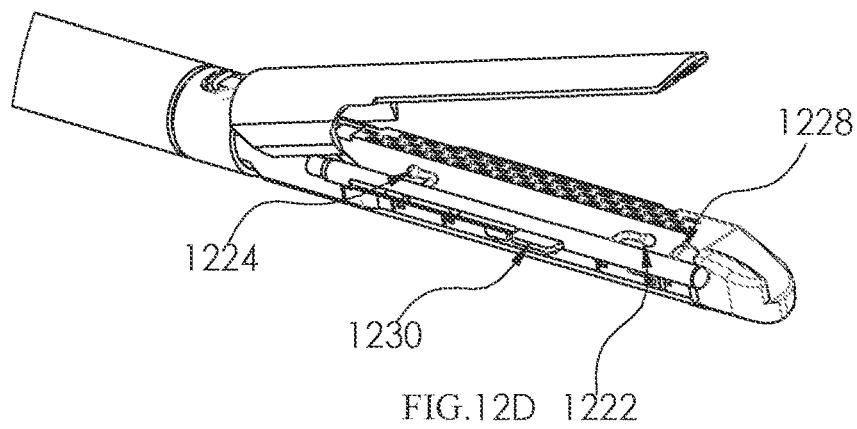
Figure 12E:
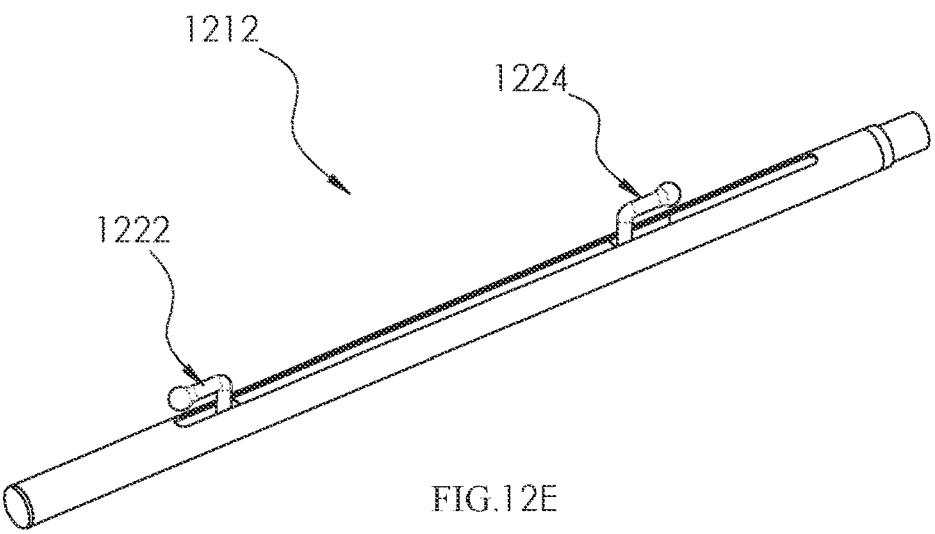
Figure 12F:
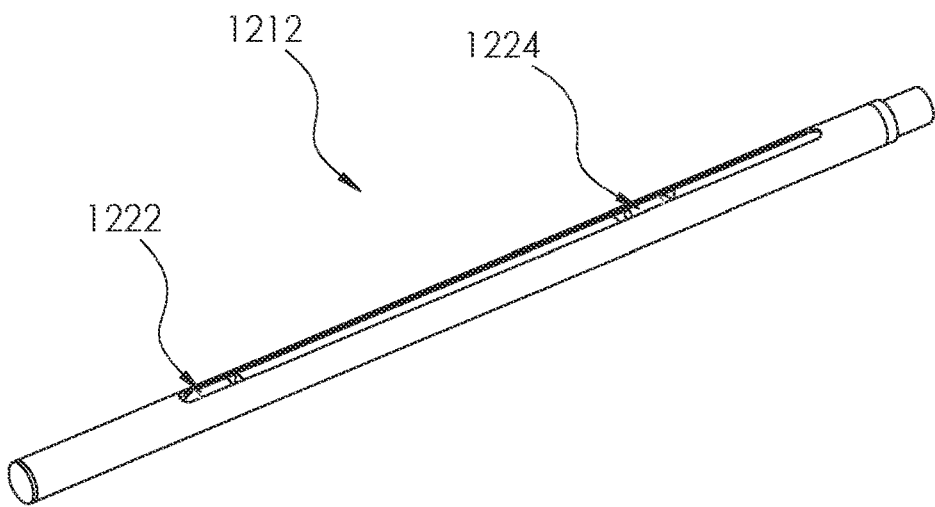
Figure 13:
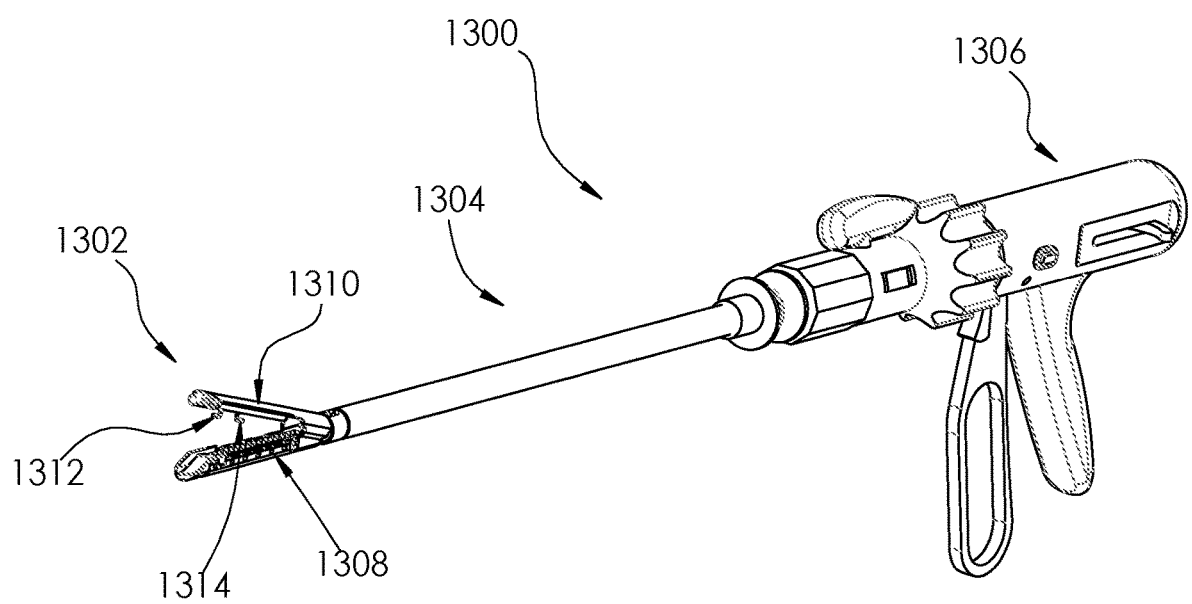

FIGS. 7A-C are simplified illustrations of a component for drawing edges of tissue opening toward each other according to an example embodiment of the invention;

FIGS. 7D-F are simplified illustrations of the component for drawing edges of tissue opening toward each other of FIGS. 7A-C according to an example embodiments of the invention;

FIGS. 8A-F are simplified illustrations of a component for drawing edges of tissue opening toward each other according to an example embodiment of the invention;

FIG. 9 is a simplified illustration of a component for drawing edges of tissue opening toward each other attached to a hinge according to an example embodiment of the invention;

FIGS. 10A and 10B are simplified illustrations of a device according to an example embodiment of the invention;

FIGS. 11A-11F are simplified illustrations of a device according to an example embodiment of the invention;

FIG. 11G is a simplified flow chart illustration of a method for constructing a device for laparoscopic surgical closure of an opening in tissue;

FIGS. 12A-12D are simplified illustrations of a system according to an example embodiment of the invention;

FIGS. 12E and 12F are simplified illustrations of optional features in an example embodiment of the invention; and FIG. 13 is a simplified illustration of a device according to an example embodiment of the invention.

DESCRIPTION OF SPECIFIC EMBODIMENTS OF THE INVENTION

The present invention, in some embodiments thereof, relates to devices and methods for aligning tissue for surgical attachment and optionally surgically attaching the tissue and, more particularly, but not exclusively, to laparoscopic devices and methods for the above.

Overview

According to an aspect of some embodiments there is provided a device for aligning tissue for surgical attachment.

In some embodiments the device is shaped to be inserted into an opening in tissue and to shape the opening, aligning edges of the tissue for surgically attaching to each other.

In some embodiments a device is used to facilitate laparoscopic closure of, by way of a non-limiting example, two pieces of intestine intracorporeally with an improved (optionally TA-like) stapling device. The device is optionally designed to be able to engage a common enterotomy opening of a side-to-side, functional end-to-end gastrointestinal anastomosis, bring the engaged opening into jaws of a stapling instrument (or bring the jaws of a stapling instrument to the engaged opening), optionally by rotating the engaged opening into the device, optionally close the device, and fire 2 or 3 rows of staples thereby closing the enterotomy without need for sutures or need to re-sect any extra intestine. It is noted that re-secting extra intestine could lead to narrowing of the intestine.

In some embodiments, the device includes two tissue engagement components which are inserted into the opening. In some embodiments, one or both of the tissue engagement components are prongs for engaging edges of the tissue opening. In some embodiments, one or both of the tissue engagement components are clamps for grabbing onto edges of the tissue opening.

A non-grabbing engagement of tissue edges, such as by prongs or recesses in the device, produces a non-fixed engagement, enabling the tissue engagement components to slide along the tissue edges (or the tissue edges to slide along the tissue engagement components), while engaging, or maintain contact with, the tissue edges. A grabbing engagement of tissue edges, such as by a clamp, produces a fixed engagement, fixing the tissue engagement component to the tissue at the location being clamped, until the tissue engagement component is released.

The term "tissue engagement" in all its grammatical forms is used throughout the present specification and claims to include both non-grabbing tissue engagement and grabbing tissue engagement.

The words "drawing" tissue in all their grammatical forms are used throughout the present specification and claims interchangeably with the words "approximating" tissue and their corresponding grammatical forms.

In some embodiments, the device includes two prongs which are inserted into the opening. In some embodiments, the device includes an elongate bent element with two recesses, each recess for catching an edge of the tissue opening. In some embodiments, the device includes an oval shape with two tips for catching edges of the tissue opening.

In some embodiments the prongs are thin, shaped to pass through an opening of tissue which the prongs then optionally re-shape to a narrow opening which is to be stapled and/or sutured. The thickness of the prongs optionally comes between edges of the tissue opening even after the opening is re-shaped as the narrow opening, so the prongs are meant to be thin, so as not to cause the re-shaped tissue opening to be wide. In some embodiments the thickness of the prongs is in a range between 0.5 millimeters and 5 millimeters.

By way of a contradicting example, surgical retractors are configured to stretch tissue apart, and tips of the retractors are shaped to contact/grab a substantial length of a tissue edge, for example 10, 20, 30 millimeters of tissue edge.

In some embodiments, tips or prongs of the aligning device are shaped to contact tissue edge perpendicular to an axis along a length of the tips, that is approximately a diameter of the tips. In some embodiments a diameter of the prongs or tips is in a range of 0.5 millimeters to 5 millimeters.

In some embodiments one prong is configured as a grabber, and grabs the tissue, while another prong is configured to slide along the edge of the tissue and also participate in shaping the tissue opening.

In some embodiments two prongs are configured to be non-grabbing, so as to slide along the edge of the tissue.

In some embodiments the two prongs are configured to move away from each other by force of an elastic actuator, by way of example by force of a spring.

In some embodiments the force of the spring is in a range between 10 and 50 grams force, or 10 grams to 200 grams, to 2 kilograms, even to 5 kilograms force.

In some embodiments the force of the spring is adjustable.

In some embodiments the device includes a maintainer component to keep the prongs from expanding until the maintainer is released.

In some embodiments the device is configured to stretch the tissue while aligning edges of the tissue. In some embodiments the device is configured to stretch the tissue by a specific amount, optionally by limiting an extent of movement of the tissue engagement components, such as the prongs, away from each other. In some embodiments the specific amount is measured by measuring a movement of a control for moving the tissue engagement components away from each other. In some embodiments the device is configured to stretch the tissue by a specific force, optionally by a spring with a specific force being used to stretch the tissue. In some embodiments the specific force is optionally measured by measuring a force acting upon the tissue engagement components.

In some embodiments the device is configured to allow suturing the aligned edges of the tissue.

In some embodiments the device is configured to align a tissue stapler appropriately along the aligned tissue edges.

In some embodiments the device includes a shape which allows the tissue stapler to close upon tissue, and optionally staple tissue, at an appropriate distance from aligned edges of the tissue. The device optionally includes the tissue engagement components being located at an appropriate distance from the edge of the tissue stapler.

In some embodiments the device includes a tissue stapler for optionally stapling the aligned edges of the tissue.

In some embodiments the device is configured to be operated laparoscopically.

In some embodiments the device is optionally configured so that the prongs are remotely operated, optionally by wire, optionally from outside a patient's body.

In some embodiments the device is optionally configured so that an associated stapler is remotely operated, optionally by wire, optionally from outside a patient's body.

According to an aspect of some embodiments there is provided a device for laparoscopically drawing edges of a tissue opening toward each other for surgical attachment.

In some embodiments the device is shaped to be inserted into a keyhole incision, and extend to a tissue opening such as a hole or opening or slit in tissue inside a patient's body, and shape the hole/opening/slit, aligning edges of the tissue for surgically attaching to each other.

In some embodiments, the device includes prongs for inserting into the tissue opening, and a spreader for optionally moving the prongs away from each other, to stretch the tissue opening into an elongated shape with tissue edges aligned parallel to each other.

In some embodiments the device includes a first portion configured to operate the device from outside a patient's body, and a second portion configured to include the prongs and operate inside the patient's body.

In some embodiments the device includes a spreader component for moving the prongs away from each other.

In some embodiments the spreader component is configured to be operated from outside the patient's body.

In some embodiments the spreader component includes a spring released by a control operated from outside the patient's body, the released spring moving the prongs away from each other.

In some embodiments the spring is included in the first portion of the device, outside the patient's body.

In some embodiments the spring is included in the second portion of the device, inside the patient's body.

In some embodiments the prongs are connected to wires controlled from outside the patient's body. In some embodiments moving the prongs away from each other includes pushing and/or pulling the wires.

In some embodiments the device includes a tissue stapler in the second portion of the device, configured to operate inside the patient's body.

In some embodiments the prongs and/or the spreader device are configured to lie between jaws of a tissue stapler.

In some embodiments the tissue stapler is configured to be operated from outside the patient's body.

In some embodiments the device is shaped and sized to pass through a trocar, a catheter, an endoscope.

In some embodiments the tissue stapler includes a blade for cutting excess tissue. In some embodiments the tissue stapler is a narrow tissue stapler without a blade.

In some embodiments the tissue stapler is a narrow tissue stapler, comprising no more than 3 rows of staples. In some embodiments the tissue stapler is a narrow tissue stapler, comprising only 2 rows of staples. In some embodiments the tissue stapler is a narrow tissue stapler, comprising only 1 row of staples.

According to an aspect of some embodiments there is provided a method for aligning tissue for surgical attachment, including inserting a device for aligning tissue for surgical attachment prongs into an opening in tissue, and moving the prongs away from each other, shaping the opening into an elongated opening causing edges of the tissue to move toward each other.

In some embodiments, after the prongs have engaged the tissue and formed the tissue opening into an elongated opening form, the prongs are optionally additionally pulled in a directional perpendicular to the direction of the elongated opening, pulling parallel edges of the tissue to form parallel surfaces of tissue, for attachment to each other by suturing and/or stapling. In some embodiments, the tissue opening is sutured shut.

In some embodiments, the tissue opening is stapled shut.

In some embodiments, the first prong is moved away from the second prong by a spring which pushes the first prong away from the second prong.

In some embodiments, a stapler is placed in contact with the first prong and the second prong in order to align the stapler for stapling the tissue.

In some embodiments, the device includes specific rests or stops for aligning the stapler relative to the device.

According to an aspect of some embodiments there is provided a method for laparoscopic surgical closure of an opening in tissue, including inserting a laparoscopic device for drawing edges of a tissue opening toward each other for surgical attachment through a keyhole incision in a patient's body, and using the device for drawing edges of a tissue opening toward each other.

In some embodiments the laparoscopic device includes prongs as descried above, and the prongs are inserted into an opening in tissue, and moved away from each other to cause edges of the tissue to move toward each other.

In some embodiments moving the prongs away from each other includes releasing a spring which pushes the prongs away from each other.

In some embodiments a spring release control is manipulated outside a patient's body to release the spring.

In some embodiments the tissue edges are sutured closed laparoscopically.

In some embodiments a laparoscopic stapler is placed in contact with the tissue and the tissue is optionally stapled shut, and optionally edges of the tissue may be cut away.

In some embodiments, the laparoscopic stapler is placed in contact with the device in order to align the stapler for stapling the tissue.

In some embodiments, the device includes specific rests or stops for aligning the laparoscopic stapler relative to the device.

In some embodiments the laparoscopic device includes a tissue stapler

Figure 1A:
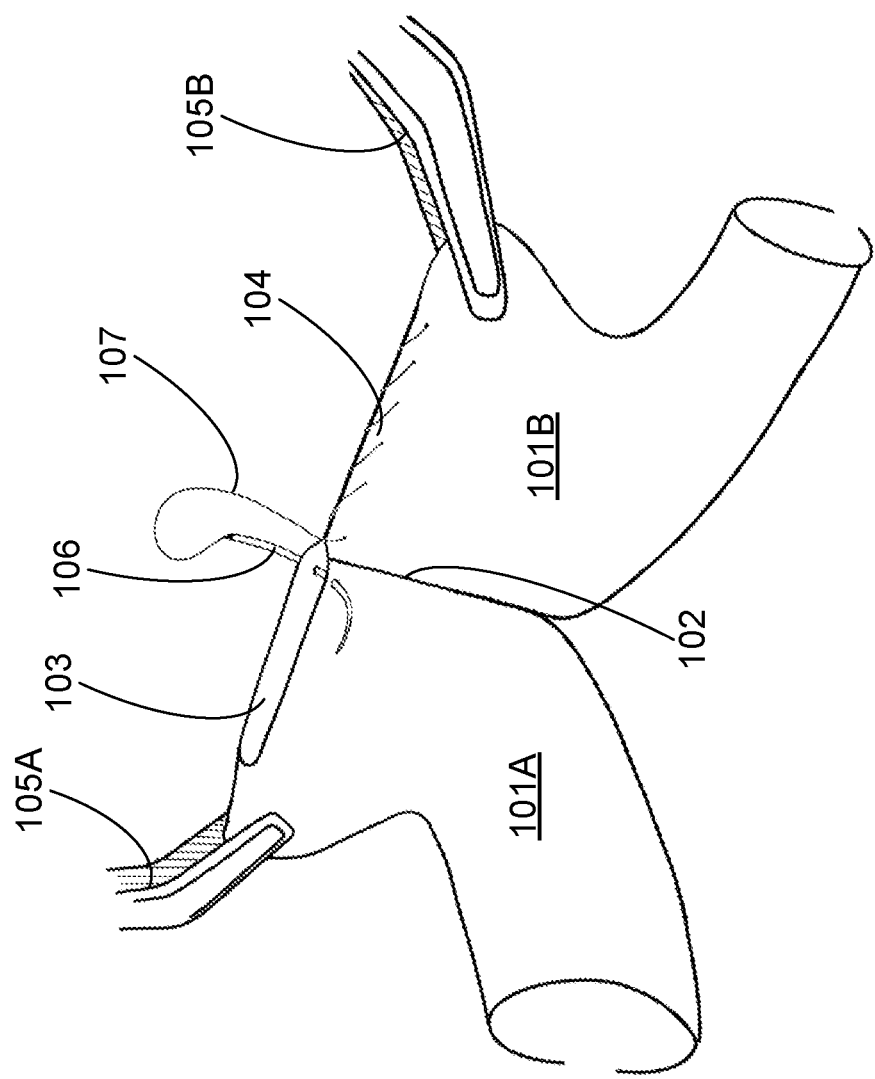
FIG. 1A is a simplified line drawing illustration of prior art suturing of intestines in an anastomosis procedure.

For purposes of better understanding some embodiments of the present invention, reference is first made to FIG. 1A, which is a simplified line drawing illustration of prior art suturing of intestines in an anastomosis procedure.

FIG. 1A shows two sections of intestine 101A 101B, already connected to each other along a line 102. Two forceps 105A 105B grasp the sections of the intestine 101A 101B and pull them apart, shaping an opening 103 in tissue to a shape of a narrow opening, and a needle 106 pulls thread 107 to suture 104 the opening 103 closed.

It is noted that using the example illustration of an anastomosis procedure is not intended to limit scope of embodiments of the invention. Various embodiments which use methods and/or devices as described herein include:
  gastric anastomosis;
  small bowel anastomosis;
  colon anastomosis;
  closing a vaginal cuff in a vaginal hysterectomy;
  closing a uterine incision in a C-Section; and
  closure of a hysterotomy in a Caesarian Section.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Reference is now made to FIG. 1B, which is a simplified illustration of an opening 111 in tissue.

FIG. 1B shows an opening in tissue, in order to show a starting point for describing use of a prior art device in FIG. 1C, and of an example embodiment in FIG. 1D.

Reference is now made to FIG. 1C, which is a simplified illustration of a prior art tissue retractor 113 acting on an opening 114 in tissue.

The tissue retractor 113 has two loop prongs 112A 112B for inserting into a tissue opening. When the loop prongs 112A 112B are moved away from each other, sides of the tissue opening 114 are drawn apart. In an extreme case if the loop prongs 112A 112B are moved away from each other to a maximal distance, the tissue opening 114 forms a shape of a rectangle, with a width 115 corresponding to a width of the loop prongs 112A 112B and a length 116 of the tissue opening 114 making up the rest of the circumference of the tissue opening 114.

Reference is now made to FIG. 1D, which is a simplified illustration of a device for drawing edges of a tissue opening toward each other for surgical attachment according to an example embodiment of the invention.

FIG. 1D shows a device 120 with two prongs 117A 117B for inserting into a tissue opening 118. When the prongs 117A 117B are moved away from each other, sides of the tissue opening 118 are drawn together. The tissue opening 118 forms a shape of a narrow opening, with a maximal width 122 corresponding to a diameter of the prongs 117A 117B and a length 116 of the tissue opening 118 half the circumference of the tissue opening 118 or longer, if the tissue opening 118 is stretched.

In some embodiments, the prongs 117A 117B are optionally moved away from each other exerting some force, and edges of the tissue opening 118 are optionally stretched. In such cases the edges of the tissue opening are drawn closer together, potentially touching each other.

In some embodiments, the prongs 117A 117B are optionally moved away from a line referenced as 121 in FIG. 1D, pulling on the tissue edges, and optionally causing the tissue edges to lie parallel to each other, ready for attaching to each other by suturing, stapling or use of adhesive.

Figure 2B:
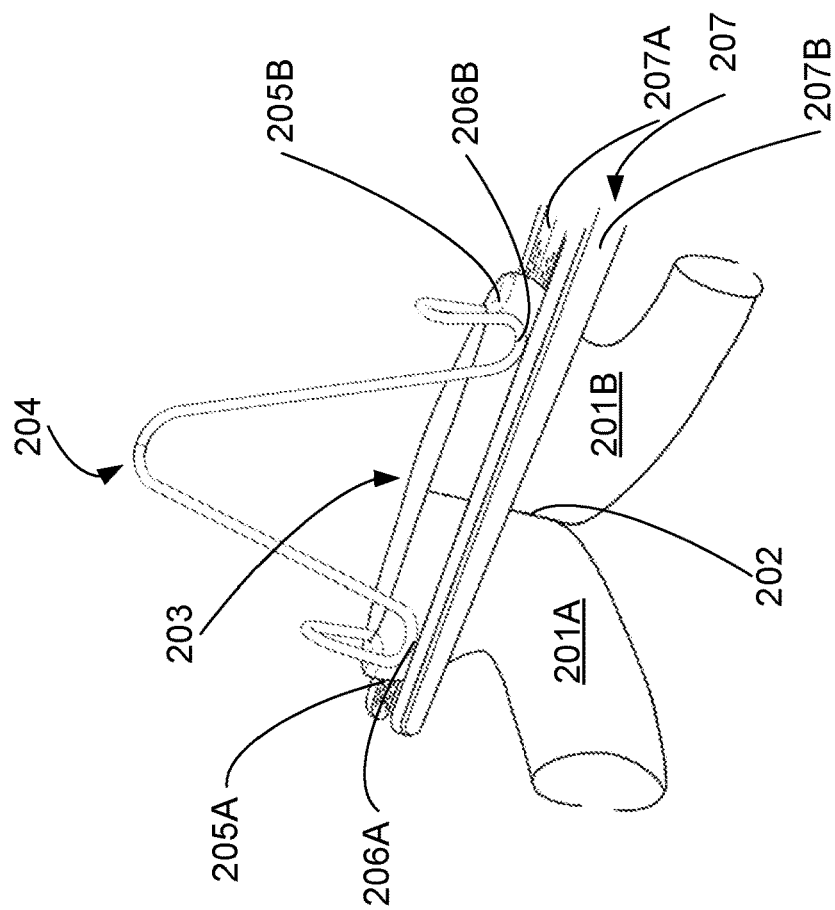
FIG. 2B is a simplified illustration of the device of FIG. 2A after its prongs have been moved away from each other according to an example embodiment of the invention.
Figure 2A:
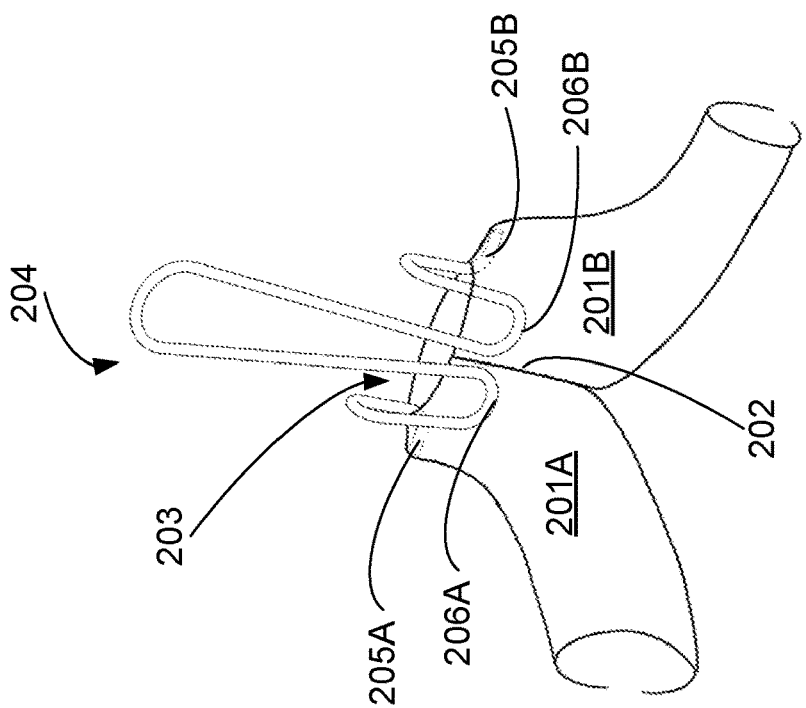
FIG. 2A is a simplified illustration of a device for drawing edges of a tissue opening toward each other for surgical attachment according to an example embodiment of the invention.

Reference is now made to FIG. 2A, which is a simplified illustration of a device for drawing edges of a tissue opening toward each other for surgical attachment according to an example embodiment of the invention.

FIG. 2A shows a device 204 being used for aligning tissue edges in an opening 203 in tissue during an example embodiment of a surgical anastomosis procedure. FIG. 2A shows two sections 201A 201B of intestine already attached to each other along a line 202, with the tissue opening 203 still open.

In some embodiments the example embodiment surgical procedure is an open stomach procedure. In some embodiments the example embodiment surgical procedure is a laparoscopic procedure, performed through one or more keyhole openings.

FIG. 2A shows the device 204 with two prongs 205A 205B, inserted into the tissue opening 203. The two prongs 205A 205B optionally each include a tip pointing away from each other, for insertion into the tissue opening 203.

In some embodiments the device 204 is shaped similarly to the Greek letter omega—Ω.

In some embodiments the device 204 is made of a flexible material such as, by way of some non-limiting examples: st.st wire, Nitinol and plastic.

In some embodiments a surgeon optionally approximates the two prongs 205A 205B together, optionally to a distance smaller than a Common Opening size, by way of a non-limiting example approximately 2 cm. In some embodiments the Common Opening size can be in a range of 10 millimeters to 10 centimeters in various embodiments the Common Opening length, and in some embodiments Common Opening diameter, can be in a range of 2 millimeters to 4 centimeters, and in some embodiments a tissue opening can be up to 30 centimeters. The surgeon optionally inserts the prongs 205A 205B into a hollow organ opening (Common Opening), and optionally releases the hooks. The device 204 springs back, optionally up to its original size, while stretching and aligning the Common Opening edges. The Common Opening is then ready for closure.

In some embodiments the Common Opening starts as an amorphous shape and becomes 2-dimensional and therefore more convenient for closing by an external device like a surgical stapler, or by conventional suturing.

In some embodiments stapler jaws are optionally placed at an appropriate location, not too far from the Common Opening edges. In some embodiments the device includes dedicated stoppers, in some embodiments part of the device wire, to indicate the stapler jaws location and/or locate the stapler jaws.

In some embodiments a wire is shaped with specific curvature to enable free working space for suturing.

In some embodiments the prongs can be part of the wire itself, optionally bent at an angle of 90 degrees or less. In some embodiments roughness is optionally added to a surface of the device and/or to the prongs to avoid slipping.

In some embodiments the device 204 optionally includes a tweezers and/or pincer shape.

In some embodiments the device 204 optionally includes one or more tissue graspers such as forceps.

Reference is now additionally made to FIG. 2B, which is a simplified illustration of the device of FIG. 2A after its prongs have been moved away from each other according to an example embodiment of the invention.

FIG. 2B shows the tissue opening 203 formed into a shape of an elongate narrow opening, by the two prongs 205A 205B having been moved away from each other.

The elongate shape of the tissue opening 203 is ready for attachment of edges of the tissue to each other.

In some embodiments the attachment of the edges of the tissue opening 203 to each other is optionally by sutured to each other. In some embodiments the attachment of the edges of the tissue opening 203 to each other is optionally by using adhesive to attach the edges to each other. In some embodiments the attachment of the edges of the tissue opening 203 to each other is optionally by stapling to each other.

FIG. 2B shows a stapler 207 placed along the edges of the tissue opening 203, optionally parallel to the edges of the tissue opening 203.

In some embodiments the device 204 includes rests or extensions 206A 206B for optional use in aligning the stapler 207 to the edges of the tissue opening 203.

In some embodiments the device 204 is configured so that the tips of the prongs 206A 206B extend further than the alignment extensions 206A 206B by a specific distance. In some embodiments the specific distance is used to control a distance between a line of stapling and edges of the tissue opening 203. In some embodiments the specific distance is optionally in a range between 1 millimeter and 10 millimeters, a range between 1 millimeter and 100 millimeters, a range between 1 millimeters and 1000 millimeters.

Figure 2C:
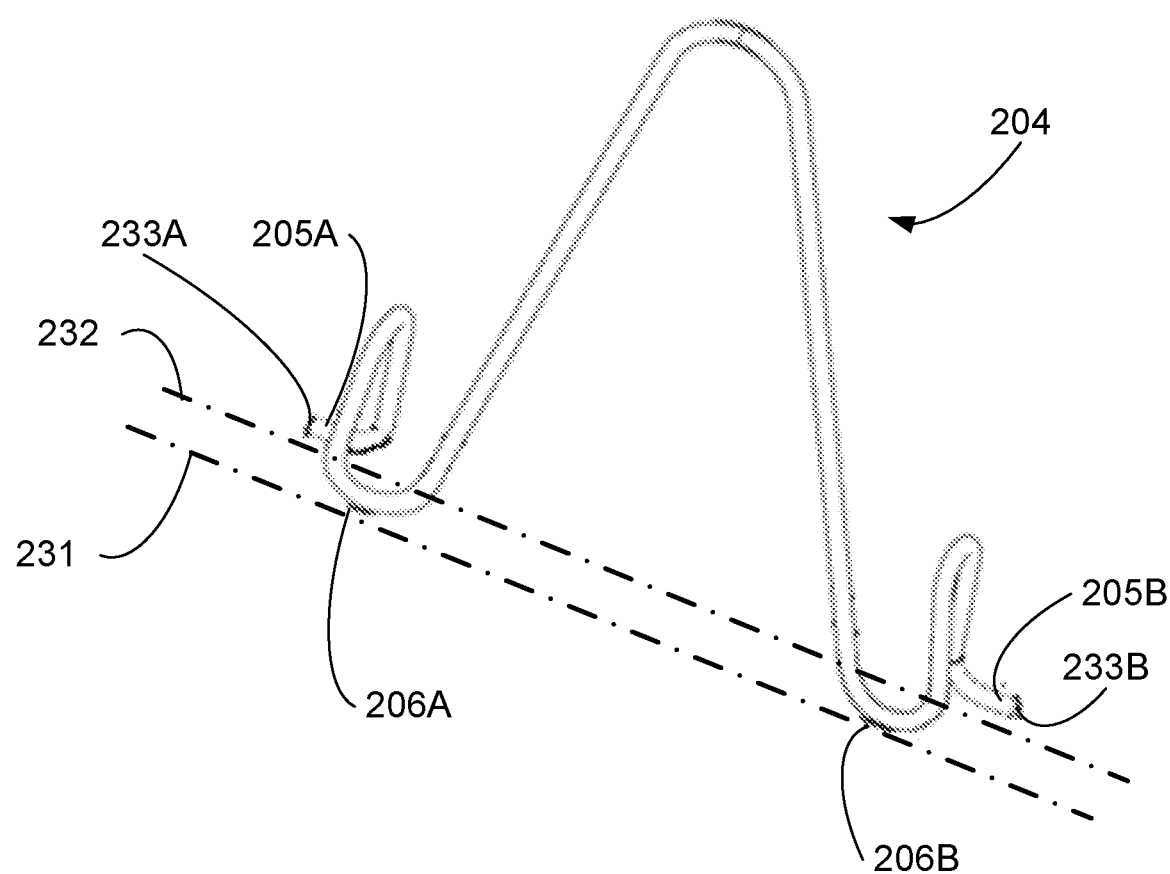
FIG. 2C is an enlarged illustration of the device of FIG. 2A according to an example embodiment of the invention.

Reference is now additionally made to FIG. 2C, which is an enlarged illustration of the device of FIG. 2A according to an example embodiment of the invention.

FIG. 2C shows the device 204 outside of a tissue opening, so that some of its parts may be described in more detail.

FIG. 2C shows the device 204 with the two prongs 205A 205B and the two alignment extensions 206A 206B.

A first line 232 is shown at a level of the two prongs 205A 205B.

A second line 231 is shown at a level of the two alignment extensions 206A 206B.

As described above, in some embodiments the first line 232 is optionally at a same level as the second line 231, in some embodiments the first line 232 is optionally above the level of the second line 231, in some embodiments the first line 232 is optionally below the level of the second line 231.

In some embodiments the material of the two prongs 205A 205B is optionally processed to be smooth, so that the two prongs 205A 205B may slide along a tissue edge.

In some embodiments the material of the two prongs 205A 205B is optionally roughened so that the two prongs 205A 205B may adhere to a tissue edge and refrain from sliding.

The very tips 233A 233B of the two prongs 205A 205B are shown.

In some embodiments the tips 233A 233B are optionally rounded, so as not to penetrate tissue.

In some embodiments the tips 233A 233B are optionally sharp, so as to penetrate tissue.

Figure 2D:
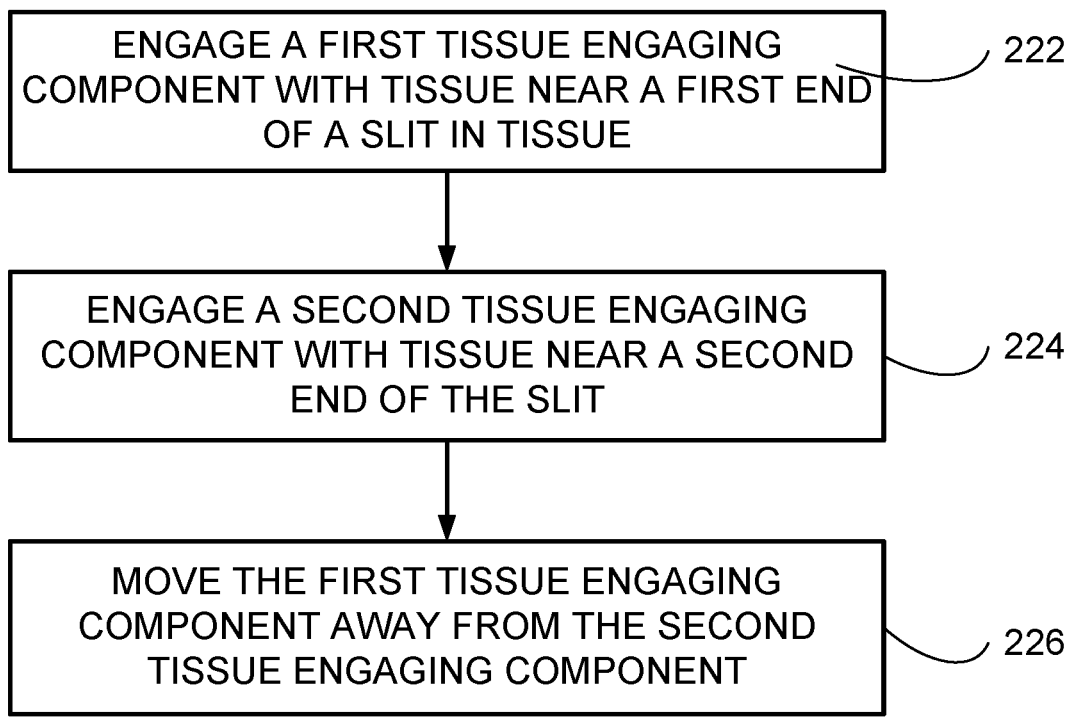
FIG. 2D is a simplified flow chart illustration of a method for drawing edges of a tissue opening toward each other for surgical closure of the tissue opening according to an example embodiment of the invention.

Reference is now made to FIG. 2D, which is a simplified flow chart illustration of a method for drawing edges of a tissue opening toward each other for surgical closure of the tissue opening according to an example embodiment of the invention.

The example method illustrated by FIG. 2D includes:
  engaging a first tissue engaging component with tissue near a first end of a slit in tissue (222);
  engaging a second tissue engaging component with tissue near a second end of the slit (224); and
  moving the first tissue engaging component away from the second tissue engaging component (226),
  thereby shaping the tissue opening into an elongated opening form.

In some embodiments the slit is an opening in tissue, not necessarily slit-shaped.

In some embodiments, the first tissue engaging component and the second tissue engaging component are optionally pulled in a directional perpendicular to a direction of the elongated opening, thereby pulling edges of the tissue to form parallel surfaces of tissue, for surgical closure of the tissue opening.

In some embodiments the first tissue engaging component and the second tissue engaging component are optionally moved toward the tissue edges, optionally locating an optional tissue stapler at a correct location for stapling the tissue edges closed.

In some embodiments, moving the first tissue engaging component away from the second tissue engaging component is optionally done by releasing a spring which pushes the first tissue engaging component away from the second tissue engaging component.

In some embodiments the tissue opening is sutured closed.

In some embodiments excess tissue is cut away from a suturing line.

In some embodiments a stapler is placed in contact with the first tissue engaging component and the second tissue engaging component.

In some embodiments the stapler is placed in contact with stapler support locations on the first tissue engaging component and the second tissue engaging component.

In some embodiments the tissue opening is stapled closed.

In some embodiments the first tissue engaging component is configured as a first prong. In some embodiments the second tissue engaging component is configured as a second prong.

In some embodiments the first tissue engaging component is configured as a first tissue grasper. In some embodiments the second tissue engaging component is configured as a second tissue grasper.

Figure 3B:
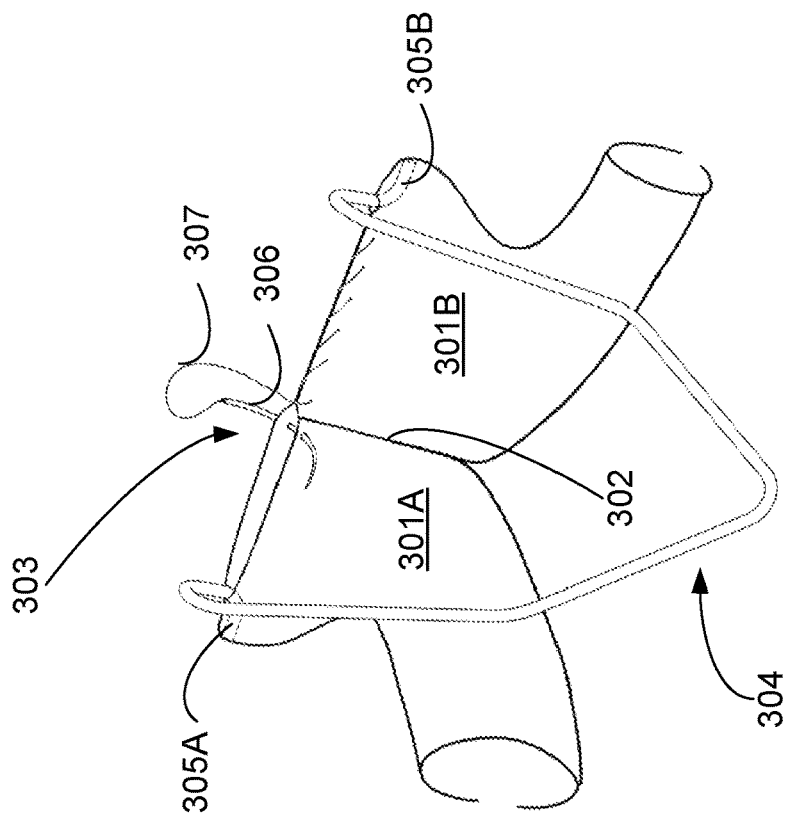
FIG. 3B is a simplified illustration of the device of FIG. 3A after its prongs have been moved away from each other according to an example embodiment of the invention.
Figure 3A:
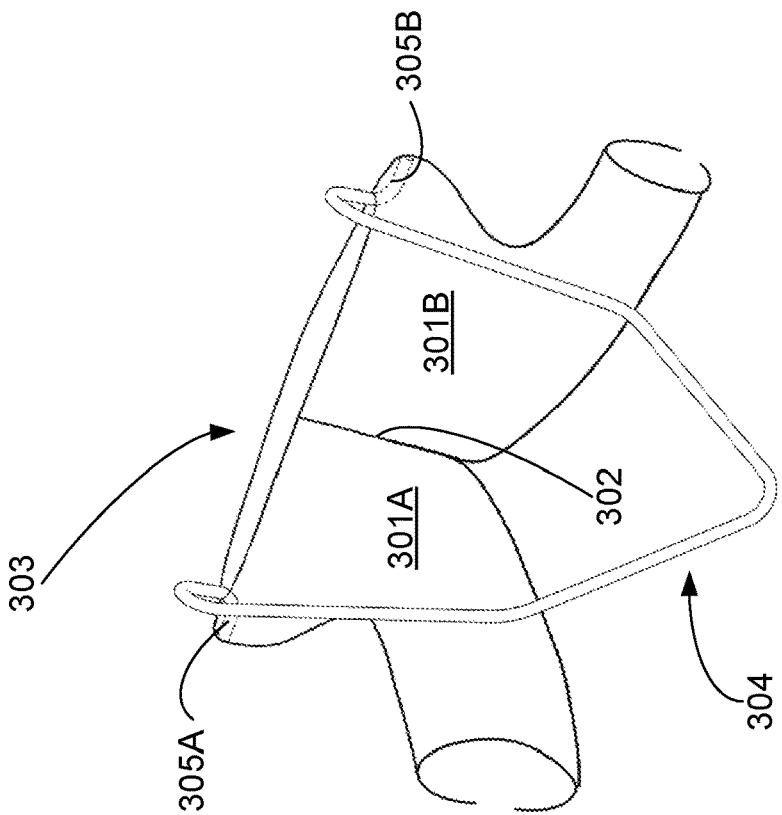
FIG. 3A is a simplified illustration of a device for drawing edges of a tissue opening toward each other for surgical attachment according to an example embodiment of the invention.

Reference is now made to FIG. 3A, which is a simplified illustration of a device for drawing edges of a tissue opening toward each other for surgical attachment according to an example embodiment of the invention.

FIG. 3A shows a device 304 being used for aligning tissue edges in an opening 303 in tissue during an example embodiment of a surgical anastomosis procedure. FIG. 3A shows two sections 301A 301B of intestine already attached to each other along a line 302, with the tissue opening 303 still open, and after its prongs have been moved away from each other, pulling edges of the tissue opening toward each other.

In some embodiments the example embodiment surgical procedure is an open stomach procedure. In some embodiments the example embodiment surgical procedure is a laparoscopic procedure, performed through one or more keyhole openings.

FIG. 3A shows the device 304 with two prongs 305A 305B, inserted into the tissue opening 303. The two prongs 305A 305B optionally each include a tip pointing away from each other, for insertion into the tissue opening 303.

Reference is now additionally made to FIG. 3B, which is a simplified illustration of the device of FIG. 3A after its prongs have been moved away from each other according to an example embodiment of the invention.

FIG. 3B shows the tissue opening 303 formed into a shape of an elongate narrow opening, by the two prongs 305A 305B having been moved away from each other, and the tissue opening being sutured closed.

The elongate shape of the tissue opening 303 is ready for attachment of edges of the tissue to each other.

In some embodiments the attachment of the edges of the tissue opening 303 to each other is optionally by sutured to each other. In some embodiments the attachment of the edges of the tissue opening 303 to each other is optionally by using adhesive to attach the edges to each other. In some embodiments the attachment of the edges of the tissue opening 303 to each other is optionally by stapling to each other.

FIG. 3B shows a needle 306 and thread 307 used for optionally suturing the tissue opening 303.

In some embodiments the device is suitable for use in laparoscopic surgery. The device is optionally shaped and/or sized, and/or made flexible, to enable the device to be inserted through a laparoscopic delivery device. In some embodiments the device is optionally bent to fit within the laparoscopic delivery device.

In some embodiments the device fits within a delivery device with a diameter of 5 mm. In some embodiments the device fits within a delivery device with a diameter in a range of 2 millimeters to 5, 10, 15, 20, 25 millimeters, In some embodiments the device is optionally pushed outside a cannula of a laparoscopic delivery device using an external pusher, and prongs of the device are optionally placed inside the Common Opening.

In some embodiments, after closuring is performed, the device is pulled outside the body through a conventional trocar using a grasper.

Figure 3C:
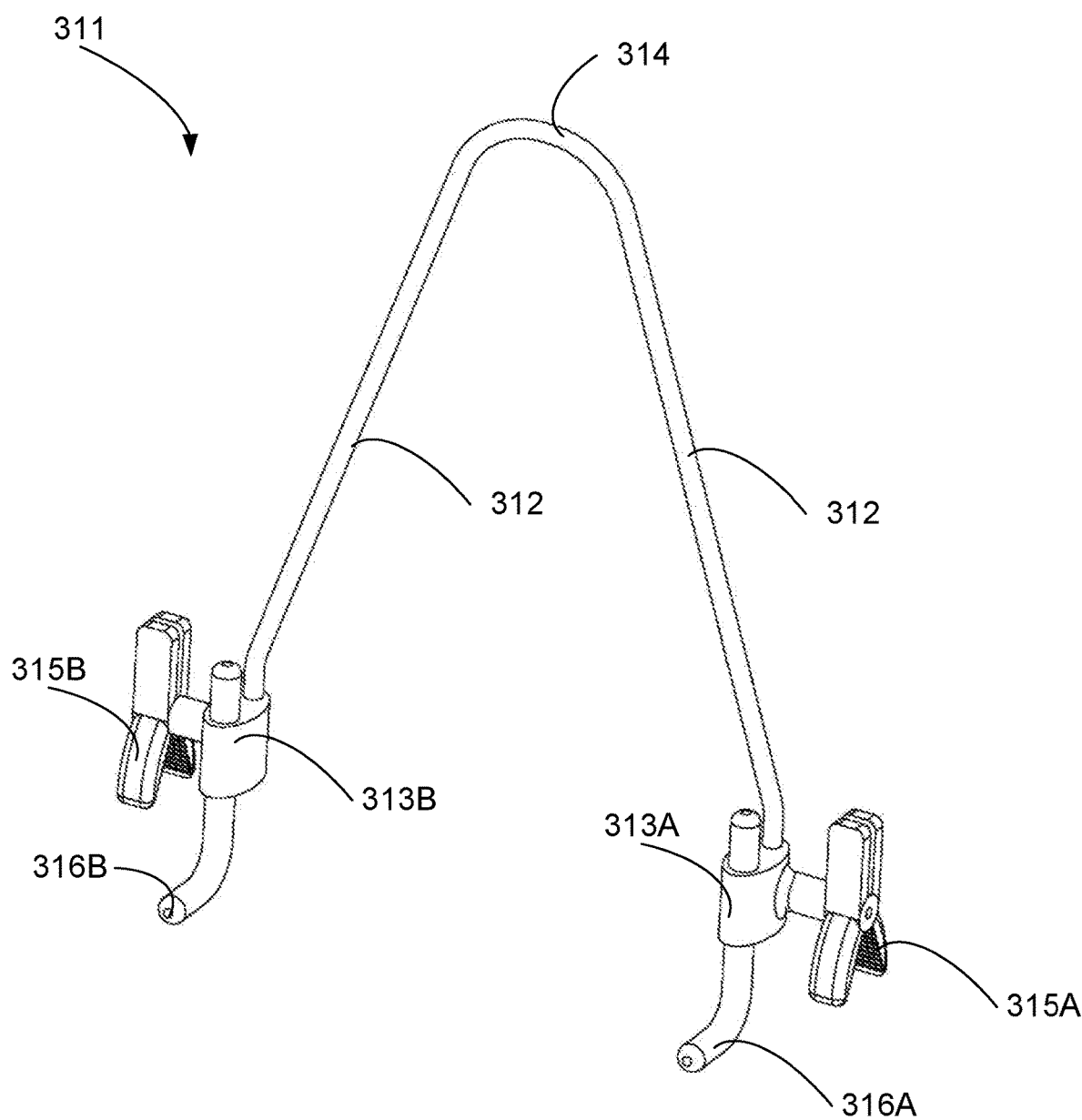
FIG. 3C is a simplified illustration of a device for drawing edges of a tissue opening toward each other for surgical attachment according to an example embodiment of the invention.

Reference is now made to FIG. 3C, which is a simplified illustration of a device for drawing edges of a tissue opening toward each other for surgical attachment according to an example embodiment of the invention.

FIG. 3C shows a device 311 with a handle 312 and two tissue engagement components 315A 315B for inserting into a tissue opening.

In some embodiments, the tissue engagement components 315A 315B are attached to the handle 312 by connecting components 313A 313B.

In some embodiments the tissue engagement components 315A 315B may optionally be tissue graspers or clamps.

When the tissue engagement components 315A 315B engage tissue and are moved away from each other, sides of the tissue opening are drawn together. The tissue opening is shaped into a shape of a narrow opening, with a length of the tissue opening of half a circumference of the tissue opening or longer, when the tissue edges are optionally stretched.

In some embodiments, the tissue engagement components 315A 315B are optionally moved away from each other exerting some force, and edges of the tissue opening are optionally stretched.

In some embodiments, the tissue engagement components 315A 315B are optionally moved away from the tissue, pulling on the tissue edges, and optionally causing the tissue edges to lie parallel to each other, ready for attaching to each other by suturing, stapling or use of adhesive.

In some embodiments the tissue engaging components 315A 315B are optionally normally open. In some embodiments the tissue engaging components 315A 315B are optionally normally closed.

In some embodiments, the device 311 further includes rests 316A 316B for optionally locating a tissue stapler at a desired location for stapling tissue edges closed.

In some embodiments, the rests 316A 316B are part of the handle 312. In some embodiments the rests 316A 316B are optionally attached to the handle 312 by connectors, optionally adjustable connectors, such as the connectors 313A 313B shown in FIG. 3C.

In some embodiments a bottom of the rests 316A 316B is optionally located at a same line as bottoms of the tissue engagement components 315A 315B so as to align the tissue stapler correctly.

In some embodiments the bottom of the rests 316A 316B is optionally located above or below the line of the bottoms of the tissue engagement components 315A 315B so as to align the tissue stapler correctly.

In some embodiments a location of the bottom of the rests 316A 316B is adjustable, in order to align the tissue stapler correctly.

In some embodiments the handle 312 is flexible and/or springy.

In some embodiments the handle 312 is made of wire.

In some embodiments the handle 312 the handle includes a spring exerting force to pull the tissue engagement components 315A 315B away from each other. In some embodiment the spring (not shown in FIG. 3C) is optionally located at a bend 314 of the handle 312.

Figure 4A:
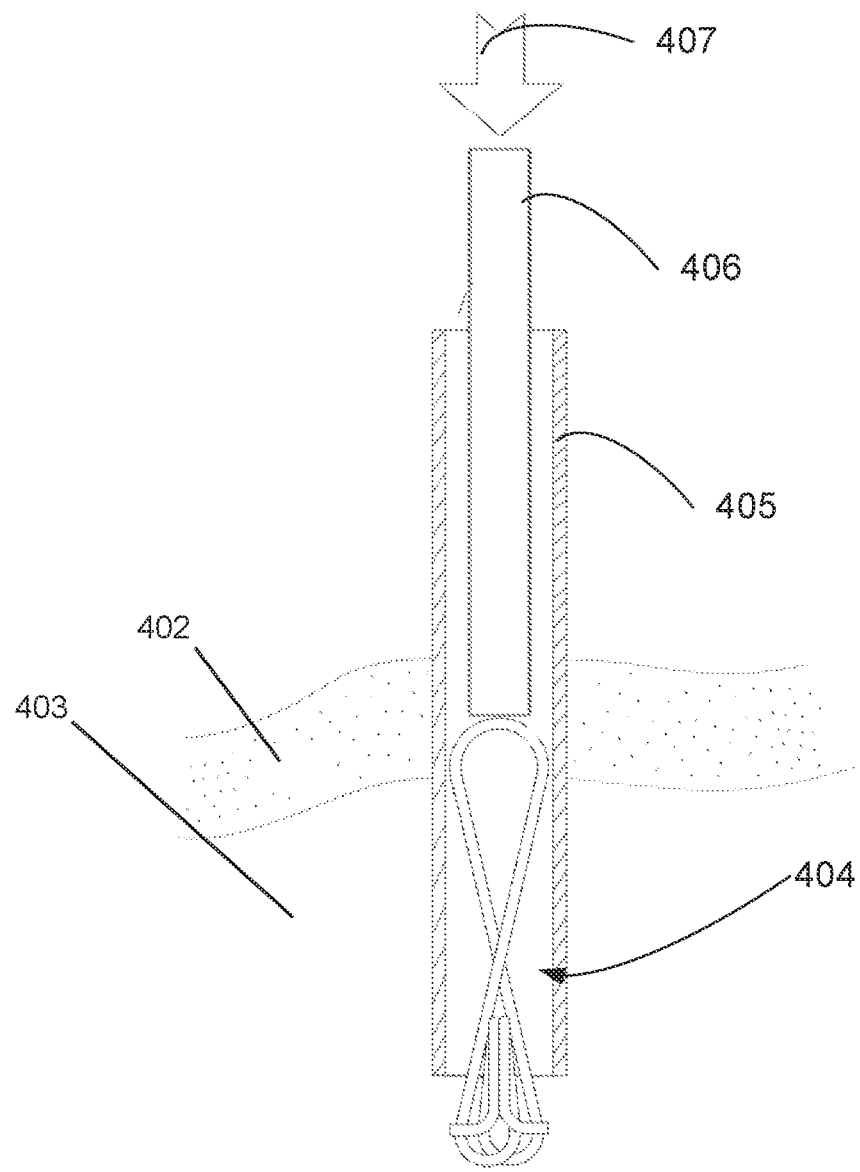
FIG. 4A is a simplified illustration of a device according to an example embodiment of the invention passing via a trocar into a patient's body.

Reference is now made to FIG. 4A, which is a simplified illustration of a device according to an example embodiment of the invention passing via a trocar into a patient's body.

FIG. 4A shows a device 404 optionally compressed into a shape which can pass through a trocar 405. The trocar is shown inserted through a patient's skin 402 and into the patient's body 403.

FIG. 4A also shows a pusher 406 pushing 407 the device 404 into the patient's body. In some embodiments the pusher 406 is optionally a grasper. In some embodiments the pusher 406 is optionally a dedicated component having a shaft for going through the trocar 405 and controlling the device 404, by way of a non-limiting example controlling opening and/or closing the device 404.

The device 404 of FIG. 4A is optionally a device according to an embodiment of the invention, such as, by way of some non-limiting examples: the device 120 of FIG. 1D, the device 204 of FIGS. 2A and 2B, the device 304 of FIGS. 3A and 3B, and the device 311 of FIG. 3C.

Reference is now made to FIGS. 4B-4F, which are simplified illustrations of a device according to an example embodiment of the invention.

FIGS. 4B-4F show an example embodiment of a device 414, a trocar 415 and a device controller 416 for pushing the device 414 through the trocar 415.

In some embodiments the drawing element which is named the trocar 415 is intended to portray a sheath 415. Where the description of FIGS. 4B-4F describes a trocar 415, a description of these embodiments are intended to describe the sheath 415.

FIG. 4B shows the device 414 completely within the trocar 415, optionally compressed into a shape which can pass through the trocar 415.

FIG. 4C shows the device 414 partly out of the trocar 415. In some embodiments the device 414 starts to expand when its tips 418 or prongs 418 are outside the trocar 415. In some embodiments the tips/prongs 418 start to spread apart outside the trocar 415. In some embodiments, when the tips/prongs 418 are outside the trocar 415 they are inserted into a tissue opening.

FIG. 4D shows the device 414 further out of the trocar 415. The tips/prongs 418 spread apart even more than shown in FIG. 4C. In some embodiments, the tips/prongs 418 are now inserted into a tissue opening. In some embodiments, if the tips/prongs 418 have previously been inserted into a tissue opening, the tips/prongs 418 now pull the tissue opening and start aligning the tissue opening into a straight line.

FIG. 4E shows the device 414 completely outside the trocar 415.

FIG. 4E shows the tips/prongs 418 spread even further apart. In some embodiments the tips/prongs 418 may be pulling the tissue edges into a straight line. In some embodiments the tips/prongs 418 may be stretching the tissue.

In some embodiments the device 414 is optionally attached to the device controller 416 by a connector 417.

In some embodiments the connector 417 is optionally controllable to detach the device 414 from the device controller 416.

FIG. 4F shows the device 414 detached from the device controller 416.

In some embodiments, if it is desired to pull the device 414 back through the trocar 415, the device controller 416 reattaches to the device 414. In some embodiments, if it is desired to pull the device 414 back through the trocar 415, a grasper (not shown) may optionally be inserted through the trocar, grasp the device 414, and pull the device 414 back through the trocar 415.

Figure 5A:
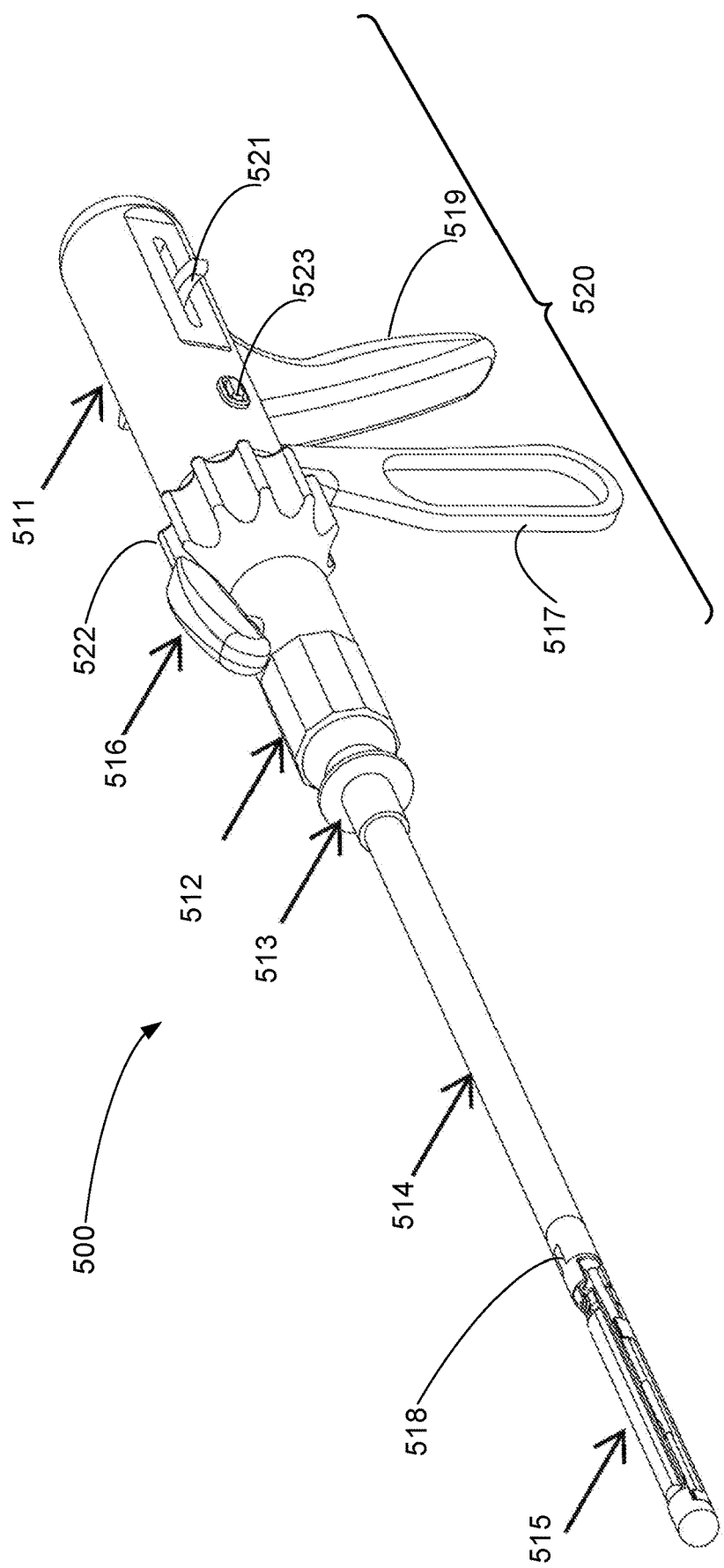
FIG. 5A is a simplified illustration of a device according to an example embodiment of the invention.

Reference is now made to FIG. 5A, which is a simplified illustration of a device according to an example embodiment of the invention.

FIG. 5A shows a device 500 configured to be inserted into a patient's body though a keyhole opening, optionally through a trocar.

The example device 500 includes:
 a component 515 for drawing edges of tissue opening toward each other for laparoscopic surgical closure;
 an optional hinge 518 for optionally changing an angle of the component 515 relative to a shaft 514;
 an optional control 513 for optionally moving tissue engagement components (not referenced in FIG. 5A) of the component 515 toward or away from each other;
 an optional control 512 for optionally rotating tissue engagement components relative to the shaft 514 and/or relative to an optional tissue stapler optionally included in the component 515;
 an optional control 516 for optionally controlling the optional hinge 518;
 an optional trigger 517 to optionally operate the above-mentioned optional tissue stapler to insert staples into tissue, and/or optionally operate an optional tissue cutter (not referenced in FIG. 5A);
 an optional control 521 to optionally open an optional staples cartridge/anvil and/or withdraw a tissue cutter backwards after firing;
 an optional grip 519 for grasping the device 500; and
 an optional handle 511 for containing the controls.
 an optional dial control 522 to optionally rotate the shaft 514 relative to the handle 511

FIG. 5A also shows a first portion 520 of the device 500, the first portion 520 configured for operating the device 500 from outside a patient's body.

In some embodiments the optional trigger 517 optionally closes a tissue stapler anvil and/or shoots staples, optionally when an optional safety 523 has been disengaged.

Figure 5B:
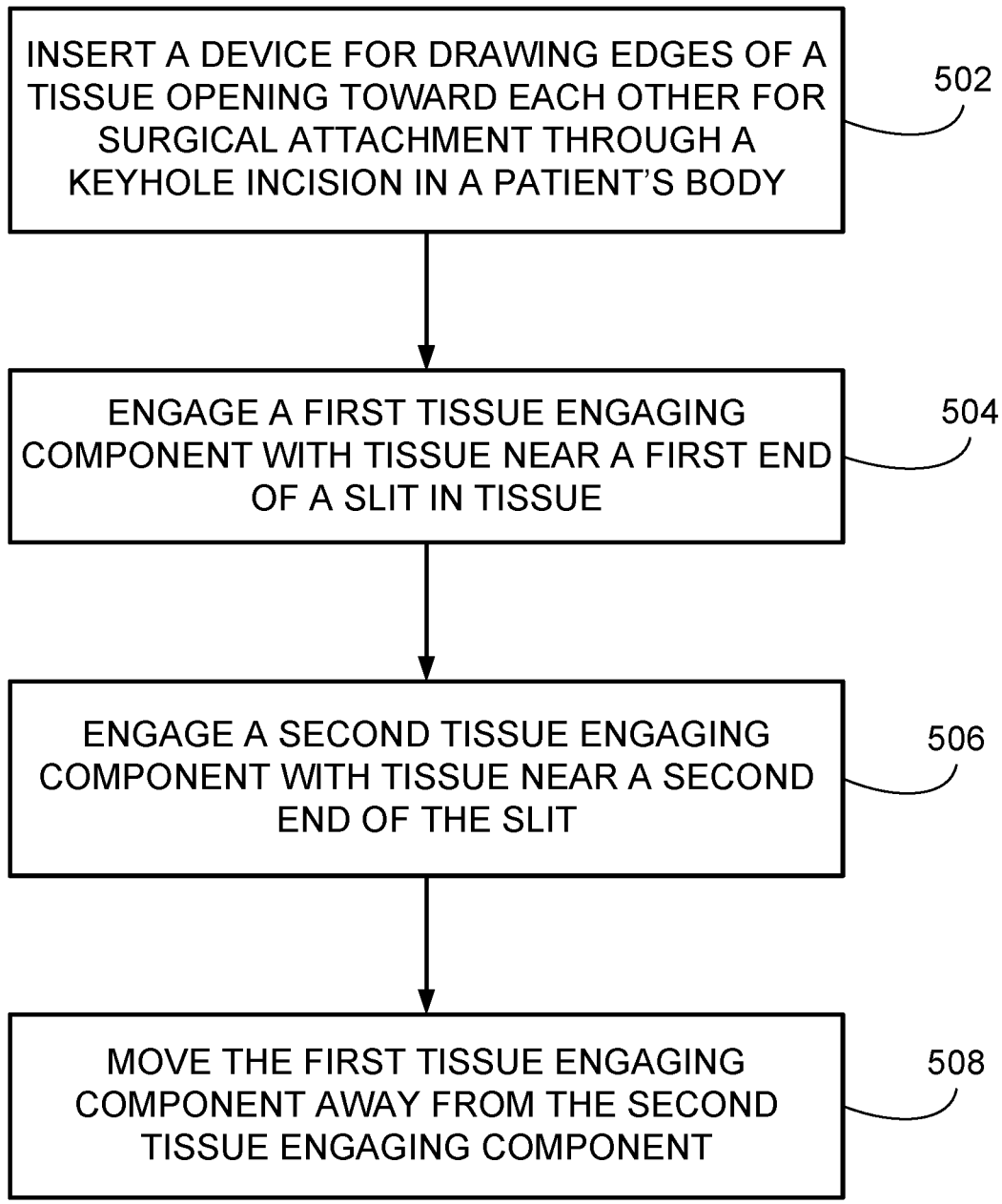
FIG. 5B is a simplified flow chart illustration of a method for drawing edges of a tissue opening toward each other for laparoscopic surgical closure of an opening in tissue according to an example embodiment of the invention.

Reference is now made to FIG. 5B, which is a simplified flow chart illustration of a method for drawing edges of a tissue opening toward each other for laparoscopic surgical closure of an opening in tissue according to an example embodiment of the invention.

The example method illustrated by FIG. 5B includes:
 inserting a device for drawing edges of a tissue opening toward each other for surgical attachment through a keyhole incision in a patient's body (502). In some embodiments, the device includes a first tissue engaging component configured to engage an opening in tissue near a first end of the opening; a second tissue engaging component configured to engage the opening near a second end of the opening; and a spreader component configured to move the first tissue engaging component away from the second tissue engaging component;
 engaging a first tissue engaging component with tissue near a first end of a slit in tissue (504);
 engaging a second tissue engaging component with tissue near a second end of the slit (506); and
 moving the first tissue engaging component away from the second tissue engaging component (508).

The above potentially causes edges of the tissue to move toward each other.

In some embodiments the engaging a first tissue engaging component with tissue near a first end of a slit in tissue (504) is an engaging a first tissue engaging component with tissue at a first location in an opening in tissue, and the engaging a second tissue engaging component with tissue near a second end of the slit (506) is an engaging a second tissue engaging component with tissue at a second location in the opening.

In some embodiments, the edges of the tissue are sutured shut.

In some embodiments, the edges of the tissue are optionally pulled into an opening between a stapler and a stapler anvil.

In some embodiments, a stapler and a stapler anvil are optionally moved toward the edges of the tissue, optionally on both sides of the edges of the tissue.

In some embodiments, the edges of the tissue are stapled shut.

Figure 5C:
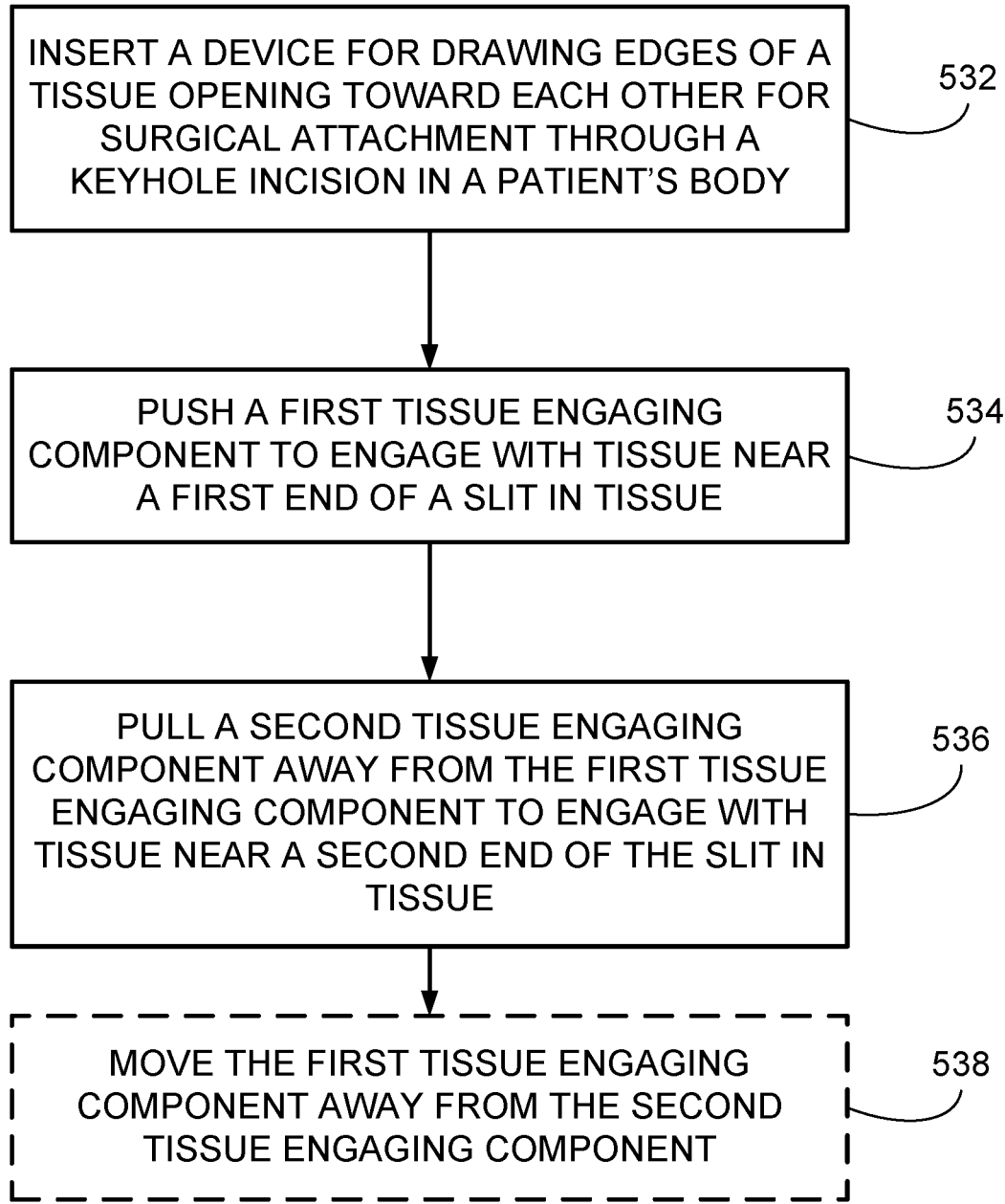
FIG. 5C is a simplified flow chart illustration of a method for drawing edges of a tissue opening toward each other for laparoscopic surgical closure of an opening in tissue according to an example embodiment of the invention.

Reference is now made to FIG. 5C, which is a simplified flow chart illustration of a method for drawing edges of a tissue opening toward each other for laparoscopic surgical closure of an opening in tissue according to an example embodiment of the invention;

The example method illustrated by FIG. 5C includes:

inserting a device for drawing edges of a tissue opening toward each other for surgical attachment through a keyhole incision in a patient's body (532). In some embodiments, the device includes a first tissue engaging component configured to engage an opening in tissue at a first location in the opening; a second tissue engaging component configured to engage the opening at a second location in the opening; and a spreader component configured to move the first tissue engaging component away from the second tissue engaging component;

pushing a first tissue engaging component to engage with tissue near a first end of a slit in tissue (534); and pushing a second tissue engaging component away from the first tissue engaging component to engage with tissue near a second end of a slit in tissue (536); and optionally, moving the first tissue engaging component away from the second tissue engaging component (538).

The above potentially causes edges of the tissue to move toward each other.

In some embodiments the pushing a first tissue engaging component to engage with tissue near a first end of a slit in tissue (534) is pushing a first tissue engaging component to engage with tissue at a first location in the opening in tissue, and the pushing a second tissue engaging component away from the first tissue engaging component to engage with tissue near a second end of a slit in tissue (536) is a pushing a second tissue engaging component away from the first tissue engaging component to engage with tissue at a second location in the opening in tissue.

In some embodiments, the edges of the tissue are sutured shut.

In some embodiments, the edges of the tissue are optionally pulled into an opening between a stapler and a stapler anvil.

In some embodiments, a stapler and a stapler anvil are optionally moved toward the edges of the tissue, optionally on both sides of the edges of the tissue.

In some embodiments, the edges of the tissue are stapled shut.

Figure 5D:
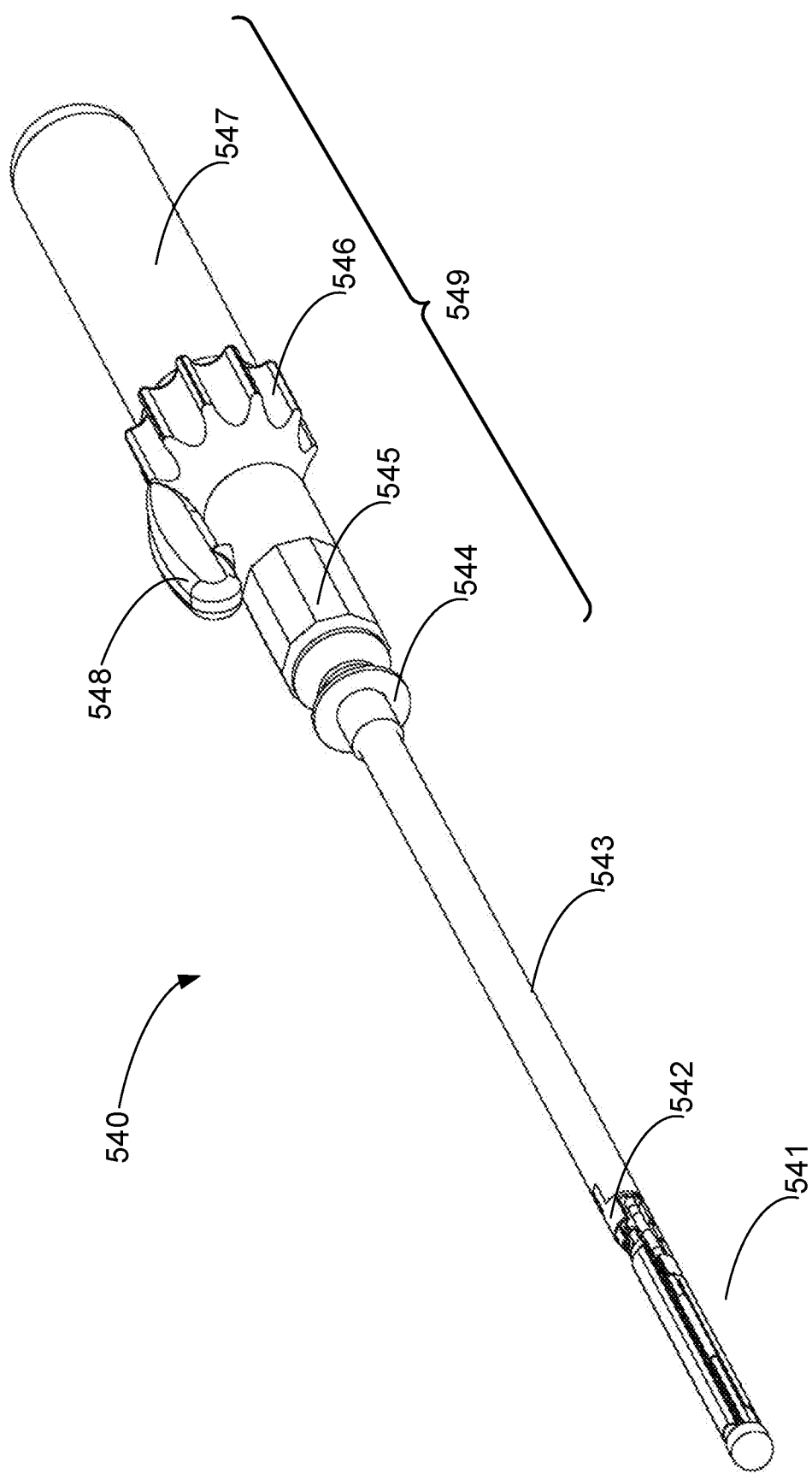
FIG. 5D is a simplified illustration of a device according to an example embodiment of the invention.

Reference is now made to FIG. 5D, which is a simplified illustration of a device according to an example embodiment of the invention.

FIG. 5D is intended to show an embodiment of a device for drawing edges of a tissue opening toward each other without a tissue stapler.

FIG. 5D shows a device 540 configured to be inserted into a patient's body though a keyhole opening, optionally through a trocar.

The example device 540 includes:

a component 541 for drawing edges of tissue opening toward each other for laparoscopic surgical closure;

an optional hinge 542 for optionally changing an angle of the component 541 relative to a shaft 543;

an optional control 544 for optionally moving tissue engagement components (not referenced in FIG. 5D) of the component 541 toward or away from each other;

an optional control 545 for optionally rotating tissue engagement components relative to the shaft 543 and/or relative to the component 541;

an optional control 548 for optionally controlling the optional hinge 542; an optional dial control 546 to optionally rotate the shaft 543 relative to a handle 547.

FIG. 5D also shows a first portion 549 of the device 540, the first portion 549 configured for operating the device 540 from outside a patient's body.

Figure 5E:
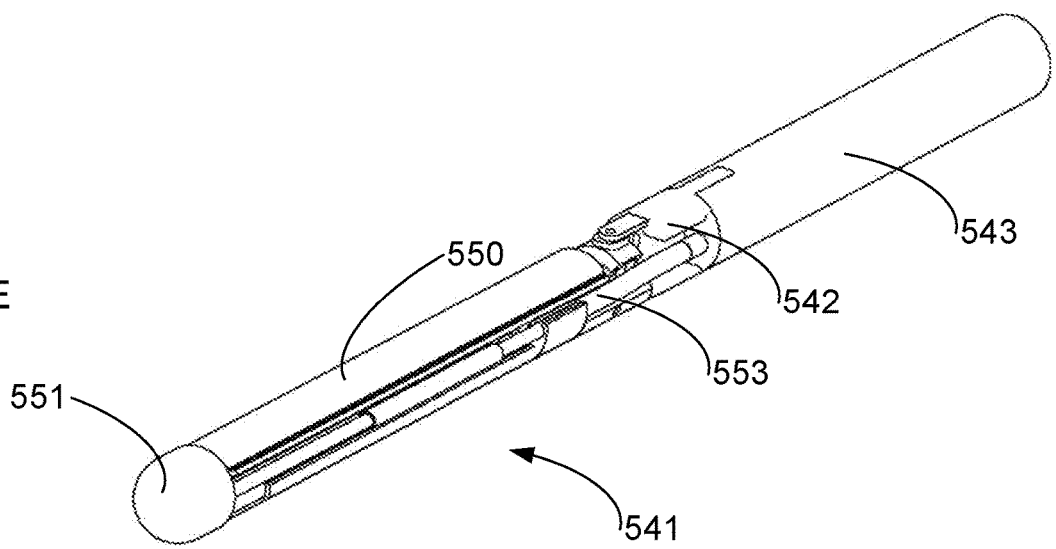
FIGS. 5E-5G are simplified illustrations of the device of FIG. 5D.
Figure 5F:
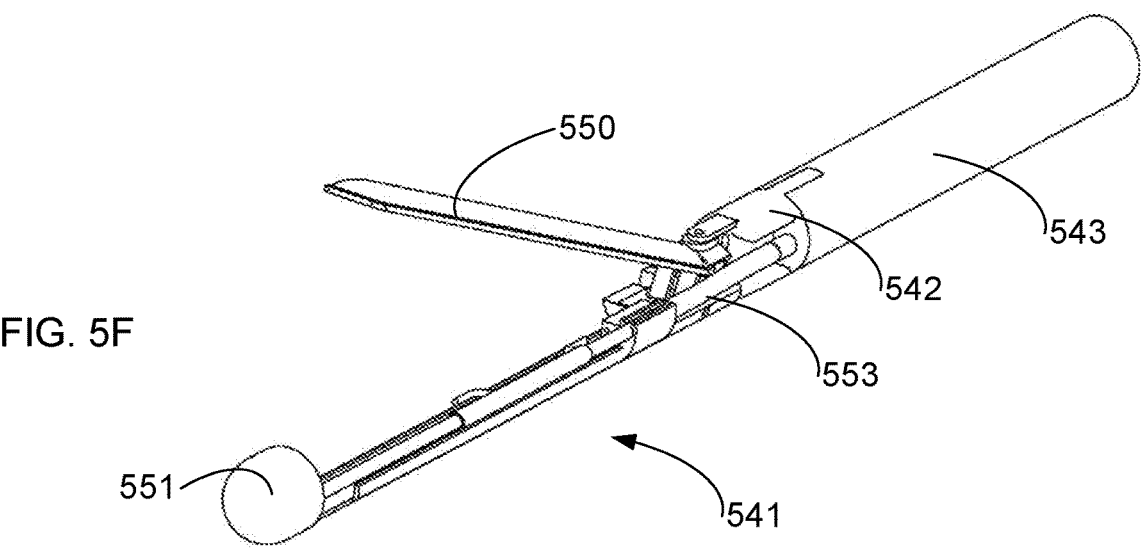
Figure 5G:
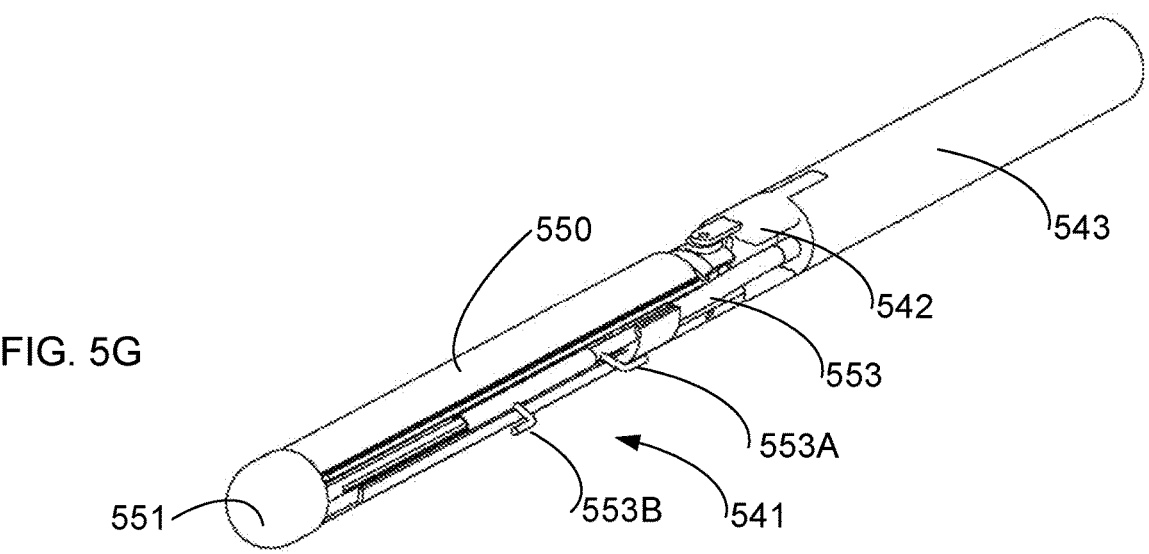

Reference is now made to FIGS. 5E-5G, which are simplified illustrations of the device of FIG. 5D.

FIG. 5E-5G show parts within a component 541 for drawing edges of tissue opening toward each other.

FIGS. 5E-5G show:

the shaft 543;

the component 541;

the optional hinge 542:

a flexible shaft 553 for controlling movement of parts within the component 541;

two prongs 553A 553B;

an optional cover 550; and an optional tip 551.

The component 541 optionally includes a wire, not shown, for controlling movement and/or rotation of the prongs 553A 553B from outside a patient's body.

In some embodiments one or both of the two prongs 553A 553B may optionally be tissue graspers and not prongs.

An example sequence of operation of the device 540 of FIG. 5D will now be described.

FIG. 5E shows the cover 550 closed, covering the two prongs 553A 553B (which are shown in FIG. 5F). When the cover 550 is optionally closed over the two prongs 553A 703B, the component 541 and the shaft 543 are narrow and can pass through a trocar, and/or move inside a patient's body without snagging.

In some embodiments the component 541 is optionally inserted into a patient's body, optionally through a trocar. In some embodiments the component 541 is optionally placed near an opening in tissue.

FIG. 5F shows the cover 550 open, which enables shifting the two prongs 553A 553B to jut away from an outline of the component 541, so that the prongs 553A 553B can catch edges of an opening in tissue.

FIG. 5G shows the two prongs 553A 553B jutting out from the component 541. The prongs 553A 553B can optionally catch edges of an opening in tissue, and pull on them causing the edges to draw close to each other and form a narrow opening. In some embodiments where there are tissue graspers, when tissue graspers are moved away from each other, the tissue edges also draw close to each other and form a narrow opening.

In some embodiments the device 540 includes a fail-safe mechanism, which prevents the two prongs 553A 553B from being moved to jut from the component 541 when the cover 550 is not open.

In some embodiments the device 540 includes a fail-safe mechanism, which prevents closing the cover 550 when the two prongs 553A 553B are not completely inside the component 541.

In some embodiments the device 540 includes a fail-safe mechanism, which prevents closing the cover 550 when the two prongs 553A 553B are not completely outside the component 541.

In some embodiments the device 540 includes a fail-safe mechanism, which prevents closing the cover 550 when the two prongs 553A 553B are not completely inside the component 541 or completely outside the component 541.

Figure 5H:
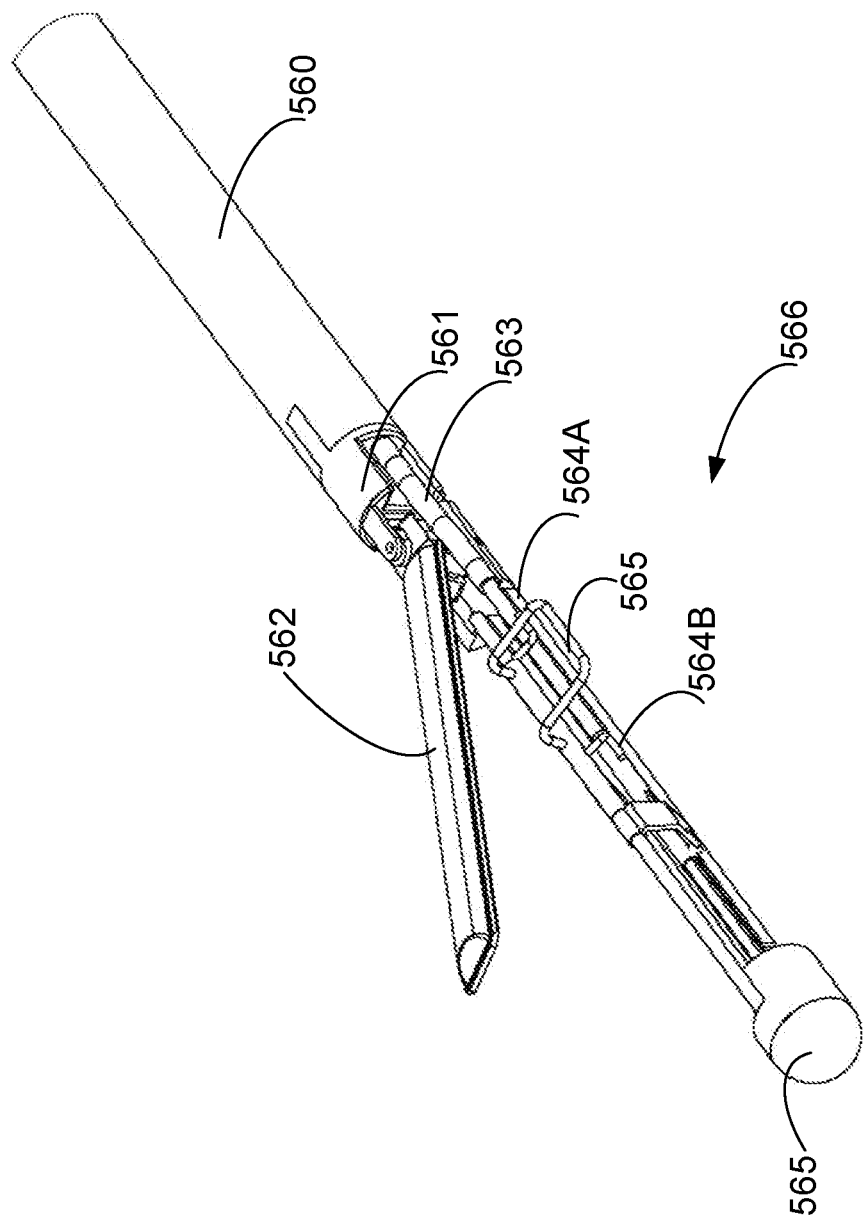
FIG. 5H is a simplified illustration of a device according to an example embodiment of the invention.

Reference is now made to FIG. 5H, which is a simplified illustration of a device according to an example embodiment of the invention.

FIG. 5H is intended to show a device suitable for laparoscopic operation and having a rest for aligning and/or locating a tissue stapler at a correct location for stapling edges of tissue.

FIG. 5H shows parts within a component 566 for drawing edges of tissue opening toward each other.

FIG. 5H shows:
- a shaft 560;
- a component 566;
- an optional hinge 561:
- a flexible shaft 563 for controlling movement of parts within the component 566;
- two prongs 564A 564B;
- a rest 565 for aligning and/or locating a tissue stapler at a correct location for stapling edges of a tissue opening which are aligned and/or drawn together by the two prongs 564A 564B;
- an optional cover 562; and
- an optional tip 565.

The component 566 optionally includes a wire, not shown, for controlling movement and/or rotation of the prongs 564A 564B from outside a patient's body.

In some embodiments one or both of the two prongs 564A 564B may optionally be tissue graspers and not prongs.

Figure 6A:
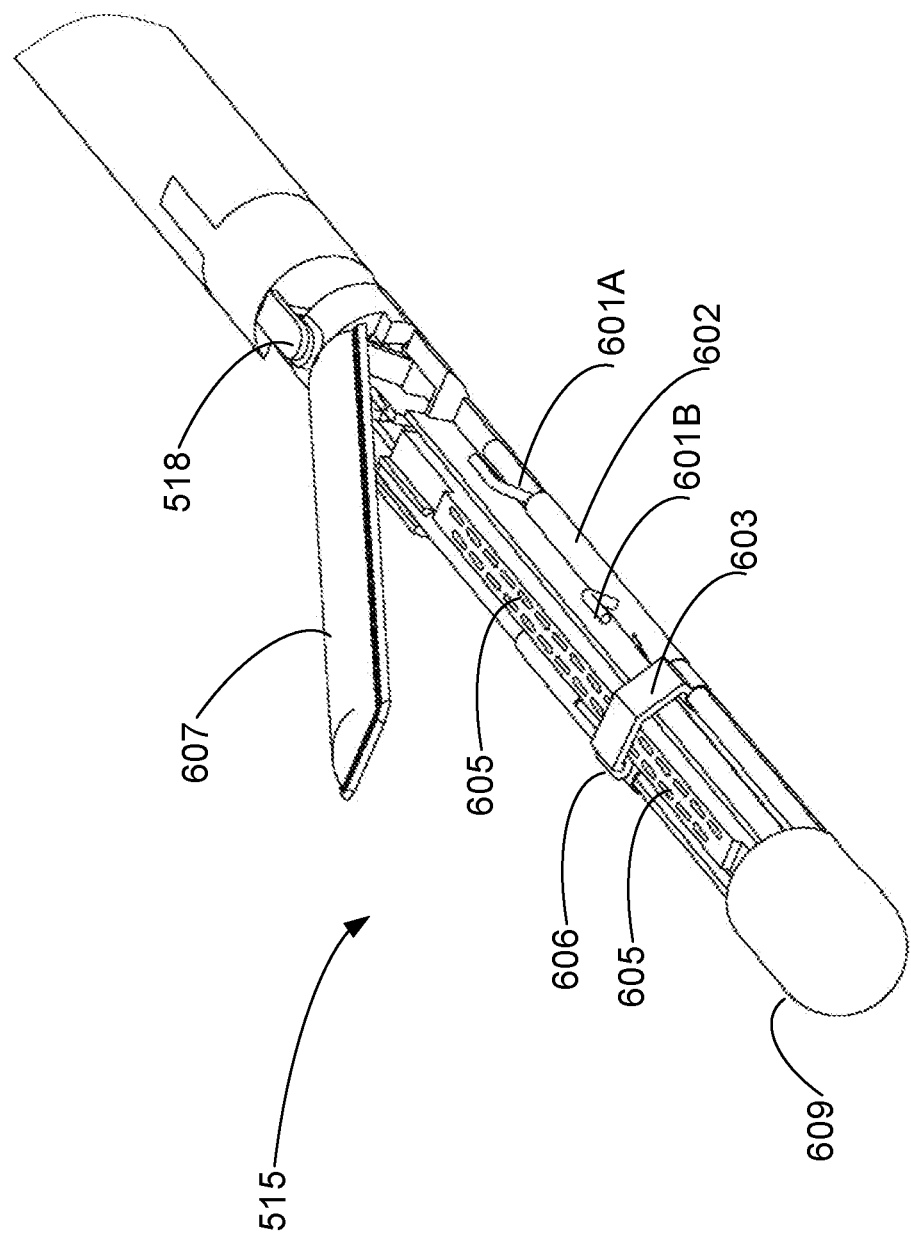
FIG. 6A is a simplified illustration of the component for drawing edges of tissue opening toward each other of FIG. 5A.

Reference is now made to FIG. 6A, which is a simplified illustration of the component for drawing edges of tissue opening toward each other of FIG. 5A.

FIG. 6A shows parts within the component 515 of FIG. 5A.

FIG. 6A shows:
- an optional hinge 518 also shown as hinge 518 in FIG. 5A;
- two prongs 601A 601B and a cylinder 602 enabling the two prongs 601A 601B to slide toward and away from each other along the axis of the cylinder 602, optionally by wire control from outside a patient's body and/or by a spring (not shown) pushing the prongs 601A 601B apart, the spring being between the two prongs 601A 601B and/or pushing a wire from outside the patient's body;
- an optional bridge 603, for optionally rotating the prongs relative to a hinge, optionally by control from outside the patient's body;
- an optional stapler 605, operation of which is optionally controlled from outside the patient's body;
- a cover 607 and/or stapler anvil 607, optionally opened and/or closed controlled from outside the patient's body; and
- an optional tip 609.

FIG. 6A shows the cover/anvil 607 open, so that internal parts can be seen. The cover/anvil 607 may be closed, keeping the component 515 narrow so as to pass through a trocar, and/or for moving inside a patient's body without snagging.

In some embodiments one or both of the two prongs 601A 601B may optionally be tissue graspers and not prongs.

An example sequence of operation of the device 500 of FIG. 5A will now be described.

A portion of the device 500 including the component 515 is inserted into a patient's body, optionally through a trocar.

In some embodiments the component 515 has a maximum diameter in a range between 5 millimeters and 15 millimeters, so as to pass through a trocar.

Figure 6B:
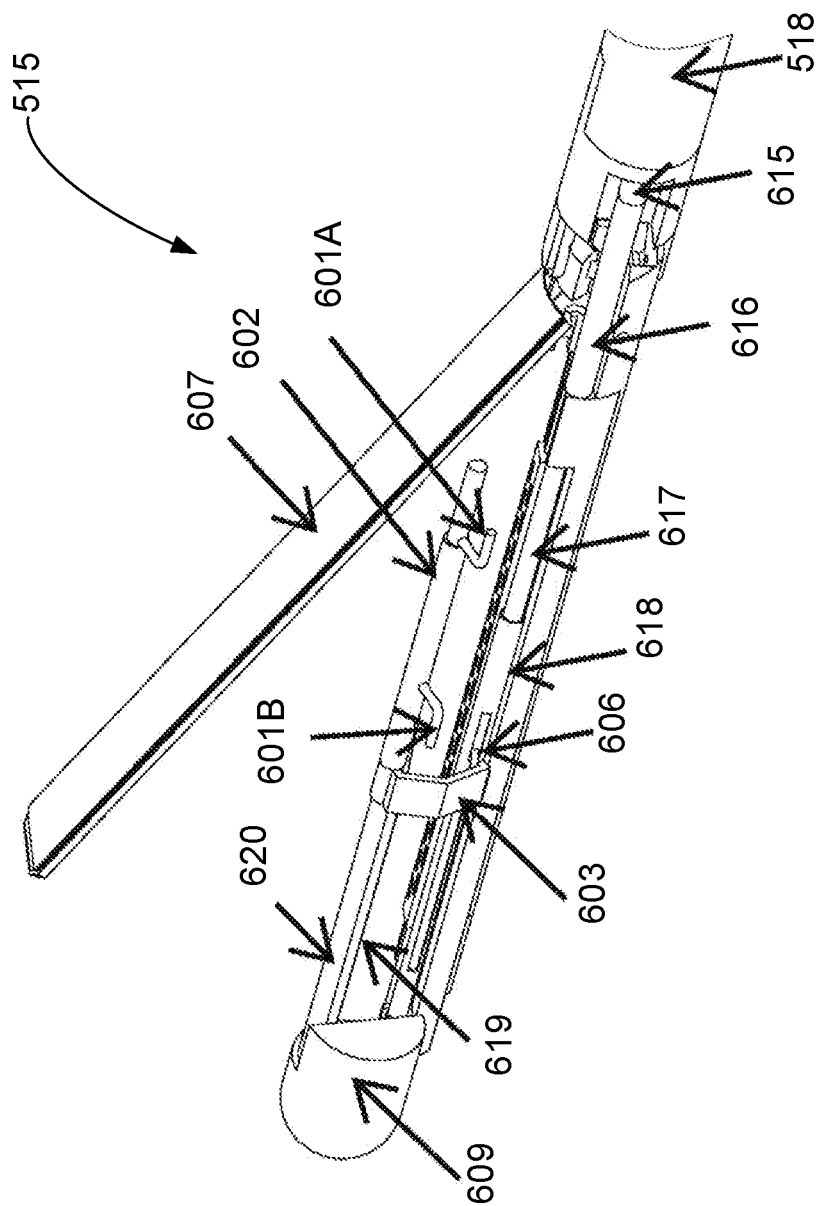
FIG. 6B is a simplified illustration of the component for drawing edges of tissue opening toward each other of FIG. 5A.

Reference is now additionally made to FIG. 6B, which is a simplified illustration of the component for drawing edges of tissue opening toward each other of FIG. 5A.

FIG. 6B shows the component 515, optionally within the patient's body (the patient's body is not shown), with the cover/anvil 607 open, and the prongs 601A 601B rotated out of the inside of the component 515, optionally rotated so that the prongs 601A 601B jut toward an outer direction, so they can be placed next to and into an opening or a slit in tissue.

FIG. 6B also shows:
- an optional rod 615 for transferring rotation and/or back-and-forth movement to parts in the component 515;
- an optional flexible rod 616 for transferring rotation and/or back-and-forth movement from the optional rod 615 to parts in the component 515 even when the hinge 518 is at an angle. In some embodiments the flexible rod 616 optionally includes one or more of the following features: a hollow tube; a slotted tube; a spring for transferring rotation; a two-layered spring for transferring rotation. In some embodiments the rod is capable of transferring torque in a range from 5 to 10, 50, 100, 150, 200, 250 mm-Newton;
- an optional second rod 617 for transferring rotation and/or back-and-forth movement of the flexible rod 616;
- an optional wire 606 for transferring control from the outside the body through the rods 615 616 617;
- an optional slider 618 sliding on the rod 617, for guiding movement in the component 515;
- an optional spring 619 for optionally pulling or pushing the two prongs 601A 601B apart; and
- an optional rod 620.

In some embodiments the component 515 includes a fail-safe mechanism, which prevents the prongs 601A 601B from being moved to jut from the component 515 when the cover/anvil 607 is not open.

In some embodiments the component 515 includes a fail-safe mechanism, which prevents closing the cover/anvil 607 when the prongs 601A 601B are not completely inside the component 515.

In some embodiments the component 515 includes a fail-safe mechanism, which prevents closing the cover/anvil 607 when the prongs 601A 601B are not completely outside the component 515.

In some embodiments the component 515 includes a fail-safe mechanism, which prevents closing the cover/anvil 607 when the prongs 601A 601B are not completely inside the component 515 or completely outside the component 515.

In some embodiments the component 515 includes a fail-safe mechanism, which prevents closing the cover/anvil 607 unless the bridge 603 is in a distal position, close to the tip 609 of the component 515.

Figure 6C:
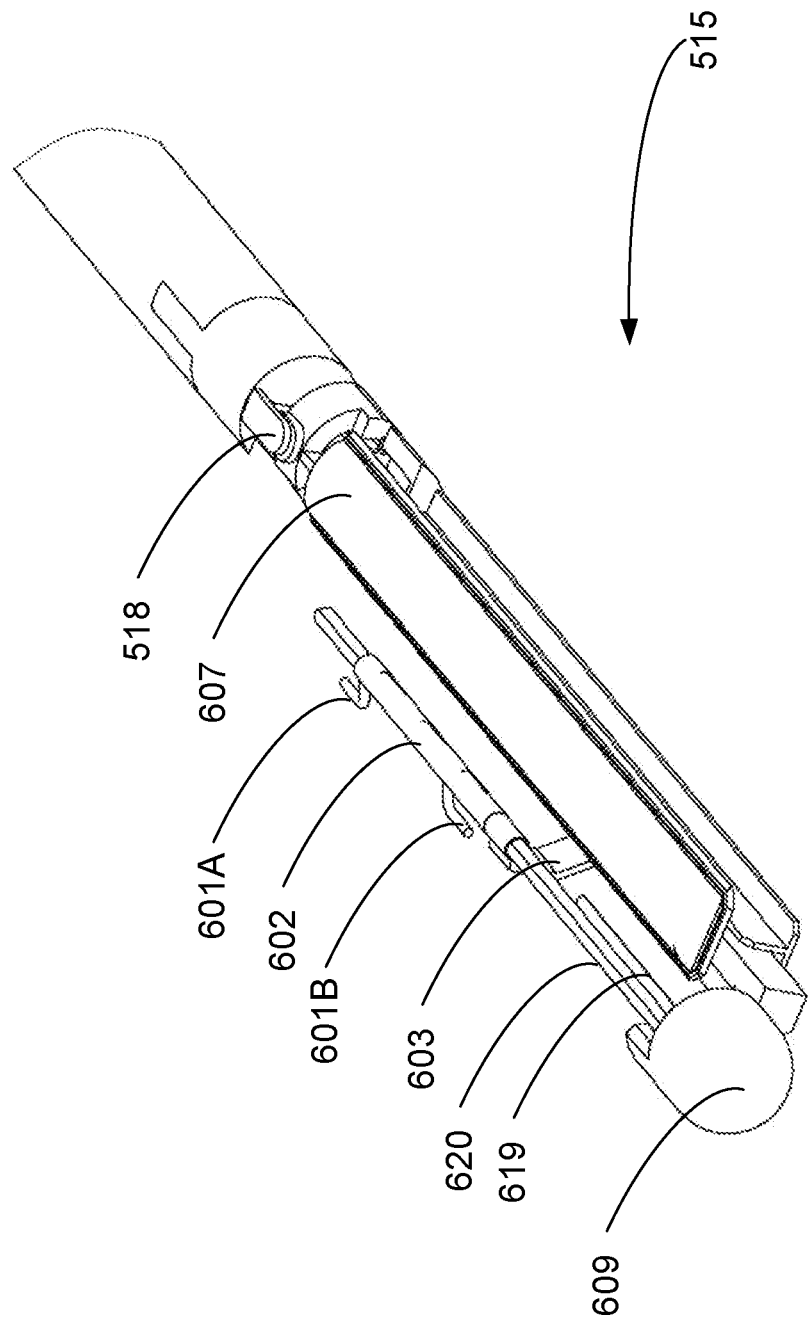
FIG. 6C is a simplified illustration of the component for drawing edges of tissue opening toward each other of FIG. 5A.

Reference is now additionally made to FIG. 6C, which is a simplified illustration of the component for drawing edges of tissue opening toward each other of FIG. 5A.

FIG. 6C shows the component 515, optionally within the patient's body (the patient's body is not shown), with the cover/anvil 607 closed, and the prongs 601A 601B rotated out of the inside of the component 515, optionally rotated so that the prongs 601A 601B and the rod 620 jut toward an outer direction, so they can be placed next to and into an opening or a slit in tissue.

FIG. 6C shows the prongs 601A 601B rotated out of the inside of the component 515, so that the prongs 601A 601B jut toward an outer direction, so they can be placed next to and into an opening or a slit in tissue.

Figure 6E:
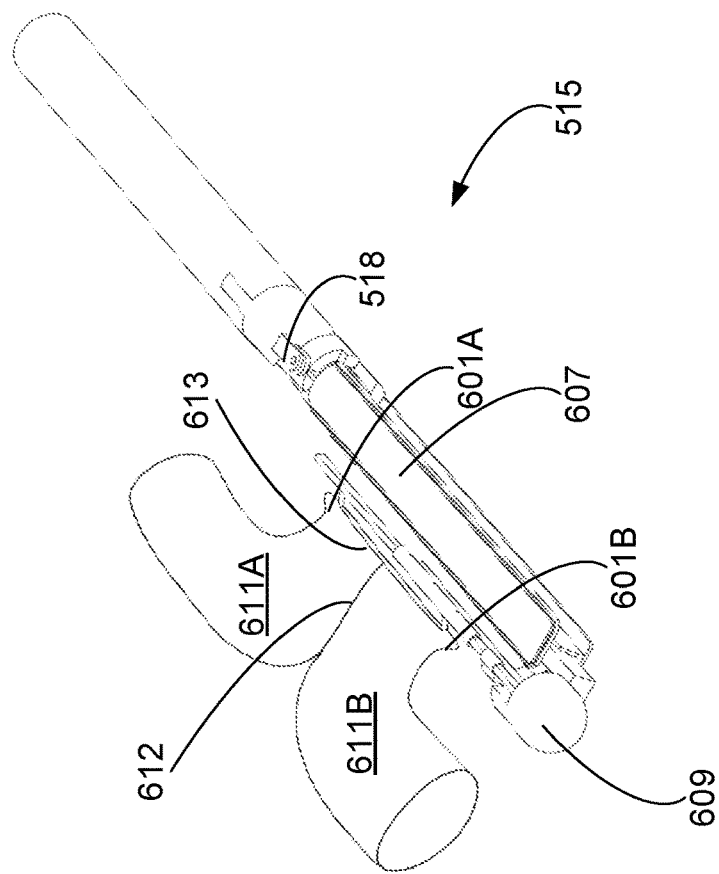
FIG. 6E is a simplified illustration of the component for drawing edges of tissue opening toward each other of FIG. 5A.
Figure 6D:
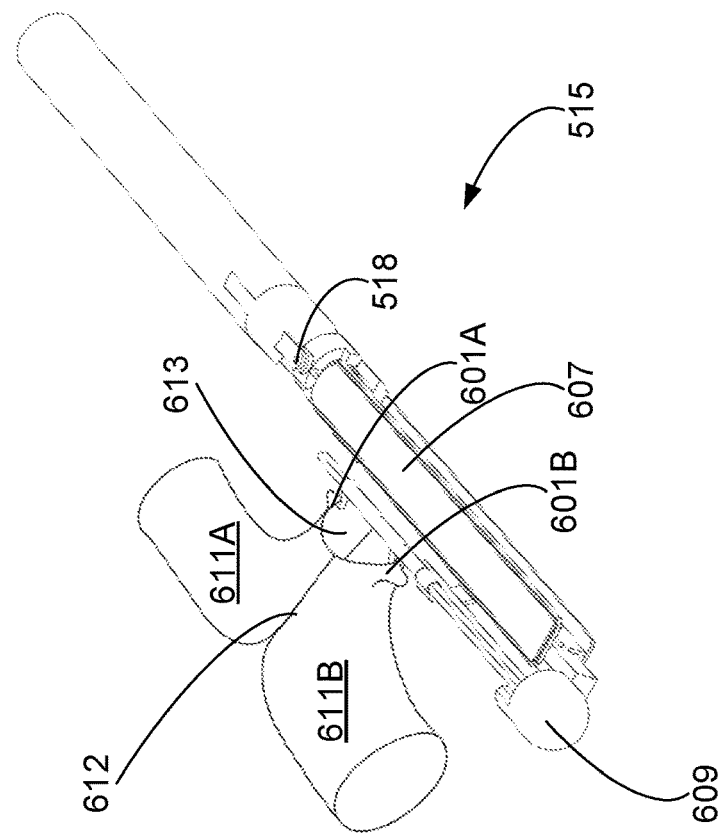
FIG. 6D is a simplified illustration of the component for drawing edges of tissue opening toward each other of FIG. 5A.

Reference is now additionally made to FIG. 6D, which is a simplified illustration of the component for drawing edges of tissue opening toward each other of FIG. 5A.

FIG. 6D shows the component 515, within the patient's body, during an example embodiment of a surgical anastomosis procedure. FIG. 6D shows two sections 611A 611B of intestine already attached to each other along a line 612, with a tissue opening 613 still open.

The prongs 601A 601B are shown inserted into the tissue opening 613.

Reference is now additionally made to FIG. 6E, which is a simplified illustration of the component for drawing edges of tissue opening toward each other of FIG. 5A.

FIG. 6E shows the component 515, within the patient's body, during the example embodiment (also described in FIG. 6D) of a surgical anastomosis procedure. FIG. 6E shows the prongs 601A 601B having been moved away from each other, pulling the tissue opening 613 and shaping the tissue opening so that edges of the tissue opening 613 are drawn toward each other.

Figure 6G:
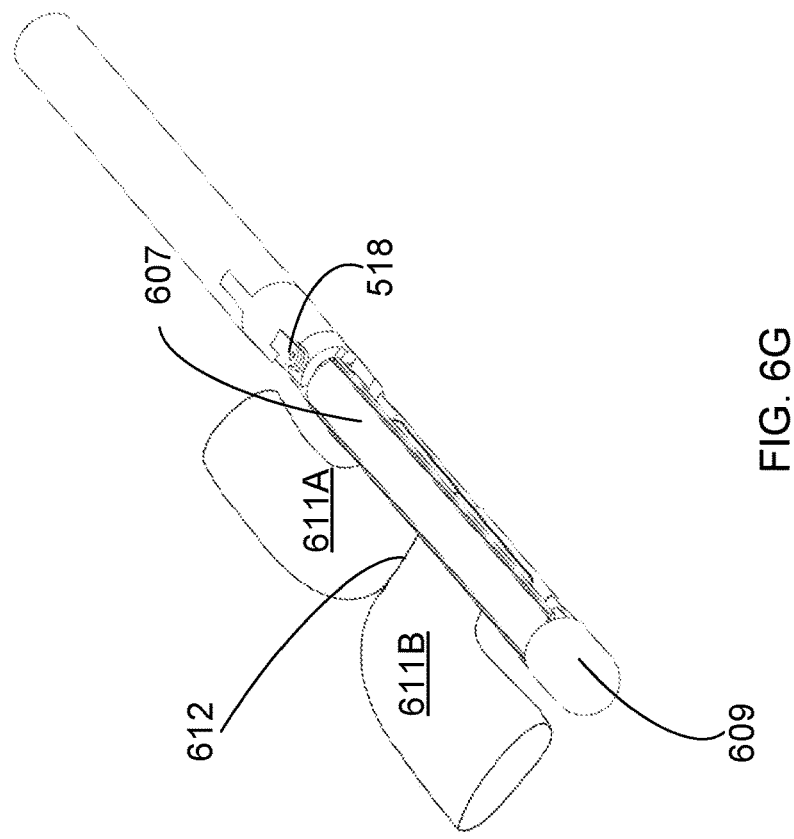
FIG. 6G is a simplified illustration of the component for drawing edges of tissue opening toward each other of FIG. 5A.
Figure 6F:
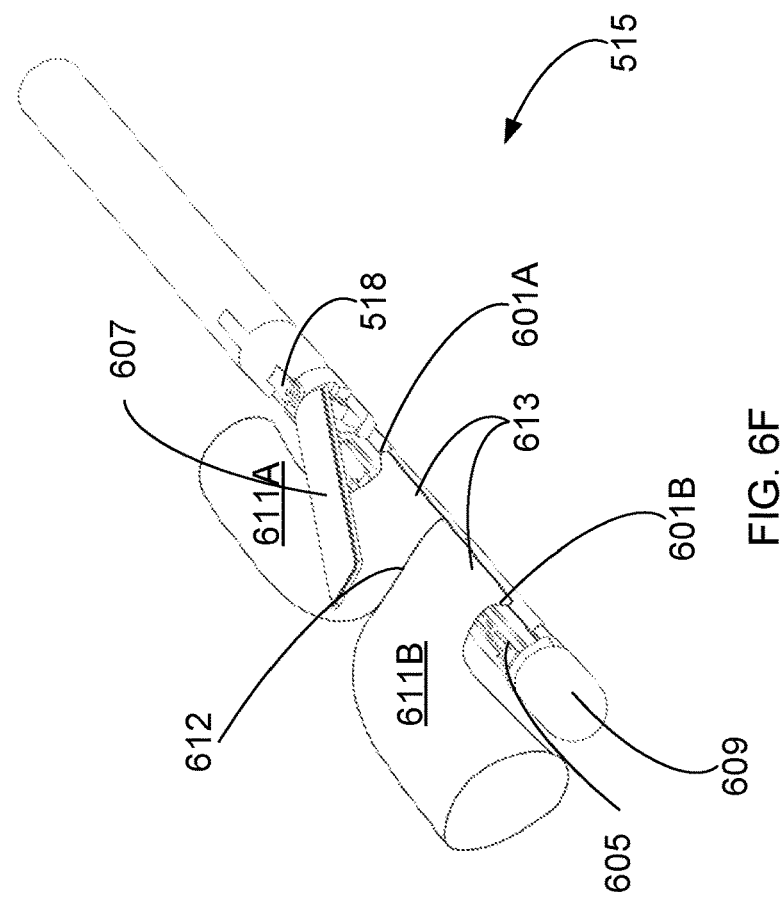
FIG. 6F is a simplified illustration of the component for drawing edges of tissue opening toward each other of FIG. 5A.

Reference is now additionally made to FIG. 6F, which is a simplified illustration of the component for drawing edges of tissue opening toward each other of FIG. 5A.

FIG. 6F shows the component 515, within the patient's body, during the example embodiment (also described in FIGS. 6D and 6E) of a surgical anastomosis procedure.

FIG. 6F shows the cover/anvil 607 open, and the prongs 601A 601B rotated back into the component 515, so that either the tissue opening 613 is pulled across the optional stapler 605, or the optional stapler 605 is pulled across the tissue opening 613.

Reference is now additionally made to FIG. 6G, which is a simplified illustration of the component for drawing edges of tissue opening toward each other of FIG. 5A.

FIG. 6G shows the component 515, within the patient's body, during the example embodiment (also described in FIGS. 6D-6F) of a surgical anastomosis procedure.

FIG. 6G shows the cover/anvil 607 closed upon the tissue and the prongs 601A 601B (not shown in FIG. 6G).

FIG. 6G shows a state of the component 515 with respect to the tissue when the optional stapler (not shown in FIG. 6G, shown in FIG. 6F) can be operated to staple the tissue.

Figure 6I:
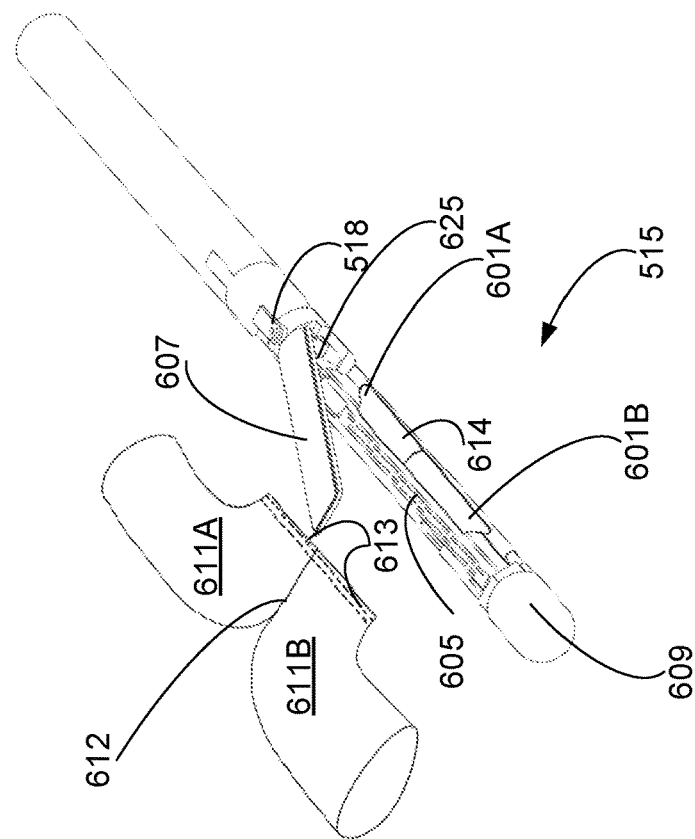
FIG. 6I is a simplified illustration of the component for drawing edges of tissue opening toward each other of FIG. 5A.
Figure 6H:
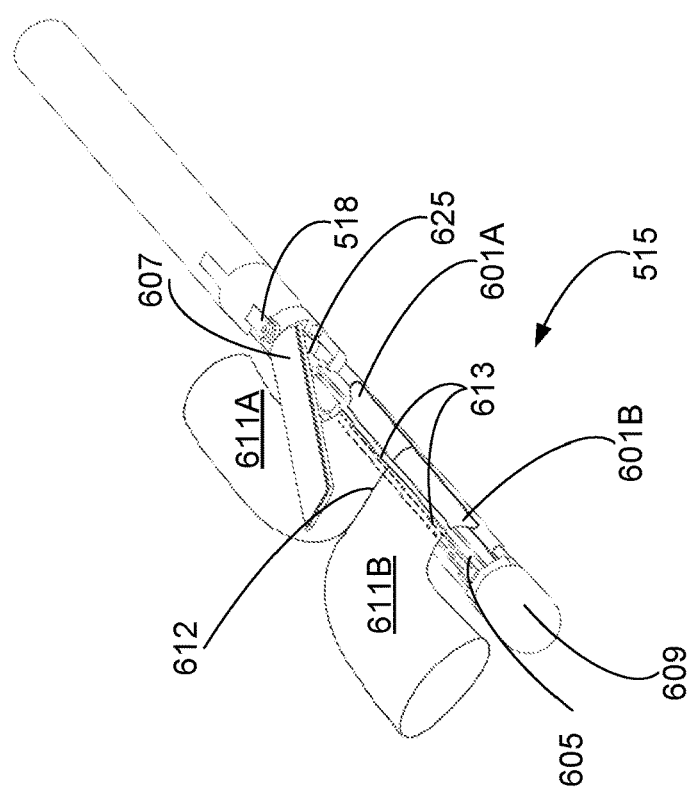
FIG. 6H is a simplified illustration of the component for drawing edges of tissue opening toward each other of FIG. 5A.

Reference is now additionally made to FIG. 6H, which is a simplified illustration of the component for drawing edges of tissue opening toward each other of FIG. 5A.

FIG. 6H shows the component 515, within the patient's body, during the example embodiment (also described in FIGS. 6D-G) of a surgical anastomosis procedure.

FIG. 6H shows the cover/anvil 607 open, and the tissue opening 613 of the two sections 611A 611B of intestine optionally stapled closed.

FIG. 6H shows the cover/anvil 607 open, however, such a step does not have to happen in a sequence of the example embodiment surgical anastomosis procedure. FIG. 6H shows the cover/anvil 607 open in order to illustrate what optionally happened within the component 515.

In some embodiments the cover/anvil 607 is opened, and the component 515 is optionally pulled away from the stapled tissue.

In some embodiments the cover/anvil 607 is left closed, and an optional tissue cutter 625 optionally cuts the tissue along the stapled edge. After cutting the tissue the component 515 can optionally be pulled away from the stapled tissue.

Reference is now additionally made to FIG. 6I, which is a simplified illustration of the component for drawing edges of tissue opening toward each other of FIG. 5A.

FIG. 6I shows the component 515, within the patient's body, during the example embodiment (also described in FIGS. 6D-H) of a surgical anastomosis procedure.

FIG. 6I shows the cover/anvil 607 open, the tissue opening 613 of the two sections 611A 611B of intestine optionally stapled closed, and a portion 614 of the tissue has option been cut away from the stapled tissue.

FIG. 6I shows the cover/anvil 607 open; however, such a step does not have to happen in a sequence of the example embodiment surgical anastomosis procedure. FIG. 6I shows the cover/anvil 607 open in order to illustrate what optionally happened within the component 515.

In some embodiments the cover/anvil 607 is opened, and the component 515 is optionally pulled away from the stapled tissue.

In some embodiments the cover/anvil 607 is left closed, and the component 515 is optionally pulled away from the stapled tissue.

Reference is now made to FIGS. 7A-C, which are simplified illustrations of a component for drawing edges of tissue opening toward each other according to an example embodiment of the invention.

FIG. 7A-C show parts within a component 700 for drawing edges of tissue opening toward each other.

FIGS. 7A-C show:
two prongs 703A 703B; and
a cover and/or stapler anvil 702 enabling the two prongs 703A 703B to optionally slide toward and away from each other along the axis of the cover/anvil 702 and/or optionally rotate about an axis of a cylinder 704.

The component 700 optionally includes a wire, not shown, for controlling movement and/or rotation of the prongs 703A 703B from outside a patient's body;

In some embodiments one or both of the two prongs 701A 701B may optionally be tissue graspers and not prongs.

An example sequence of operation of the device 700 of FIGS. 7A-C will now be described.

FIG. 7A shows the two prongs 703A 703B in-line with a base 706 of the component 700. When the two prongs 703A 703B are in-line with the base 706, the component 700 is narrow and can pass through a trocar, and/or move inside a patient's body without snagging.

In some embodiments the component 700 is optionally inserted into a patient's body, optionally through a trocar. In some embodiments the component 700 is optionally placed near an opening in tissue.

FIG. 7B shows the two prongs 703A 703B rotated and jutting away from an outline of the component 700, so that the prongs 703A 703B can catch edges of an opening in tissue. The prongs 703A 703B can be inserted into a tissue opening or a slit in tissue, similarly to FIG. 6D.

FIG. 7C shows the two prongs 703A 703B moving away from each other. The prongs 703A 703B can optionally catch edges of an opening in tissue, and pull on them causing the edges to draw close to each other and form a narrow opening. In some embodiments where there are tissue graspers, when tissue graspers are moved away from each other, the tissue edges also draw close to each other and form a narrow opening.

Reference is now additionally made to FIGS. 7D-F, which are simplified illustrations of the component for drawing edges of tissue opening toward each other of FIGS. 7A-C according to an example embodiments of the invention.

An optional continuation of the example sequence of operation of the device 700 shown in FIGS. 7A-C will now be described.

FIGS. 7D-F show some of the same components as FIGS. 7A-C.

FIGS. 7A-7C may be understood as not including a tissue stapler, however in some embodiments the component 700 optionally also includes a tissue stapler, and the operation shown in FIGS. 7A-C can optionally be performed when the component 700 does include a tissue stapler.

FIGS. 7D-F show a component 710 which includes a tissue stapler 708.

FIG. 7D shows the two prongs 703A 703B in a position similar to that shown in FIG. 7C, potentially having engaged edges of a tissue opening (not shown) and pulled them apart, to draw the edges close to a shape of a narrow opening or a slit.

FIG. 7D also shows the tissue stapler 708 pulled away from the cylinder 704 and the two prongs 703A 703B, leaving a space between the tissue stapler 708 and the cylinder 704.

FIG. 7E shows what happens when the two prongs 703A 703B are rotated, potentially either pulling edges of tissue in front of a face of the tissue stapler 708, into the space between the tissue stapler 708 and the cylinder 704, or pulling the face of the tissue stapler 708 and the cylinder 704 across the tissue opening 613.

FIG. 7F shows the tissue stapler 708 closed, potentially stapling tissue edges (not shown) together.

FIGS. 7A-C showed an example embodiment causing prongs to jut out by rotating the prongs, and FIGS. 7D-F showed an example embodiment causing edges of tissue to be pulled by rotating the prongs or a stapler to be pulled toward the tissue edges by the rotation.

Example embodiments will now be shown where prongs will jut out using a parallelogram design, and causing edges of tissue being pulled by a parallelogram design.

Reference is now made to FIGS. 8A-F, which are simplified illustrations of a component for drawing edges of tissue opening toward each other according to an example embodiment of the invention.

FIG. 8A-F show parts within a component 800 for drawing edges of tissue opening toward each other.

FIGS. 8A-F show:
two prongs 803A 803B;
a rod 808 upon which one or more of the prongs 803A 803B optionally slide;
a linkage 809, optionally a parallel linkage, for optionally shifting the rod 808 and prongs 803A 803B side-to-side;
an optional cover and/or stapler anvil 806;
an optional tissue stapler 807; and
an optional rounded tip 802.

In some embodiments one or both of the two prongs 803A 803B may optionally be tissue graspers and not prongs.

In some embodiments the component 800 optionally includes a spring (not shown) for moving the prongs 803A 803B away from each other.

An example sequence of operation of the device 800 of FIGS. 8A-E will now be described.

Figures 8A, 8B, 8C:
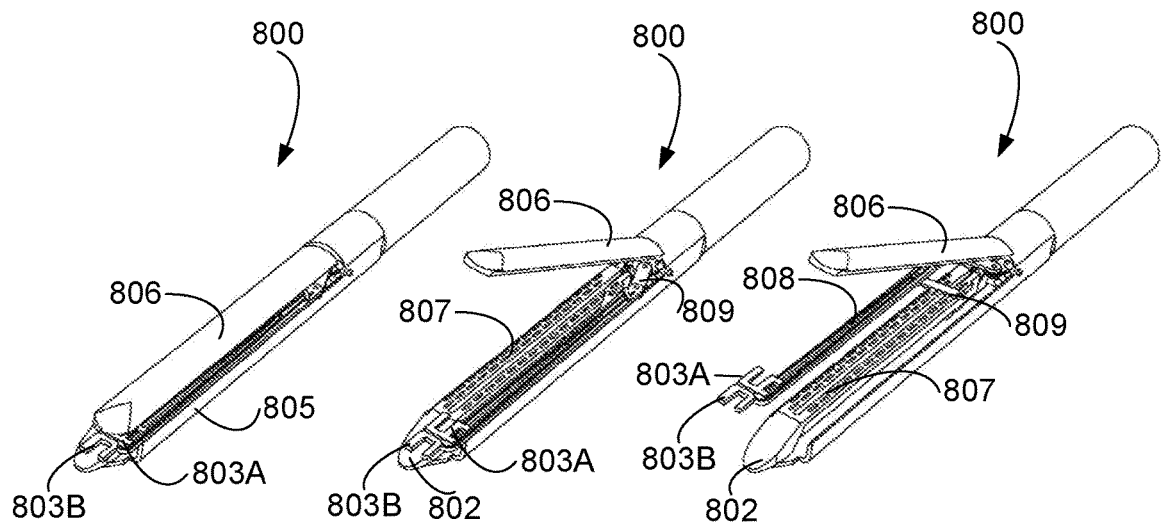

FIG. 8A shows the two prongs 803A 803B within an outline of the component 800, and close to each other. When the two prongs 803A 803B are within the outline of the component 800, the component 800 is narrow and can pass through a trocar, and/or move inside a patient's body without snagging.

In some embodiments the component 800 is optionally inserted into a patient's body, optionally through a trocar. In some embodiments the component 800 is optionally placed near an opening in tissue.

FIG. 8B shows the optional cover and/or stapler anvil 806 open. FIG. 8B shows parts of the component 800 which are not shown in FIG. 8A because FIG. 8A shows the optional cover and/or stapler anvil 806 closed.

FIG. 8C shows the two prongs 803A 803B jutting sideways from the outline of the component 800, ready to be inserted into an opening in tissue (not shown). The two prongs 803A 803B were optionally made to jut sideways from the outline of the component 800 by moving the rod 808 sideways, optionally by operating the linkage 809.

At this point the two prongs 803A 803B are optionally inserted into an opening in tissue, optionally catching edges of the opening in tissue.

Figures 8D, 8E, 8F:
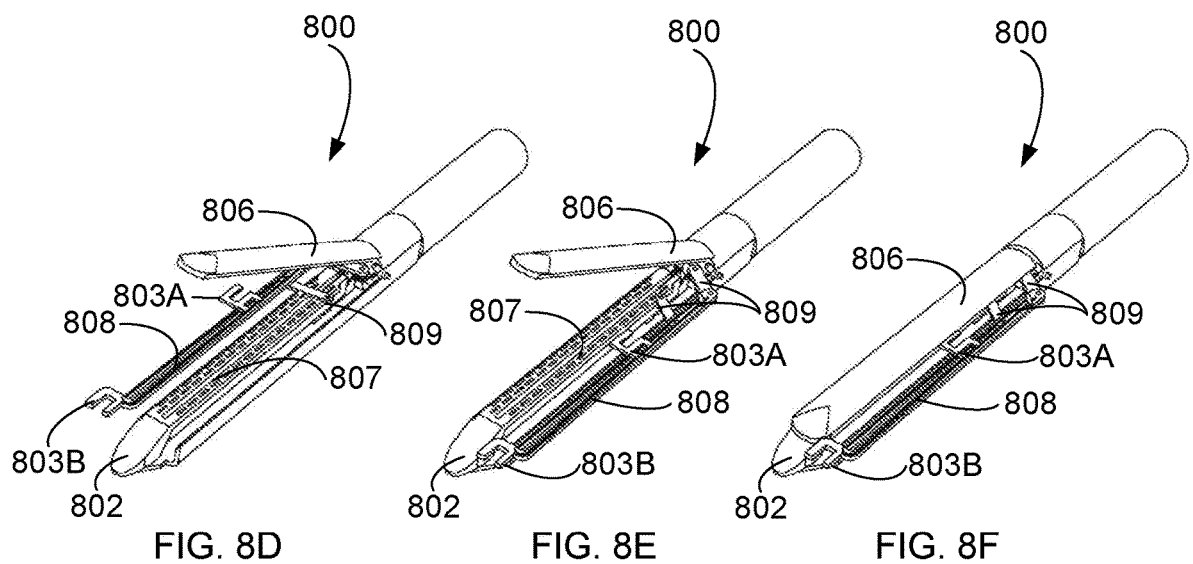

FIG. 8D shows the two prongs 803A 803B after moving away from each other. The prongs 803A 803B optionally pull on edges of the tissue opening, causing the edges to draw close to each other and form a narrow opening or slit. In some embodiments where there are tissue graspers, when tissue graspers are moved away from each other, the tissue edges also draw close to each other and form a narrow opening or slit.

FIG. 8E shows the two prongs 803A 803B pulled into the outline of the component 800, potentially pulling edges of the tissue opening to a location above the optional tissue stapler 807, or pulling the component 800 onto the tissue edges, optionally with the cover and/or stapler anvil 806 on side of the tissue edges and the optional tissue stapler 807 on the other side of the tissue edges.

FIG. 8F shows the optional tissue stapler 807 closed, potentially stapling tissue edges (not shown) together.

Reference is now made to FIG. 9, which is a simplified illustration of a component for drawing edges of tissue opening toward each other attached to a hinge according to an example embodiment of the invention.

FIG. 9 shows a component 900 for drawing edges of tissue opening toward each other, attached to a hinge 904, attached to a control shaft 908.

FIG. 9 shows the component 900 and an angle 910 to the control shaft 908.

The component 900 can optionally be shifted from one side to another by pushing/pulling a rod 911 connected to the component 900 by a hinge 912.

FIG. 9 also shows an optional control flexible shaft 906 and how the flexible shaft 906 can pass from the control shaft 908 to the component 900.

In some embodiments the flexible shaft 906 is optionally a hollow flexible shaft, to enable a wire going through (the wire is not shown).

Referring again to FIG. 6B, it is noted that a flexible shaft such as the 906 can optionally rotates the rod 617 of FIG. 6B, and the prongs 601A and 601B.

In some embodiment a push/pull wire (not shown) goes through the hollow flexible shaft in order to slide and/or rotate the bridge 603 of FIG. 6B and/or to control the prongs.

In some embodiments more than one control wire and/or flex shaft 906 are optionally used.

Detachable Shaft

Reference is now made to FIGS. 10A and 10B, which are simplified illustrations of a device according to an example embodiment of the invention.

FIGS. 10A and 10B show a device 1000 configured to be inserted into a patient's body though a keyhole opening, optionally through a trocar.

The device 1000 is optionally configured so a distal portion 1007B of a shaft of the device 1000 may optionally be detached from a proximal portion 1007A of the device 1000.

In some embodiments the proximal portion 1007A of the device 1000 includes controls for operating the distal portion 1002 of the device 1000.

In some embodiments the distal portion 1007B of the device 1000 is optionally replaceable or even disposable.

FIG. 10A shows the device 1000 with the distal portion 1007B of the shaft of the device 1000 attached to the proximal portion 1007A of the device 1000 and optionally controllable by the controls in the proximal portion 1007A.

FIG. 10B shows the device 1000 with the distal portion 1007B of the shaft of the device 1000 detached from the proximal portion 1007A of the device 1000.

FIGS. 10A and 10B show a location 1008 where the distal portion 1007B of the shaft of the device 1000 connects to the proximal portion 1007A of the device 1000.

FIG. 10B shows one or more mechanism(s) 1020 1022 at the location 1008 for transferring control motions from controls, such as optional controls 1010 1013 1016 1017 1021 1023, to the components in the distal portion 1007B of the shaft of the device 1000.

The device 1000 shown in FIGS. 10A and 10B also includes:
- a component 1015 for drawing edges of a tissue opening toward each other for laparoscopic surgical closure;
- one or more optional controls 1010 1013 1016 1017 1021 1023 for optionally operating components in the distal portion 1007B of the shaft.
- an optional grip 1019 for grasping the device 500; and
- an optional handle 1011 for containing the controls.

In some embodiments the component 1015 optionally includes one or more of: a mechanism for drawing edges of tissue opening toward each other, a stapler, a tissue cutter, an optional hinge. In some embodiments the optional controls 1010 1013 1016 1017 1021 1023 operate one or more of the mechanism for drawing edges of a tissue opening toward each other, the stapler, the tissue cutter, and the hinge.

Add-on Device

Reference is now made to FIGS. 11A-11F, which are simplified illustrations of a device according to an example embodiment of the invention.

FIGS. 11A-11F show an add-on device for adding to an tissue stapler in order to provide additional functionality of drawing edges of a tissue opening toward each other and/or cutting stapled tissue.

FIG. 11A shows a simplified illustration of a stapler 1102 at an end of a shaft 1101.

FIG. 11B shows a simplified illustration of an add-on device 1100.

In some embodiments, the add-on device 1100 optionally includes one or more of:
- two prongs 1109 1110 for drawing edges of a tissue opening toward each other;
- a prong support 1108 for supporting the prongs 1109 1110, along which one or more of the prongs 1109 1110 can slide, and which in some embodiments can rotate the prongs 1109 1110 around a shaft 1112;
- an optional connector 1111 between the prong support 1108 and the shaft 1112;
- a sleeve 1104 for mounting the add-on device 1100 to the shaft 1112;
- a first control 1105 for optionally providing the rotational movement to the shaft 1112;
- a second control 1106 for optionally moving the prongs 1109 1110 toward or away from each other; and
- a wire 1107 or rod 1107 for transferring movement from the second control 1106 to the prongs 1109 1110, optionally along the shaft 1112.

In some embodiments the sleeve 1104 completely surrounds the shaft 1101 of the stapler 1102.

In some embodiments the sleeve 1104 surrounds a partial circumference of the shaft 1101 of the stapler 1102. In some embodiments an extent of the partial surrounding is in a range of angles from somewhat more than 180 degrees, for example 185 degrees; up to somewhat less than 360 degrees, for example 359 degrees. In some embodiments the partial-circumference sleeve 1104 is flexible, and can be stretched to open the along the lengthwise opening so as to slip sideways over the shaft 1101 of the stapler 1102.

In some embodiments the sleeve 1104 optionally serves for transferring rotational movement to the shaft 1112.

In some embodiments the sleeve 1104 optionally serves for transferring translational movement to the shaft 1112.

FIG. 11C shows a simplified illustration of the add-on device 1100 in place, added onto the stapler 1102 and shaft 1101.

In some embodiments the first control 1105 optionally serves to rotate the shaft 1112, optionally causing the prongs 1109 1110 to jut out of a diameter of the stapler 1102 or fold into the stapler 1102.

In some embodiments the second control 1106 optionally serves to push or pull the wire 1107 or rod 1107, optionally causing the prongs 1109 1110 to move away from or toward each other.

FIG. 11D shows a simplified illustration of the stapler 1102 at an end of the shaft 1101 in more detail.

FIG. 11D shows components of an example embodiment of a stapler 1102 suitable for adding an add-on component, by way of a non-limiting example an add-on component 1100 as shown in FIGS. 11B and 11C.

FIG. 11D shows an anvil 114 and staples 1116.

In some embodiments the stapler 1102 optionally includes a cartridge 1116 of staples. In some embodiments the cartridge 1116 is optionally narrower than a width of the stapler 1102, leaving a space 1118 for components of the add-on 1100, such as, by way of some non-limiting examples, the prongs 1109 1110 and/or the prong support 1108. In some embodiments the space 1118 potentially enables rolling the prongs 1109 1110 and/or the prong support 1108 into the stapler 1102, so that the stapler 1102 does not become wider, and can pass through a trocar, similarly to a stapler without the add-on.

FIG. 11E shows a simplified illustration of the add-on device 1100 of FIGS. 11B and 11C in place, added onto the stapler 1102 and shaft 1101.

FIG. 11E shows a simplified illustration of the add-on device 1100 of FIGS. 11B and 11C in place, added onto the stapler 1102 and shaft 1101.

FIG. 11E is an enlarged view, which shows:
- the two prongs 1109 1110 for drawing edges of a tissue opening toward each other;
- the prong support 1108 for supporting the prongs 1109 1110, along which one or more of the prongs 1109 1110 can slide, and which in some embodiments can rotate the prongs 1109 1110 around the shaft 1112 shown in FIGS. 11B and 11C;
- the optional connector 1111 between the prong support 1108 and the shaft 1112; and
- the sleeve 1104 for transferring rotational movement to the shaft 1112.

FIG. 11F shows a stapler 1102 and a shaft 1101, without an optional cartridge 1116 of staples. FIG. 11F also shows a stapler anvil 114 and a space 1120.

In some embodiments the space 1120 optionally serves for accepting a standard stapler cartridge therein. In some embodiments the standard stapler cartridge optionally includes 4 rows of staples. In some embodiments the standard stapler cartridge optionally includes N rows of staples.

In some embodiments the space 1120 optionally serves for accepting a modified stapler cartridge therein, which leaves a space such as the space 1118 shown in FIG. 11D. In some embodiments the modified stapler cartridge optionally includes 3 rows of staples. In some embodiments the standard stapler cartridge optionally includes N−1 or N−2 rows of staples.

Some features of example embodiments of an add-on device as described herein include:

Providing features of capturing tissue opening edges and/or drawing tissue opening edges toward each other and/or stapling tissue and/or tissue cutting, all in a single tool/device;
  embodiments of the add-on device can be made to fit existing tissue staplers and existing laparoscopic tissue staplers;
  embodiments of the add-on device allow use of standard staple cartridges, and some embodiments include specially customized staple cartridges
  converting a laparoscopic tissue stapler to a laparoscopic tissue stapler with enhanced capabilities including one or more of capturing tissue opening edges and/or drawing tissue opening edges toward each other and/or tissue cutting, all in a single tool/device;
  providing easy tissue capture capabilities using prongs or tissue capture mechanism;
  providing easy tissue alignment capabilities;
  providing external controls for one or more of tissue capture, tissue alignment; tissue stapling, tissue cutting; and
  the above-mentioned enhanced capability laparoscopic tissue stapler is sized to pass through a trocar.

In some embodiments the add-on device enlarges a stapler diameter by a specific amount, by way of some non-limiting examples, by 1, 2, 3, 4, 5 millimeters, or otherwise phrased, by an amount in a range of 1-5 millimeters or more.

In some embodiments the enhanced capability laparoscopic tissue stapler can pass through a trocar with a 15 mm diameter.

In some embodiments the add-on device enlarges a stapler diameter so that, by way of some non-limiting examples, the enhanced capability laparoscopic tissue stapler with a stapler diameter of 12 mm passes through a 15 mm trocar, a stapler diameter of 10 mm passes through 12 mm trocar, a stapler diameter of 8 mm passes through a 10 mm trocar.

Reference is now made to FIG. 11G, which is a simplified flow chart illustration of a method for constructing a device for laparoscopic surgical closure of an opening in tissue.

The method of FIG. 11G includes:
  providing an add-on device (1132);
  providing a tissue stapler (1134); and
  mounting the add-on device onto the tissue stapler (1136).
  In some embodiments, the add-on device includes:
  a first tissue engaging component configured to engage an opening in tissue near a first location in the opening;
  a second tissue engaging component configured to engage the opening near a second location in the opening;
  a spreader component configured to move the first tissue engaging component away from the second tissue engaging component;
  a control for moving the first tissue engaging component away from the second tissue engaging component, the control configured to be external to a patient's body.

Two Tools

Reference is now made to FIGS. 12A-12D, which are simplified illustrations of a system according to an example embodiment of the invention.

FIGS. 12A-12D show a system which includes two tools for providing tissue stapler and functionality of drawing edges of a tissue opening toward each other.

FIG. 12A shows a first tool 1202 for stapling tissue, and a second tool 1204 for drawing edges of a tissue opening toward each other.

In some embodiments the first tool 1202 includes a tissue stapler 1206, a shaft 1208, and a handle 1210. In some embodiments the handle 1210 includes controls for operating the tissue stapler. In some embodiments the first tool 1202 includes a tissue cutter, and the controls also operate the tissue cutter.

FIG. 12B shows a larger view of the second tool 1204 for capturing tissue opening edges and/or drawing edges of a tissue opening toward each other.

FIG. 12B shows the second tool having a first component 1212 for capturing tissue opening edges and/or drawing edges of a tissue opening toward each other, an optional hinge 1214, a shaft 1215, a first control 1216, and a handle 1218.

FIG. 12C shows a yet larger view of a distal end of the second tool 1204, showing details of the first component 1212.

FIG. 12C shows two prongs 1222 1224 for capturing tissue opening edges and/or drawing tissue opening edges toward each other, a prong support 11220, an optional interface 1226 for aligning and/or controlling a relative position of the second tool 1204 and the first tool 1202, and a second optional tab 1232 for aligning and/or controlling a relative position of the second tool 1204 and the first tool 1202.

In some embodiments the first tool 1202 is a standard tissue stapler.

In some embodiments the first tool 1202 is a modified tissue stapler, modified to engage with the second tool 1204.

FIG. 12D shows a larger view of a distal end of a modified first tool 1202, and a portion of the second tool 1204 in place in the distal end of the modified first tool 1202.

FIG. 12D shows optional features of the modified first tool 1212 for engaging with the second component, with the prong support 1220 placed in the tissue stapler 1206 of the first tool 1202 and aligned with the tissue stapler 1206 of the first tool 1202.

FIG. 12D shows the prongs 1222 1224 within the modified first tool 1212.

In some embodiments the optional interface 1226 of the second tool 1204 is optionally cone shaped, as shown in FIGS. 12B and 12C, and corresponds to an engaging interface 1228 on the first tool 1202, as shown in FIG. 12D.

In some embodiments the first control 1216 is a control which controls movement of the prongs 1222 1224 toward each other or away from each other, potentially in order to capture tissue opening edges and/or drawing tissue opening edges toward each other.

Some features of example embodiments of a two-tool system as described herein include:
  providing separate controls for capturing tissue opening edges and separate for tissue stapling;
  providing a physician separate control of location and/or attitude of the tissue aligner and the tissue stapler;
  each one of the may pass through a trocar of only 12 mm in diameter; each one of the first tool 1204 and the second tool 1202 may pass through a trocar of only 12 mm in diameter; and the first tool 1204 for capture tissue opening edges and/or drawing tissue opening edges toward each other can pass through a trocar of only 5 mm in diameter, or larger, for example in a range of 4 mm to 12 mm.

Reference is now made to FIGS. 12E and 12F which are simplified illustrations of optional features in an example embodiment of the invention.

FIGS. 12E and 12F show that prongs 1222 and 1224 of the component 1212 for capturing tissue opening edges and/or drawing edges of a tissue opening toward each other of FIGS. 12A-12D can optionally be folded into the component 1212, and optionally be caused to jut out of the component 1212.

FIG. 12E show the prongs 1222 and 1224 folded into the component 1212.

FIG. 12F show the prongs 1222 and 1224 jutting out of the component 1212.

In some embodiments the component 1212 is inserted into a patient's body with the prongs 1222 1224 folded.

In some embodiments the component 1212 with the prongs 1222 1224 folded can pass through a small diameter trocar, as small as 2-5 millimeters in diameter.

In some embodiments the prongs 1222 1224 are optionally constructed of shape memory material, with their unfolded shape being the shape which the material forms when released.

In some embodiments the prongs 1222 1224 are optionally folded into the component 1212, and the component 1212 is optionally inserted through a trocar or even a catheter. When a section of the component 1212 is extruded from the trocar or catheter, the shape memory material of the prongs 1222 1224 optionally causes the prongs 1222 1224 to jut out from the component 1212, as shown in FIG. 12E.

Prongs on Anvil

In some embodiments, prongs for capturing tissue-opening edges and/or drawing tissue-opening edges toward each other are optionally placed on an anvil side of a tissue stapler device.

Reference is now made to FIG. 13, which is a simplified illustration of a device according to an example embodiment of the invention.

FIG. 13 shows a device in which a tissue stapler includes functionality for capturing tissue-opening edges and/or drawing tissue-opening edges toward each other.

FIG. 13 shows a device 1300 which includes:
a tissue stapler 1302;
a shaft 1304; and
a handle 1308.

In some embodiments the handle 1210 includes controls for operating the tissue stapler 1302. In some embodiments the tissue stapler 1302 includes a tissue cutter, and the controls also operate the tissue cutter.

FIG. 13 shows the tissue stapler 1302 including an anvil 1310, having prongs 1312 1314 for capturing tissue-opening edges and/or drawing tissue-opening edges toward each other on one side, or jaw, of the tissue stapler 1302, and a stapling mechanism or staple cartridge 1308 on another side, or jaw, of the tissue stapler 1302.

In some embodiments the controls also operate the prongs 1312 1314. In some embodiments the controls operate the prongs 1312 1314 by wire, so as to transfer control, or movement, through an angle of an open jaw of the tissue stapler 1302.

Some features of example embodiments of a device with the tissue capture capability on a tissue stapler anvil include:

providing features of capturing tissue opening edges and/or drawing tissue opening edges toward each other and/or stapling tissue and/or tissue cutting, all in a single tool/device;

providing controls for the above functionality in one device; and the device may pass through a trocar of only 12 mm in diameter.

Controls

FIGS. 5A, 5D, 10A, 10B, 12A-D, and 13 show devices including example embodiments of controls for controlling embodiments of devices shown in the Figures. The controls optionally control one or more of:

opening/closing an anvil of a tissue stapler;
rotating prongs or tissue graspers about a shaft;
moving prongs or tissue graspers toward or away from each other;
operating and/or triggering a tissue stapler; and
operating and/or triggering a tissue cutter.

The number of controls optionally ranges, by way of some non-limiting examples, from one control, to two controls, to three controls, to four controls, to five controls.

It is expected that during the life of a patent maturing from this application many relevant tissue attachment devices such as sutures, staples, and adhesives will be developed and the scope of the term tissue attachment device is intended to include all such new technologies a priori.

As used herein the term "about" refers to ±25%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for attaching opposing edges of an opening in a tissue to one another, the method comprising:
    using a first tissue engaging component to engage an opening in a tissue at a first location in said opening;
    using a second tissue engaging component to engage said opening at a second location in said opening;
    using a spreader component to move the first tissue engaging component away from the second tissue engaging component which causes opposing edges of said opening to be drawn closer together; and
    using a tissue attachment mechanism to attach portions of the tissue adjacent said opposing edges to one another, and wherein said first tissue engaging component and said second tissue engaging component are movably mounted on a common mounting element and said common mounting element is movable with respect to said tissue attachment mechanism.

2. The method according to claim 1, wherein using said tissue attachment mechanism to attach portions of the tissue adjacent said opposing edges to one another closes said opening.

3. The method according to claim 1, wherein said tissue attachment mechanism is used to attach portions of the tissue adjacent said opposing edges of said opening to one another by stapling them together.

4. The method according to claim 1, further comprising moving said tissue over a portion of said tissue attachment mechanism prior to using said tissue attachment mechanism to attach portions of the tissue to one another.

5. The method according to claim 1, further comprising cutting a part of the tissue.

6. The method according to claim 1, wherein the moving of said tissue over a portion of said tissue attachment mechanism prior to using said tissue attachment mechanism to attach portions of the tissue to one another comprises movement of said common mounting element, on which said first tissue engaging component and said second tissue engaging component are mounted, with respect to said tissue attachment mechanism.

7. The method according to claim 6, wherein said movement comprises rotating said common mounting element about a longitudinal axis of said tissue attachment mechanism.

8. The method according to claim 1, further comprising cutting tissue which is adjacent to said portions of the tissue that have been attached to one another.

9. The method according to claim 1, wherein the method is performed in a laparoscopic procedure.

* * * * *